US009862693B2

(12) United States Patent
Pietras et al.

(10) Patent No.: US 9,862,693 B2
(45) Date of Patent: Jan. 9, 2018

(54) COMPOUNDS AND METHODS OF TREATING CANCER

(71) Applicant: The Regents of the University of California, Oakland, CA (US)

(72) Inventors: Richard J. Pietras, Los Angeles, CA (US); Michael E. Jung, Los Angeles, CA (US); Diana C. Marquez-Garban, Los Angeles, CA (US); Gang Deng, Los Angeles, CA (US)

(73) Assignee: The Regents of the University of California, Oaklnad, CA (US)

( * ) Notice: Subject to any disclaimer, the term of this patent is extended or adjusted under 35 U.S.C. 154(b) by 40 days.

(21) Appl. No.: 14/566,055

(22) Filed: Dec. 10, 2014

(65) Prior Publication Data

US 2015/0158832 A1 Jun. 11, 2015

Related U.S. Application Data

(63) Continuation of application No. PCT/US2013/045250, filed on Jun. 11, 2013.

(60) Provisional application No. 61/658,238, filed on Jun. 11, 2012.

(51) Int. Cl.
| | |
|---|---|
| *C07D 295/215* | (2006.01) |
| *C07D 203/20* | (2006.01) |
| *C07D 211/16* | (2006.01) |
| *C07D 213/78* | (2006.01) |
| *C07D 239/28* | (2006.01) |
| *C07D 401/12* | (2006.01) |
| *A61K 31/155* | (2006.01) |
| *C07C 279/26* | (2006.01) |
| *A61K 31/4025* | (2006.01) |
| *A61K 31/445* | (2006.01) |
| *A61K 31/4545* | (2006.01) |
| *A61K 31/496* | (2006.01) |
| *A61K 31/5377* | (2006.01) |
| *C07C 279/22* | (2006.01) |

(52) U.S. Cl.
CPC ........ *C07D 295/215* (2013.01); *A61K 31/155* (2013.01); *A61K 31/4025* (2013.01); *A61K 31/445* (2013.01); *A61K 31/4545* (2013.01); *A61K 31/496* (2013.01); *A61K 31/5377* (2013.01); *C07C 279/22* (2013.01); *C07C 279/26* (2013.01); *C07D 203/20* (2013.01); *C07D 211/16* (2013.01); *C07D 213/78* (2013.01); *C07D 239/28* (2013.01); *C07D 401/12* (2013.01)

(58) Field of Classification Search
CPC ............ C07D 295/215; C07D 203/20; C07D 211/16; C07D 213/78; C07D 239/28; C07D 401/12
See application file for complete search history.

(56) References Cited

U.S. PATENT DOCUMENTS

| | | | | |
|---|---|---|---|---|
| 4,574,123 A | * | 3/1986 | Edwards ............... | C07C 279/28 162/161 |
| 4,861,760 A | | 8/1989 | Mazuel et al. | |
| 4,911,920 A | | 3/1990 | Jani et al. | |
| 5,212,162 A | | 5/1993 | Missel et al. | |
| 5,403,841 A | | 4/1995 | Lang et al. | |
| 6,699,989 B1 | * | 3/2004 | Shetty .................. | C07D 215/56 540/474 |
| 7,285,681 B2 | * | 10/2007 | Moinet .............. | C07D 295/215 564/233 |
| 7,671,019 B2 | * | 3/2010 | Tobia ....................... | A61K 8/44 514/1.1 |
| 8,853,259 B2 | | 10/2014 | Mylari | |
| 2010/0087544 A1 | | 4/2010 | Kim et al. | |
| 2011/0196015 A1 | | 8/2011 | Kim et al. | |
| 2011/0207810 A1 | | 8/2011 | Kim et al. | |
| 2015/0126518 A1 | | 5/2015 | Kim et al. | |

FOREIGN PATENT DOCUMENTS

| | | |
|---|---|---|
| WO | WO-96/05309 A2 | 2/1996 |
| WO | WO-96/05309 A3 | 2/1996 |
| WO | WO-2011/083998 A2 | 7/2011 |
| WO | WO-2011/083998 A3 | 7/2011 |
| WO | WO-2011/147528 A1 | 12/2011 |

OTHER PUBLICATIONS

CAPLUS on STN, accession No. 2010:923694, Abstract of CN101781273 Jul. 21, 2010.*
Registry No. 793641-52-8, CAPLUS on STN, Dec. 7, 2004.*
Alimova I.N. et al. (Mar. 15, 2009). "Metformin inhibits breast cancer cell growth, colony formation and induces cell cycle arrest in vitro," *Cell Cycle* 8(6):909-915.
Berstein, L.M. (Aug. 2010). "Modern approach to metabolic rehabilitation of cancer patients: biguanides (phenformin and metformin) and beyond," *Future Oncol* 6(8):1313-23.
Carey, L.A. et al. (Jun. 7, 2006). "Race, breast cancer subtypes, and survival in the Carolina Breast Cancer Study," *JAMA* 295(21):2492-2502.
Currie C.J. et al. (Feb. 2012, e-published Jan. 20, 2012). "Mortality after incident cancer in people with and without type 2 diabetes: impact of metformin on survival," *Diabetes Care* 35(2):299-304.
Dowling, R.J. et al. (Apr. 6, 2011). "Understanding the benefit of metformin use in cancer treatment," *BMC Med*: 9:33.
Dilman, V.M. et al. (1982). "Metabolic immunodepression and metabolic immunotherapy: an attempt of improvement in immunologic response in breast cancer patients by correction of metabolic disturbances," *Oncology* 39(1):13-19.
Evans, J.M. et al. (Jun. 4, 2005). "Metformin and reduced risk of cancer in diabetic patients," *BMJ* 330(7503):1304-1305.
Foulkes, W.D. et al. (Nov. 11, 2010). "Triple-negative breast cancer," *N Engl J Med*. 363(20):1938-1948.
International Search Report dated Nov. 1, 2013, for PCT Application No. PCT/US2013/045250, filed on Jun. 11, 2013, 4 pages.
James, J.W. et al. (Sep. 1968). "The synthesis of some heterocyclic derivatives of biguanide with antibacterial activity," *J Med Chem* 11(5):942-945.

(Continued)

*Primary Examiner* — Rebecca L Anderson
(74) *Attorney, Agent, or Firm* — Zachary L. Terranova; Mintz, Levin, Cohn, Ferris, Glovsky and Popeo, P.C.

(57) ABSTRACT

Presented herein inter alia are novel compounds and methods of using the same for the treatment of cancers.

7 Claims, 10 Drawing Sheets

(56) References Cited

OTHER PUBLICATIONS

Jiralerspong, S. et al. (Jul. 10, 2009, e-published Jun. 1, 2009). "Metformin and pathologic complete responses to neoadjuvant chemotherapy in diabetic patients with breast cancer," *J Clin Oncol.* 27(20):3297-3302.

Jiralerspong, S. et al. (Sep. 1, 2009). "Expanding the arsenal: metformin for the treatment of triple-negative breast cancer?" *Cell Cycle*: 8(17):2681-2684.

Kihara, Y. et al. (1990). *Journal of Heterocyclic Chemistry* 27:1213-1216.

Kelarev, V.I. et al. (May 1988). "Synthesis and properties of sym-triazine derivatives. 7. Synthesis of pyridyl-substituted 2-amino- and 2,4-diamino-sym-triazines," *Chemistry of Heterocyclic Compounds 24*(5):550-555.

Kelarev, V.I. et al. (Sep. 1992). "Synthesis and properties of sym-triazine derivatives 9. Synthesis of 2-amino- and 2,4-diamino-sym-triazines containing furan fragments," *Chemistry of Heterocyclic Compounds* 28(9):1060-1065.

Kelarev, V.I. et al. (Sep. 1993). "Synthesis and properties of derivatives of sym-triazines. 11. Synthesis of 2-amino-sym-triazines containing alkyl radicals," *Chemistry of Heterocyclic Compounds* 29(9):1087-1092.

Koh, M. et al. (Apr. 2013, e-published Feb. 22, 2013). "A novel metformin derivative, HL010183, inhibits proliferation and invasion of triple-negative breast cancer cells," *Bioorg Med Chem* 21(8):2305-2313.

Liu, B. et al. (Jul. 1, 2009, e-published Jul. 21, 2009). "Metformin induces unique biological and molecular responses in triple negative breast cancer cells," *Cell Cycle* 8(13):2031-2040.

Nagasaka, H. et al. Yuki Gosei Kagaku Kyokaishi (1967). 25(9):802-807. (English translation of Abstract only).

Sahra, I. B. et al. (May 2010, e-published May 4, 2010). "Metformin in cancer therapy: a new perspective for an old antidiabetic drug?" *Mol Cancer Ther* 9(5):1092-1099.

Taubes, G. (Jan. 6, 2012). "Cancer research. Unraveling the obesity-cancer connection," *Science* 335(6064):28, 30-32.

Written Opinion dated Nov. 1, 2013, for PCT Application No. PCT/US2013/045250, filed on Jun. 11, 2013, 7 pages.

\* cited by examiner

COMPOUNDS AND METHODS OF TREATING CANCER

CROSS-REFERENCES TO RELATED APPLICATIONS

This application is a continuation of PCT Application No. PCT/US2013/045250, filed Jun. 11, 2013 which claims the benefit of U.S. Application No. 61/658,238, filed Jun. 11, 2012 which are incorporated herein by reference in their entirety and for all purposes.

BACKGROUND OF THE INVENTION

Breast Cancer is the most common type of cancer that occurs in women in the US, and it ranks as the second leading cause of cancer death after lung cancer. About 15-20% of breast cancers are classified as "triple negative" (TNBC), a subtype that lacks clinical expression of estrogen receptor-alpha, progesterone receptor and HER-2 overexpression or lacks clinical expression of ERα, progesterone receptor and HER2 receptor or lacks immunohistochemical expression of ERα, progesterone receptor and HER-2 receptor overexpression. These patients will face limited and often ineffective therapeutic options. Thus, there is an urgent need to develop new and more effective therapies for this deadly subtype of breast cancer. Triple-negative breast cancer (TNBC) cannot be treated with current endocrine or HER-2 targeted therapies (11). TNBC occurs in about 15-20% of breast cancers, yet accounts for nearly half of all breast cancer deaths. It is associated with a significantly higher probability of relapse and worse overall survival in the first few years after diagnosis when compared with other breast cancer subtypes (12). This is observed despite its high sensitivity to chemotherapy. Although initially responsive to some chemotherapies, TNBCs tend to relapse early and metastasize, leading to poor patient survival.

Pancreatic carcinoma is a highly lethal disease and the fourth-leading cause for cancer death in men and women in the US (1). The overall 5-year survival rate is approximately 4%. Conventional treatment approaches (chemotherapy, radiation, surgery or combinations of these modalities) have had little impact on the course of this disease. Surgical resection is the only chance at cure, but most patients present with advanced, unresectable disease (2,3). Since effective therapies are largely lacking, it is clear that new therapeutic approaches to treat pancreatic cancer are urgently needed. Metformin (1,1-dimethyl-biguanide hydrochloride) is a widely prescribed antihyperglycemic drug used as first-line therapy for diabetes mellitus type 2, and is now reported to have antitumor efficacy in pancreatic cancer (4-7). The primary systemic effect of metformin is to lower blood glucose, but it also reduces hyperinsulinemia associated with insulin resistance. Provided herein are solutions to these and other problems in the art.

BRIEF SUMMARY OF THE INVENTION

In a first aspect, a compound is provided having the formula:

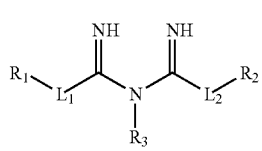

(I)

$L^1$ and $L^2$ are independently a bond or —NH—C(NH)—. $R^1$ is —$NR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{1A}$ and $R^{1B}$ are optionally joined together to form a substituted or unsubstituted heterocycloalkyl. $R^2$ is —$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{2A}$ and $R^{2B}$ are optionally joined together to form a substituted or unsubstituted heterocycloalkyl. $R^{1A}$, $R^{1B}$, $R^{2A}$, and $R^{2B}$ are independently hydrogen, —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or unsubstituted $C_1$-$C_5$ alkyl. $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, a pharmaceutical composition is provided. The composition includes a pharmaceutically acceptable excipient and a compound having formula:

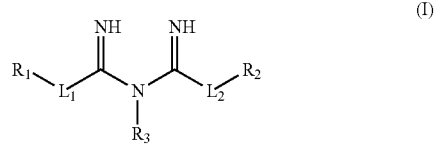

(I)

$L^1$ and $L^2$ are independently a bond or —NH—C(NH)—. $R^1$ is —$NR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{1A}$ and $R^{1B}$ are optionally joined together to form a substituted or unsubstituted heterocycloalkyl. $R^2$ is —$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{2A}$ and $R^{2B}$ are optionally joined together to form a substituted or unsubstituted heterocycloalkyl. $R^{1A}$, $R^{1B}$, $R^{2A}$, and $R^{2B}$ are independently hydrogen, —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or unsubstituted $C_1$-$C_5$ alkyl. $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, a method of treating cancer in a subject in need thereof is provided. The method includes administering a therapeutically effective amount a compound having formula:

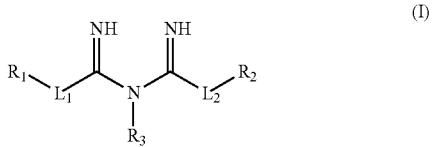

(I)

L¹ and L² are independently a bond or —NH—C(NH)—. R¹ is —NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{1A}$ and R$^{1B}$ are optionally joined together to form a substituted or unsubstituted heterocycloalkyl. R² is —NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{2A}$ and R$^{2B}$ are optionally joined together to form a substituted or unsubstituted heterocycloalkyl. R$^{1A}$, R$^{1B}$, R$^{2A}$, and R$^{2B}$ are independently hydrogen, —OR⁴, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R³ is hydrogen or unsubstituted $C_1$-$C_5$ alkyl. R⁴ is hydrogen, substituted or unsubstituted alkyl, substituted or unsubstituted heteroalkyl, substituted or unsubstituted cycloalkyl, or unsubstituted heterocycloalkyl, substituted or unsubstituted aryl, or substituted or unsubstituted heteroaryl.

DETAILED DESCRIPTION OF THE INVENTION

I. Definitions

Figure 1:
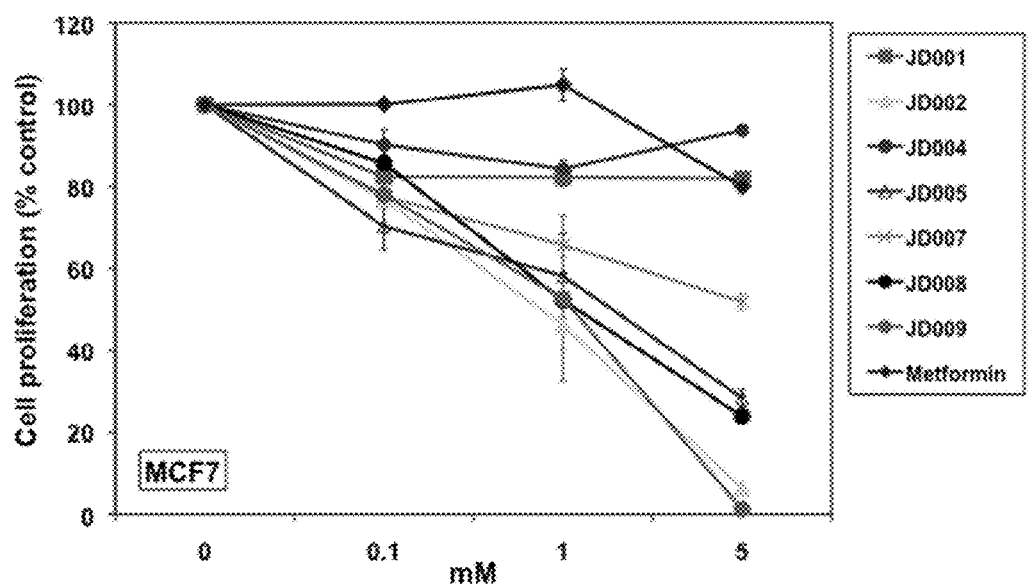
FIG. 1. Metformin analogues inhibit growth/survival of ER+ MCF7 breast cancer cells. MCF7 cells were cultured in medium containing different concentrations of metformin and analogues (0.1, 1 and 5 mM). After 3 days, the percentage of surviving cells relative to controls, defined as 100% survival, was determined by the MTS assay. Data represents three independent experiments.
Figure 2A:
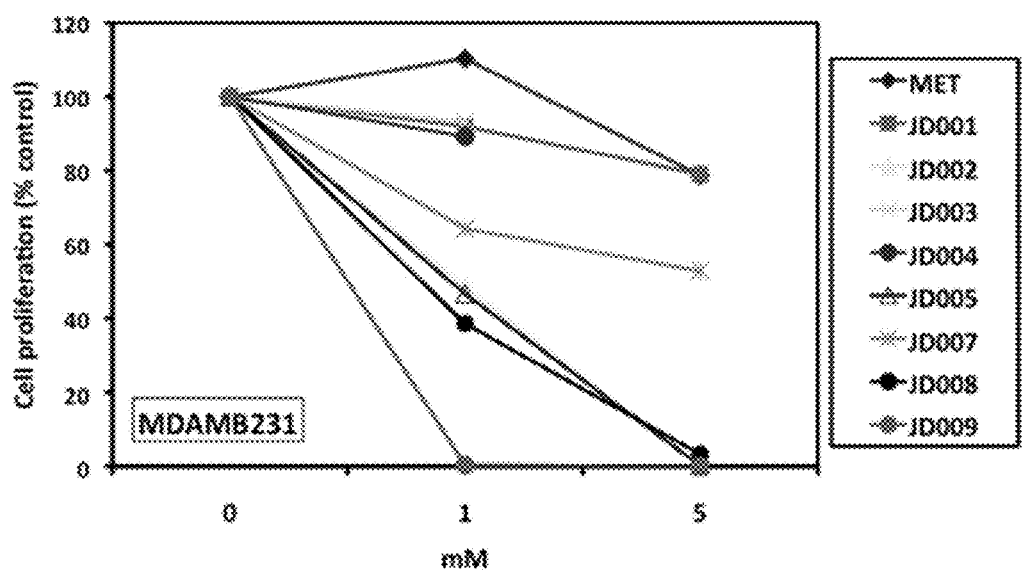
FIGS. 2A-2D. Metformin analogues inhibit growth/survival of triple negative breast cancer cells. MDA-MB-231 (FIG. 2A), HCC38 (FIG. 2B), HCC1937 (FIG. 2C) and HCC1806 (FIG. 2D) cells were cultured in medium containing 1% fetal bovine serum and increasing concentrations of metformin and analogues JD001-JD009 (0.1, 1 and 5 mM). After 3 days, MTS assay was performed. The percentage of surviving cells relative to controls, defined as 100% survival, was determined by the MTS assay.
Figure 2B:
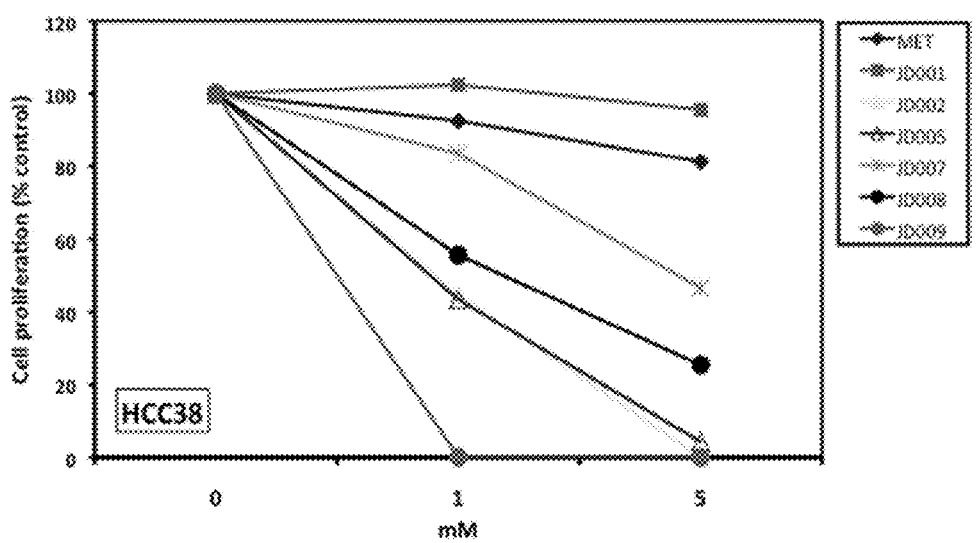
Figure 2C:
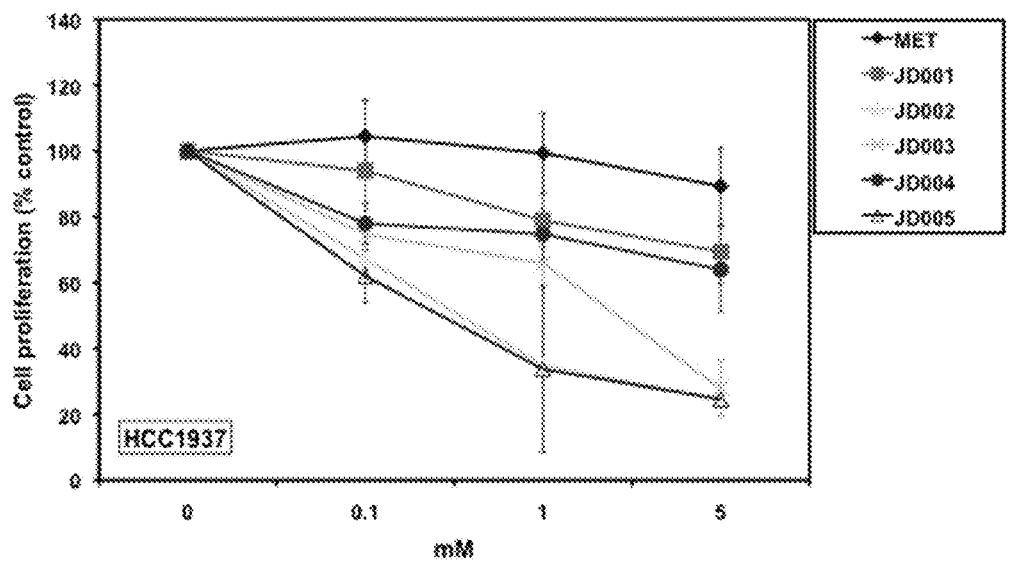
Figure 2D:
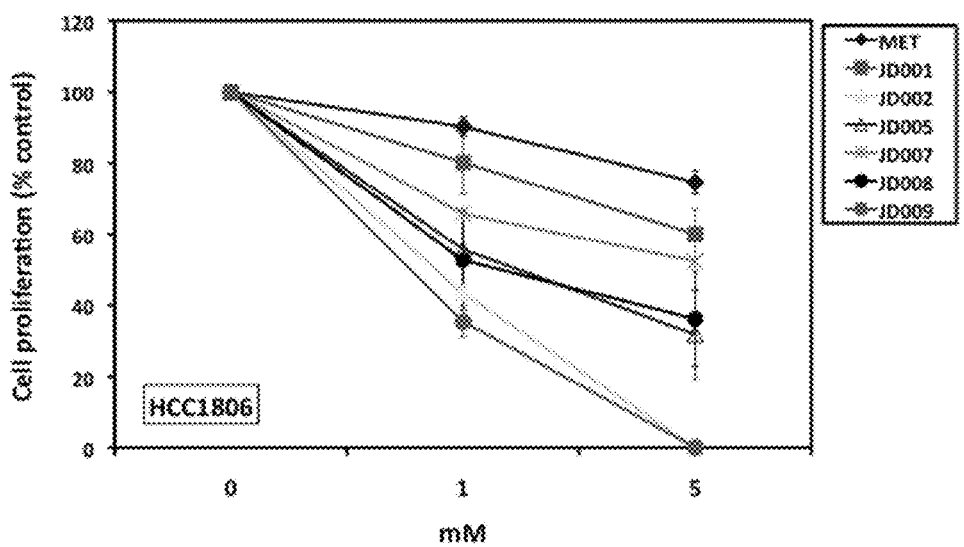

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH₂O— is equivalent to —OCH₂—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

In some embodiments, the heterocycloalkyl may be a fused ring heterocycloalkyl-aryl which is an aryl fused to a heterocycloalkyl. In some embodiments, the heterocycloalkyl may be a fused ring heterocycloalkyl-heteroaryl which is a heteroaryl fused to a heterocycloalkyl. In some embodiments, the heterocycloalkyl may be a fused ring heterocycloalkyl-cycloalkyl which is a heterocycloalkyl fused to a cycloalkyl. In some embodiments, the heterocycloalkyl may be a fused ring heterocycloalkyl-heterocycloalkyl which is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR' R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

A heteroaryl group substituent may be a —O$^-$ bonded to a ring heteroatom nitrogen.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, —COOH, —CONH$_2$, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) —OH, —NH$_2$, —SH, —CN, —CF$_3$, —NO$_2$, oxo, halogen, —COOH, —CONH$_2$, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, and
(ii) alkyl, heteroalkyl, cycloalkyl, heterocycloalkyl, aryl, and heteroaryl, substituted with at least one substituent selected from:
(a) —OH, —NH$_2$, —SH, —CN, —CF$_3$, —NO$_2$, OXO, halogen, —COOH, —CONH$_2$, —SO$_2$Cl, —SO$_3$H, —SO$_4$H, —SO$_2$NH$_2$, —NHNH$_2$, —ONH$_2$, —NHC═(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from: —OH, —NH$_2$, —SH, —CN, —CF$_3$, —NO$_2$, oxo, halogen, —COOH, —CONH$_2$, —SO$_2$Cl, —SO$_3$H, —SO$_4$H, —SO$_2$NH$_2$, —NHNH$_2$, —ONH$_2$, —NHC═(O)NHNH$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In embodiments, each substituted group described in the compounds herein is substituted with at least one substituent group. More specifically, in embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene. In embodiments, the compound is a chemical species set forth in the Examples section below or Table 1.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)-for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "⌇" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls and each such unsubstituted alkyl may be different and each such unsubstituted heteroalkyl may be different. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein may successfully treat cancer by decreasing the incidence of cancer and or causing remission of cancer (e.g. breast cancer, triple negative breast cancer subtype, lung cancer, non-small cell lung cancer, pancreatic cancer, melanoma, colon cancer, prostate cancer, or ovarian cancer). The term "treating," and conjugations thereof, include prevention of an injury, pathology, condition, or disease.

An "effective amount" or "therapeutically effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (e.g. compound) required to decrease the activity of an enzyme relative to the absence of the antagonist. A "function disrupting amount," as used herein, refers to the amount of antagonist (e.g. compound) required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. For example, a control for determining expression or overexpression of a protein or marker (e.g. estrogen receptor alpha, progesterone receptor, or human epidermal growth factor receptor 2) may be the amount of protein or marker expressed by a non-cancerous tissue or cell having the same cellular origin as the cancerous tissue or cell being compared to the control (e.g. breast, lung, pancreatic, skin, epidermal, prostate, ovarian, colon, or colorectal). In embodiments, a control for expression or overexpression may be the average amount of expression of a protein or marker in the corresponding tissue or cells of a person without the disease being treated or monitor or diagnosed (e.g. cancer).

"Contacting" is used in accordance with its plain ordinary meaning and refers to the process of allowing at least two distinct species (e.g. chemical compounds including biomolecules, proteins, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a cancer cell. In embodiments, the cancer cell may be a breast cancer cell. In embodiments, the cancer cell may be a triple negative breast cancer cell. In embodiments, the cancer cell may be a lung cancer cell. In embodiments, the cancer cell may be a non-small cell lung cancer cell. In embodiments, the cancer cell may be a pancreatic cancer cell. In embodiments, the cancer cell may be a melanoma cancer cell. In embodiments, the cancer cell may be a colon cancer cell. In embodiments, the cancer cell may be a colorectal cancer cell. In embodiments, the cancer cell may be an ovarian cancer cell. In embodiments, the cancer cell may be a prostate cancer cell. In embodiments contacting includes allowing a compound described herein to interact with a protein associated with the cell.

As defined herein, the term "inhibition", "inhibit", "inhibiting" and the like in reference to a protein-inhibitor interaction means negatively affecting (e.g. decreasing) the activity or function of the protein (e.g. decreasing the activity of a protein) relative to the activity or function of the protein in the absence of the inhibitor (e.g. compound). In embodiments inhibition refers to reduction of a disease or symptoms of disease. In embodiments, inhibition refers to a reduction in the presence of a disease-related protein. Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound that inhibits cancer cell growth or proliferation, e.g., by binding, partially or totally blocking stimulation of cell growth or proliferation, decreasing, preventing, or delaying activation (e.g. of a protein or enzyme involved in cancer cell growth or proliferation), or inactivating, desensitizing, or down-regulating signal transduction or enzymatic activity (e.g. activity responsible for cancer cell growth or proliferation). Inhibition may also reduce the amount of a protein by increasing clearance or degradation of the protein.

The term "modulator" refers to a composition that increases or decreases the level of a target molecule or the function of a target molecule (e.g. a target may be a cancer associated protein or mutant protein and the function may be increase cell growth or a target may be a cancer cell and the function may be to replicate and multiply). In embodiments, a modulator is a compound that reduces the severity of one or more symptoms of a disease (e.g. tumor growth or metastasis).

"Patient" or "subject in need thereof" refers to a living organism suffering from or prone to a condition that can be treated by administration of a composition (e.g. compound) or pharmaceutical composition as provided herein. Non-limiting examples include humans, other mammals, bovines, rats, mice, dogs, monkeys, goat, sheep, cows, deer, and other non-mammalian animals. In embodiments, a patient is human.

"Disease" or "condition" or "disorder" refers to a state of being or health status of a patient or subject capable of being treated with the compounds, drugs, pharmaceutical compositions, or methods provided herein. In embodiments, the disease is a disease related to (e.g. caused by) an abnormal cell growth or abnormal protein activity. Examples of diseases, disorders, or conditions include, but are not limited to, cancer, metastatic cancer, breast cancer, triple-negative breast cancer subtype, pancreatic cancer, lung cancer, non-small cell lung cancer, melanoma, prostate cancer, ovarian cancer, colon cancer, colorectal cancer. In some instances, "disease" or "condition" refers to cancer. In embodiments, "disease" refers to triple negative breast cancer. In embodiments, "disease" refers to breast cancer. In embodiments, "disease" refers to lung cancer. In embodiments, "disease" refers to non-small cell lung cancer. In embodiments, "disease" refers to pancreatic cancer. In embodiments, "disease" refers to colon cancer. In embodiments, "disease" refers to colorectal cancer. In embodiments, "disease" refers to prostate cancer. In embodiments, "disease" refers to ovarian cancer. In embodiments, "disease" refers to melanoma. In embodiments, "disease" refers to pulmonary lymphangioleiomyomatosis (LAM). In embodiments, "disease" refers to renal angiomyolipoma (AML). In some further instances, "cancer" refers to human cancers and carcinomas, sarcomas, adenocarcinomas, lymphomas, leukemias, etc., including solid and lymphoid cancers, kidney, breast (e.g. triple negative subtype), lung, bladder, colon, ovarian, prostate, pancreas, stomach, brain cancer, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals, including leukemia, carcinomas and sarcomas. Exemplary cancers that may be treated with a compound or method provided herein include cancer of the brain, breast (e.g. triple negative), cervix, colon, colorectal, head & neck, liver, kidney, lung, non-small cell lung, melanoma, mesothelioma, ovary, sarcoma, stomach, uterus or medulloblastoma. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine. and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent identified herein having utility in methods of treating breast cancer. In embodiments, an anti-cancer agent is an agent identified herein having utility in methods of treating triple negative breast cancer. In embodiments, an anti-cancer agent is an agent identified herein having utility in methods of treating lung cancer. In embodiments, an anti-cancer agent is an agent identified herein having utility in methods of treating non-small cell lung cancer. In embodiments, an anti-cancer agent is an agent identified herein having utility in methods of treating pancreatic cancer. In embodiments, an anti-cancer agent is an agent identified herein having utility in methods of treating melanoma. In embodiments, an anti-cancer agent is an agent identified herein having utility in methods of treating colon cancer. In embodiments, an anti-cancer agent is an agent identified herein having utility in methods of treating colorectal cancer. In embodiments, an anti-cancer agent is an agent identified herein having utility in methods of treating prostate cancer. In embodiments, an anti-cancer agent is an agent identified herein having utility in methods of treating ovarian cancer. In embodiments, an anti-cancer agent is an agent approved by the FDA or similar regulatory agency of a country other than the USA, for treating cancer. Examples of anti-cancer agents include, but are not limited to, alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006), wortmannin, LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, amsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexamethasone, dexifosfamide, dexrazoxane, dexverapamil, diaziquone, didemnin B, didox, diethylnorspermine, dihydro-5-azacytidine, 9-dioxamycin, diphenyl spiromustine, docosanol, dolasetron, doxifluridine, droloxifene, dronabinol, duocarmycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance gene inhibitor, multiple tumor suppressor 1-based therapy, mustard anticancer agent, mycaperoxide B, mycobacterial cell wall extract, myriaporone, N-acetyldinaline, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, prednisone, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylerie conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen-binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfinosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thiocoraline, thrombopoietin, thrombopoietin mimetic, thymalfasin, thymopoietin receptor agonist, thymotrinan, thyroid stimulating hormone, tin ethyl etiopurpurin, tirapazamine, titanocene bichloride, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, zinostatin stimalamer, Adriamycin, Dactinomycin, Bleomycin, Vinblastine, Cisplatin, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cladribine, crisnatol mesylate, cyclophosphamide, cytarabine, dacarbazine, daunorubicin hydrochloride, decitabine, dexormaplatin, dezaguanine, dezaguanine mesylate, diaziquone, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, iimofosine, interleukin II (including recombinant interleukin II, or rIL.sub.2), interferon alfa-2a, interferon alfa-2b, interferon alfa-n1, interferon alfa-n3, interferon beta-1a, interferon gamma-1b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazoie, nogalamycin, ormaplatin, oxisuran, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride, agents that arrest cells in the G2-M phases and/or modulate the formation or stability of microtubules (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), or SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound. In embodiments, a reference compound is metformin.

As used herein, the term "disease-related cells" means cells that are associated with a disease or condition, which include but are not limited to cells that initiate a disease, cells that propogate a disease, cells that cause a disease, cells that cause one or more symptoms of a disease, cells that are a hallmark of a disease; cells that contain a particular protein or mRNA molecule that causes a symptom of the disease. In embodiments, the disease is a cancer (e.g. breast cancer, triple negative breast cancer subtype, lung cancer, non-small cell lung cancer, pancreatic cancer, melanoma, prostate cancer, ovarian cancer, colon cancer, or colorectal cancer) and the disease-related cell is a cancer (e.g. breast cancer, triple negative breast cancer subtype, lung cancer, non-small cell lung cancer, pancreatic cancer, melanoma, prostate cancer, ovarian cancer, colon cancer, or colorectal cancer) cell. In embodiments, the disease is a metastatic cancer and the disease-related cell is a metastatic cancer cell. In embodiments, the disease is triple negative breast cancer subtype (i.e. TNBC) and the disease-related cell is a TNBC cell.

The term "expression" refers to a gene that is transcribed or translated at a detectable level. As used herein, expression also encompasses "overexpression," which refers to a gene that is transcribed or translated at a detectably greater level, usually in a cancer cell, in comparison to a normal cell. Expression can be detected using conventional techniques for detecting protein (e.g., ELISA, Western blotting, flow cytometry, immunofluorescence, immunohistochemistry, etc.) or mRNA (e.g., RT-PCR, PCR, hybridization, etc.).

"Therapy resistant" cancers, tumor cells, and tumors refer to cancers that have become resistant to one or more therapies, including one or both of apoptosis-mediated (e.g., through death receptor cell signaling, for example, Fas ligand receptor, TRAIL receptors, TNF-R1, chemotherapeutic drugs, radiation, etc.) and non-apoptosis mediated (e.g., toxic drugs, chemicals, etc.) cancer therapies. In embodiments, the therapy may be a chemotherapy, hormonal therapy, radiotherapy, immunotherapy, or combinations thereof.

As used herein, the term "marker" refers to any biochemical marker, serological marker, genetic marker, or other clinical or echographic characteristic that can be used to diagnose or provide a prognosis for a cancer.

The term "sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In embodiments, the sample is obtained from a human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., breast, lung, pancreas, skin, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

As used herein, the term "administering" includes parenteral administration, oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The agents (e.g. compounds, drugs, antagonists) of the invention can be administered alone or can be coadministered to the patient. Coadministration is meant to include simultaneous or sequential administration of the agents (e.g. compounds, drugs, antagonists) individually or in combination (more than one agent (e.g. compound, drug, antagonist)). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. In embodiments, the compounds described herein (including embodiments) may be co-administered with one ore more anti-cancer agents.

"Triple negative breast cancer" or "triple negative breast cancer subtype" is used in accordance with its plain ordinary meaning within the areas of medicine and oncology and refer to breast cancer that lacks clinical expression of estrogen receptor-alpha, progesterone receptor and HER-2 overexpression or breast cancer that lacks clinical expression of estrogen receptor alpha, progesterone receptor and HER2 receptor. In embodiments, the level of expression or overexpress is in comparison to non-cancerous breast tissue.

In embodiments, the level of expression or overexpress is in comparison to non-cancerous breast tissue from the same patient as the cancerous tissue. In embodiments, the level of expression or overexpress is in comparison to the average expression of each marker in non-triple negative breast cancer samples (e.g. breast cancer samples). In embodiments, the level of expression or overexpression is in comparison to the expression levels in therapy responsive breast cancers that respond to therapies targeting one or more of estrogen receptor alpha, progesterone receptor, or human epidermal growth factor receptor 2. In embodiments triple negative breast cancer cells do not express (e.g. clinically) classical estrogen receptors (e.g. ER-alpha), do not express (e.g. clinically) progesterone receptors, and do not express (e.g. clinically) high levels of HER2/neu (epidermal growth factor receptor 2) compared to a control. In embodiments, triple negative breast cancer cells do not express (e.g. clinically) estrogen receptor alpha, progesterone receptor and HER2 receptor. In embodiments triple negative breast cancer subtype refers to breast cancer that lacks clinical expression of estrogen receptor-alpha, progesterone receptor and HER-2 overexpression. In embodiments triple negative breast cancer cells lack clinical expression of estrogen receptor-alpha, progesterone receptor and HER-2 overexpression.

II. Compounds

In a first aspect is a compound having the formula:

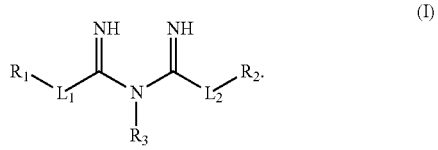

(I)

$L^1$ and $L^2$ are independently a bond or —NH—C(NH)—. $R^1$ is —$NR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{1A}$ and $R^{1B}$ are optionally joined together to form a substituted or unsubstituted heterocycloalkyl. $R^2$ is —$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{2A}$ and $R^{2B}$ are optionally joined together to form a substituted or unsubstituted heterocycloalkyl. $R^{1A}$, $R^{1B}$, $R^{2A}$, and $R^{2B}$ are independently hydrogen, —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or unsubstituted $C_1$-$C_5$ alkyl. $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In one embodiment, where $L^1$ and $L^2$ are a bond and $R^1$ is a piperidinyl substituted with an unsubstituted $C_1$ to $C_5$ alkyl (e.g. 4'-methyl piperidinyl), $R^2$ is not —$NH_2$. In one embodiment, where $L^1$ and $L^2$ are a bond and $R^1$ is a piperidinyl substituted with an unsubstituted $C_1$ to $C_5$ alkyl (e.g. 4'-substituted piperidinyl), $R^2$ is not —$NH_2$. In one embodiment, where $L^1$ and $L^2$ are a bond and $R^1$ is a piperidinyl substituted with an unsubstituted $C_1$ to $C_5$ alkyl (e.g. substituted piperidinyl), $R^2$ is not —$NH_2$. In one embodiment, where $L^1$ and $L^2$ are a bond and $R^1$ is substituted 3 to 6 membered heterocycloalkyl, $R^2$ is not —$NH_2$.

In one embodiment, where $L^1$ and $L^2$ are a bond and $R^1$ is unsubstituted $C_1$ to $C_5$ alkyl (e.g. —$C(CH_3)(CH_3)$), $R^2$ is not —$NH_2$. In one embodiment, where $L^1$ and $L^2$ are a bond and $R^1$ is unsubstituted $C_1$-$C_3$ alkyl, $R^2$ is not —$NH_2$. In one embodiment, where $L^1$ and $L^2$ are a bond and $R^1$ is substituted or unsubstituted $C_1$-$C_3$ alkyl, $R^2$ is not —$NH_2$. In one embodiment, where $L^1$ and $L^2$ are a bond and $R^1$ is substituted or unsubstituted $C_1$ to $C_5$ alkyl, $R^2$ is not —$NH_2$.

In one embodiment, where $L^1$ and $L^2$ are a bond and $R^1$ is phenyl, $R^2$ is not —$NH_2$. In one embodiment, where $L^1$ and $L^2$ are a bond and $R^1$ is substituted or unsubstituted phenyl, $R^2$ is not —$NH_2$. In one embodiment, where $L^1$ and $L^2$ are a bond and $R^1$ is substituted or unsubstituted 6 membered aryl, $R^2$ is not —$NH_2$. In one embodiment, where $L^1$ and $L^2$ are a bond and $R^1$ is 5 to 8 membered substituted or unsubstituted aryl, $R^2$ is not —$NH_2$.

In one embodiment, where $L^1$ and $L^2$ are a bond and $R^{1A}$ and $R^{1B}$ are both hydrogen, $R^{2A}$ and $R^{2B}$ are not both methyl. In one embodiment, where $L^1$ and $L^2$ are a bond and $R^{1A}$ and $R^{1B}$ are both hydrogen, $R^{2A}$ and $R^{2B}$ are not both unsubstituted $C_1$-$C_3$ alkyl. In one embodiment, where $L^1$ and $L^2$ are a bond and $R^{1A}$ and $R^{1B}$ are both hydrogen, $R^{2A}$ and $R^{2B}$ are not both substituted or unsubstituted $C_1$-$C_3$ alkyl. In one embodiment, where $L^1$ and $L^2$ are a bond and $R^{1A}$ and $R^{1B}$ are both hydrogen, $R^{2A}$ and $R^{2B}$ are not both substituted or ununsubstituted $C_1$-$C_5$ alkyl.

In one embodiment, where $L^1$ and $L^2$ are a bond and $R^1$ is 2'- or 3'-pyridinyl, $R^2$ is not $NH_2$. In one embodiment, where $L^1$ and $L^2$ are a bond and $R^1$ is unsubstituted or substituted 2'- or 3'-pyridinyl, $R^2$ is not —$NH_2$. In one embodiment, where $L^1$ and $L^2$ are a bond and $R^1$ is substituted or unsubstituted pyridinyl, $R^2$ is not —$NH_2$. In one embodiment, where $L^1$ and $L^2$ are a bond and $R^1$ is substituted or unsubstituted 3 to 7 membered heteroaryl, $R^2$ is not —$NH_2$.

In one embodiment, where $L^1$ and $L^2$ are a bond and $R^{1A}$ and $R^{1B}$ are both methyl, $R^2$ is not morpholino. In one embodiment, where $L^1$ and $L^2$ are a bond and $R^{1A}$ and $R^{1B}$ are both methyl, $R^2$ is not unsubstituted morpholino. In one embodiment, where $L^1$ and $L^2$ are a bond and $R^{1A}$ and $R^{1B}$ are both methyl, $R^2$ is not substituted or unsubstituted morpholino. In one embodiment, where $L^1$ and $L^2$ are a bond and $R^{1A}$ and $R^{1B}$ are both methyl, $R^2$ is not 6 unsubstituted membered heterocycloalkyl. In one embodiment, where $L^1$ and $L^2$ are a bond and $R^{1A}$ and $R^{1B}$ are both methyl, $R^2$ is not substituted or unsubstituted 6 membered heterocycloalkyl.

$L^1$ may be a bond. $L^2$ may be bond. $L^1$ and $L^2$ may be a bond. When $L^1$ is a bond, $L^2$ may be —NH—C(NH)—. When $L^1$ is —NH—C(NH)—, $L^2$ may be a bond. $L^1$ and $L^2$ may be —NH—C(NH)—. The compound of formula (I) may be a pharmaceutically salt thereof. Where $L^1$ or $L^2$ are —NH—C(NH)—, the carbon of the —NH—C(NH)— may be directly bound to $R^1$ or $R^2$ and the —NH— portion may be directly bound to the remainder of the molecule.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl.

$R^1$ may independently be $R^{1i}$-substituted or unsubstituted alkyl (e.g. $C_1$ to $C_8$ alkyl), $R^{1i}$-substituted or unsubstituted heteroalkyl (e.g. 2 to 8 membered heteroalkyl), $R^{1i}$-substituted or unsubstituted cycloalkyl (e.g. $C_3$-$C_8$ cycloalkyl), $R^{1i}$-substituted or unsubstituted heterocycloalkyl (e.g. 3 to 6 membered heterocycloalkyl), $R^{1i}$ substituted or unsubstituted aryl (e.g. phenyl), or $R^{1i}$-substituted or unsubstituted heteroaryl (e.g. 5 or 6 membered heteroaryl).

$R^{1i}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{1ii}$-substituted or unsubstituted alkyl (e.g. $C_1$ to $C_8$ alkyl), $R^{1ii}$-substituted or unsubstituted heteroalkyl (e.g. 2 to 8 membered heteroalkyl), $R^{1ii}$-substituted or unsubstituted cycloalkyl (e.g. $C_3$-$C_8$ cycloalkyl), $R^{1ii}$-substituted or unsubstituted heterocycloalkyl (e.g. 3 to 6 membered heterocycloalkyl), $R^{1ii}$-substituted or unsubstituted aryl (e.g. phenyl), or $R^{1ii}$-substituted or unsubstituted heteroaryl (e.g. 5 or 6 membered heteroaryl).

$R^{1ii}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

$R^1$ may be substituted or unsubstituted $C_1$-$C_{20}$ alkyl. $R^1$ may be unsubstituted $C_1$-$C_{20}$ alkyl. $R^1$ may be substituted $C_1$-$C_{20}$ alkyl. $R^1$ may be substituted or unsubstituted 2 to 20 membered heteroalkyl. $R^1$ may be unsubstituted 2 to 20 membered heteroalkyl. $R^1$ may be substituted 2 to 20 membered heteroalkyl. $R^1$ may be substituted or unsubstituted $C_1$-$C_8$ alkyl. $R^1$ may be unsubstituted $C_1$-$C_8$ alkyl. $R^1$ may be substituted $C_1$-$C_8$ alkyl. $R^1$ may be substituted or unsubstituted 2 to 8 membered heteroalkyl. $R^1$ may be unsubstituted 2 to 8 membered heteroalkyl. $R^1$ may be substituted 2 to 8 membered heteroalkyl. $R^1$ may be substituted or unsubstituted $C_1$-$C_4$ alkyl. $R^1$ may be unsubstituted $C_1$-$C_4$ alkyl. $R^1$ may be substituted $C_1$-$C_4$ alkyl. $R^1$ may be substituted or unsubstituted 2 to 4 membered heteroalkyl. $R^1$ may be unsubstituted 2 to 4 membered heteroalkyl. $R^1$ may be substituted 2 to 4 membered heteroalkyl.

$R^1$ may be substituted or unsubstituted 2 to 20 membered cycloalkyl. $R^1$ may be unsubstituted 2 to 20 membered cycloalkyl. $R^1$ may be substituted 2 to 20 membered cycloalkyl. $R^1$ may be substituted or unsubstituted 2 to 20 membered heterocycloalkyl. $R^1$ may be unsubstituted 2 to 20 membered heterocycloalkyl. $R^1$ may be substituted 2 to 20 membered heterocycloalkyl. $R^1$ may be substituted or unsubstituted 2 to 8 membered cycloalkyl. $R^1$ may be unsubstituted 2 to 8 membered cycloalkyl. $R^1$ may be substituted 2 to 8 membered cycloalkyl. $R^1$ may be substituted or unsubstituted 2 to 8 membered heterocycloalkyl. $R^1$ may be unsubstituted 2 to 8 membered heterocycloalkyl. $R^1$ may be substituted 2 to 8 membered heterocycloalkyl.

$R^1$ may be substituted or unsubstituted 5 to 20 membered aryl. $R^1$ may be substituted 5 to 20 membered aryl. $R^1$ may be substituted 5 to 20 membered aryl. $R^1$ may be substituted or unsubstituted 5 to 20 membered heteroaryl. $R^1$ may be unsubstituted 5 to 20 membered heteroaryl. $R^1$ may be substituted 5 to 20 membered heteroaryl. $R^1$ may be substituted or unsubstituted 5 to 8 membered aryl. $R^1$ may be unsubstituted 5 to 8 membered aryl. $R^1$ may be substituted 5 to 8 membered aryl. $R^1$ may be substituted or unsubstituted 5 to 8 membered heteroaryl. $R^1$ may be unsubstituted 5 to 8 membered heteroaryl. $R^1$ may be substituted 5 to 8 membered heteroaryl.

$R^1$ may be —$NR^{1A}R^{1B}$. $R^{1A}$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{1Ai}$-substituted or unsubstituted alkyl (e.g. $C_1$ to $C_8$ alkyl), $R^{1Ai}$-substituted or unsubstituted heteroalkyl (e.g. 2 to 8 membered heteroalkyl), $R^{Aii}$-substituted or unsubstituted cycloalkyl (e.g. $C_3$-$C_8$ cycloalkyl), $R^{1Ai}$-substituted or unsubstituted heterocycloalkyl (e.g. 3 to 6 membered heterocycloalkyl), $R^{1Ai}$-substituted or unsubstituted aryl (e.g. phenyl), or $R^{1Ai}$-substituted or unsubstituted heteroaryl (e.g. 5 or 6 membered heteroaryl).

$R^{1Ai}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{1Aii}$-substituted or unsubstituted alkyl (e.g. $C_1$ to $C_8$ alkyl), $R^{1Aii}$-substituted or unsubstituted heteroalkyl (e.g. 2 to 8 membered heteroalkyl), $R^{1Aii}$-substituted or unsubstituted cycloalkyl (e.g. $C_3$-$C_8$ cycloalkyl), $R^{1Aii}$-substituted or unsubstituted heterocycloalkyl (e.g. 3 to 6 membered heterocycloalkyl), $R^{1Aii}$-substituted or unsubstituted aryl (e.g. phenyl), or $R^{1Aii}$-substituted or unsubstituted heteroaryl (e.g. 5 or 6 membered heteroaryl).

$R^{1Aii}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl, unsubstituted aryl (e.g. phenyl), or unsubstituted heteroaryl (e.g. 5 or 6 membered heteroaryl).

$R^{1B}$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1B}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{1Bi}$-substituted or unsubstituted alkyl (e.g. $C_1$ to $C_8$ alkyl), $R^{1Bi}$-substituted or unsubstituted heteroalkyl (e.g. 2 to 8 membered heteroalkyl), $R^{1Bi}$-substituted or unsubstituted cycloalkyl (e.g. $C_3$-$C_8$ cycloalkyl), $R^{1Bi}$-substituted or unsubstituted heterocycloalkyl (e.g. 3 to 6 membered heterocycloalkyl), $R^{1Bi}$-substituted or unsubstituted aryl (e.g. phenyl), or $R^{1Bi}$-substituted or unsubstituted heteroaryl (e.g. 5 or 6 membered heteroaryl).

$R^{1Bi}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{1Bii}$-substituted or unsubstituted alkyl (e.g. $C_1$ to $C_8$ alkyl), $R^{1Bii}$-substituted or unsubstituted heteroalkyl (e.g. 2 to 8 membered heteroalkyl), $R^{1Bii}$-substituted or unsubstituted cycloalkyl (e.g. $C_3$-$C_8$ cycloalkyl), $R^{1Bii}$-substituted or unsubstituted heterocycloalkyl (e.g. 3 to 6 membered heterocycloalkyl), $R^{1Bii}$-substituted or unsubstituted aryl (e.g. phenyl), or $R^{1Bii}$-substituted or unsubstituted heteroaryl (e.g. 5 or 6 membered heteroaryl).

$R^{1Bii}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

In embodiments, $R^{1A}$ may be substituted or unsubstituted heteroalkyl or substituted or unsubstituted alkyl. $R^{1A}$ may be substituted or unsubstituted 2 to 6 membered heteroalkyl. $R^{1A}$ may be substituted 2 to 6 membered heteroalkyl. $R^{1A}$ may be unsubstituted 2 to 6 membered heteroalkyl. $R^{1A}$ may be OMe. $R^{1A}$ may be substituted or unsubstituted $C_1$-$C_{10}$ alkyl. $R^{1A}$ may be substituted or unsubstituted $C_1$-$C_5$ alkyl. $R^{1A}$ may be substituted or unsubstituted $C_1$-$C_3$ alkyl. $R^{1A}$ maybe be substituted $C_1$-$C_5$ alkyl. $R^{1A}$ may be unsubstituted $C_1$-$C_5$ alkyl. $R^{1A}$ may be methyl, ethyl, or propyl.

In embodiments, $R^{1B}$ may be substituted or unsubstituted heteroalkyl or substituted or unsubstituted alkyl. $R^{1B}$ may be substituted or unsubstituted 2 to 6 membered heteroalkyl. $R^{1B}$ may be substituted 2 to 6 membered heteroalkyl. $R^{1B}$ may be unsubstituted 2 to 6 membered heteroalkyl. $R^{1B}$ may be OMe. $R^{1B}$ may be substituted or unsubstituted $C_1$-$C_{10}$ alkyl. $R^{1B}$ may be substituted or unsubstituted $C_1$-$C_5$ alkyl. $R^{1B}$ may be substituted or unsubstituted $C_1$-$C_3$ alkyl. $R^{1B}$ maybe be substituted $C_1$-$C_5$ alkyl. $R^{1B}$ may be unsubstituted $C_1$-$C_5$ alkyl. $R^{1B}$ may be methyl, ethyl, or propyl. When $R^{1B}$ is unsubstituted $C_1$-$C_5$ alkyl, $R^{1A}$ may be substituted or unsubstituted heteroalkyl or substituted or unsubstituted alkyl. When $R^{1B}$ is unsubstituted alkyl, $R^{1A}$ may be substituted or unsubstituted heteroalkyl. $R^{1A}$ may be substituted or unsubstituted 3 to 6 membered heteroalkyl. $R^{1A}$ may be unsubstituted 3 to 6 membered heteroalkyl. When $R^{1B}$ is unsubstituted alkyl, $R^{1A}$ may be substituted or unsubstituted alkyl. $R^{1A}$ may be unsubstituted $C_1$-$C_5$ alkyl.

$R^{1A}$ may be substituted or unsubstituted cycloalkyl. $R^{1A}$ may be substituted or unsubstituted 3 to 8 membered cycloalkyl. $R^{1A}$ may be substituted 3 to 8 membered cycloalkyl. $R^{1A}$ may be substituted 5 or 6 membered cycloalkyl. $R^{1A}$ may be unsubstituted 3 to 8 membered cycloalkyl. $R^{1A}$ may be unsubstituted 5 or 6 membered cycloalkyl. $R^{1A}$ may be substituted or unsubstituted heterocycloalkyl. $R^{1A}$ may be substituted or unsubstituted 3 to 8 membered heterocycloalkyl. $R^{1A}$ may be substituted or unsubstituted 3, 5, or 6 membered heterocycloalkyl. $R^{1A}$ may be, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, substituted or unsubstituted tetrahydrothiophenyl, or substituted or unsubstituted tetrahydropyranyl.

$R^{1B}$ may be substituted or unsubstituted cycloalkyl. $R^{1B}$ may be substituted or unsubstituted 3 to 8 membered cycloalkyl. $R^{1B}$ may be substituted 3 to 8 membered cycloalkyl. $R^{1B}$ may be substituted 5 or 6 membered cycloalkyl. $R^{1B}$ may be unsubstituted 3 to 8 membered cycloalkyl. $R^{1B}$ may be unsubstituted 5 or 6 membered cycloalkyl. $R^{1B}$ may be substituted or unsubstituted heterocycloalkyl. $R^{1B}$ may be substituted or unsubstituted 3 to 8 membered heterocycloalkyl. $R^{1B}$ may be substituted or unsubstituted 3, 5, or 6 membered heterocycloalkyl. $R^{1B}$ may be, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, substituted or unsubstituted tetrahydrothiophenyl, or substituted or unsubstituted tetrahydropyranyl.

$R^{1A}$ may be substituted or unsubstituted aryl. $R^{1A}$ may be substituted or unsubstituted 5 to 8 membered aryl. $R^{1A}$ may be substituted 5 to 8 membered aryl. $R^{1A}$ may be substituted 5 or 6 membered aryl. $R^{1A}$ may be unsubstituted 5 to 8 membered aryl. $R^{1A}$ may be unsubstituted 5 or 6 membered aryl. $R^{1A}$ may be substituted or unsubstituted heteroaryl. $R^{1A}$ may be substituted or unsubstituted 5 to 8 membered heteroaryl. $R^{1A}$ may be substituted 5 to 8 membered heteroaryl. $R^{1A}$ may be substituted 5 or 6 membered aryl. $R^{1A}$ may be unsubstituted 5 to 8 membered heteroaryl. $R^{1A}$ may be unsubstituted 5 or 6 membered heteroaryl.

$R^{1B}$ may be substituted or unsubstituted aryl. $R^{1B}$ may be substituted or unsubstituted 5 to 8 membered aryl. $R^{1B}$ may be substituted 5 to 8 membered aryl. $R^{1B}$ may be substituted 5 or 6 membered aryl. $R^{1B}$ may be unsubstituted 5 to 8 membered aryl. $R^{1B}$ may be unsubstituted 5 or 6 membered aryl. $R^{1B}$ may be substituted or unsubstituted heteroaryl. $R^{1B}$ may be substituted or unsubstituted 5 to 8 membered heteroaryl. $R^{1B}$ may be substituted 5 to 8 membered heteroaryl. $R^{1B}$ may be substituted 5 or 6 membered aryl. $R^{1B}$ may be unsubstituted 5 to 8 membered heteroaryl. $R^{1B}$ may be unsubstituted 5 or 6 membered heteroaryl.

$R^{1A}$ and $R^{1B}$ may optionally be joined to form substituted or unsubstituted 3 to 8 membered heterocycloalkyl. $R^{1A}$ and $R^{1B}$ may optionally be joined to form substituted or unsubstituted 5 or 6 membered heterocycloalkyl.

The ring formed by joining $R^{1A}$ and $R^{1B}$ may be $R^5$-substituted or unsubstituted heterocycloalkyl. $R^5$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{5a}$-substituted or unsubstituted alkyl (e.g. $C_1$ to $C_8$ alkyl), $R^{5a}$-substituted or unsubstituted heteroalkyl (e.g. 2 to 8 membered heteroalkyl), $R^{5a}$-substituted or unsubstituted cycloalkyl (e.g. $C_3$-$C_8$ cycloalkyl), $R^{5a}$-substituted or unsubstituted heterocycloalkyl (e.g. 3 to 6 membered heterocycloalkyl), $R^{5a}$-substituted or unsubstituted aryl (e.g. phenyl), or $R^{5a}$-substituted or unsubstituted heteroaryl (e.g. 5 or 6 membered heteroaryl).

$R^{5a}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{5b}$-substituted or unsubstituted alkyl (e.g. $C_1$ to $C_8$ alkyl), $R^{5b}$-substituted or unsubstituted heteroalkyl (e.g. 2 to 8 membered heteroalkyl), $R^{5b}$-substituted or unsubstituted cycloalkyl (e.g. $C_3$-$C_8$ cycloalkyl), $R^{5b}$-substituted or unsubstituted heterocycloalkyl (e.g. 3 to 6 membered heterocycloalkyl), $R^{5b}$-substituted or unsubstituted aryl (e.g. phenyl), or $R^{5b}$-substituted or unsubstituted heteroaryl (e.g. 5 or 6 membered heteroaryl).

$R^{5B}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

$R^{1A}$ and $R^{1B}$ may optionally be joined to form, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, substituted or unsubstituted tetrahydrothiophenyl, or substituted or unsubstituted tetrahydropyranyl.

$R^{1A}$ and $R^{1B}$ may optionally be joined to form, $R^5$-substituted or unsubstituted pyrrolidinyl, $R^5$-substituted or unsubstituted imidazolidinyl, $R^5$-substituted or unsubstituted oxazolidinyl, $R^5$-substituted or unsubstituted thiazolidinyl, $R^5$-substituted or unsubstituted dioxolanyl, $R^5$-substituted or unsubstituted dithiolanyl, $R^5$-substituted or unsubstituted piperidinyl, $R^5$-substituted or unsubstituted morpholinyl, $R^5$-substituted or unsubstituted dioxanyl, $R^5$-substituted or unsubstituted dithianyl, $R^5$-substituted or unsubstituted aziridinyl, $R^5$-substituted or unsubstituted azetidinyl, $R^5$-substituted or unsubstituted azepinyl, $R^5$-substituted or unsubstituted oxiranyl, $R^5$-substituted or unsubstituted oxetanyl, $R^5$-substituted or unsubstituted tetrahydrofuranyl, $R^5$-substituted or unsubstituted tetrahydropyranyl, or $R^5$-substituted or unsubstituted tetrahydrothiophenyl. $R^5$ is as described herein, including embodiments thereof.

$R^2$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{2i}$-substituted or unsubstituted alkyl (e.g. $C_1$ to $C_8$ alkyl), $R^{2i}$-substituted or unsubstituted heteroalkyl (e.g. 2 to 8 membered heteroalkyl), $R^{2i}$-substituted or unsubstituted cycloalkyl (e.g. $C_3$-$C_8$ cycloalkyl), $R^{2i}$-substituted or unsubstituted heterocycloalkyl (e.g. 3 to 6 membered heterocycloalkyl), $R^{2i}$-substituted or unsubstituted aryl (e.g. phenyl), or $R^{2i}$-substituted or unsubstituted heteroaryl (e.g. 5 or 6 membered heteroaryl).

$R^{2i}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, $R^{2ii}$-substituted or unsubstituted alkyl (e.g. $C_1$ to $C_8$ alkyl), $R^{2ii}$-substituted or unsubstituted heteroalkyl (e.g. 2 to 8 membered heteroalkyl), $R^{2ii}$-substituted or unsubstituted cycloalkyl (e.g. $C_3$-$C_8$ cycloalkyl), $R^{2ii}$-substituted or unsubstituted heterocycloalkyl (e.g. 3 to 6 membered heterocycloalkyl), $R^{2ii}$-substituted or unsubstituted aryl (e.g. phenyl), or $R^{2ii}$-substituted or unsubstituted heteroaryl (e.g. 5 or 6 membered heteroaryl).

$R^{2ii}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —$NHC(O)NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted ar aryl (e.g. phenyl)yl, or unsubstituted heteroaryl (e.g. 5 or 6 membered heteroaryl).

$R^2$ may be substituted or unsubstituted $C_1$-$C_{20}$ alkyl. $R^2$ may be unsubstituted $C_1$-$C_{20}$ alkyl. $R^2$ may be substituted $C_1$-$C_{20}$ alkyl. $R^2$ may be substituted or unsubstituted 2 to 20 membered heteroalkyl. $R^2$ may be unsubstituted 2 to 20 membered heteroalkyl. $R^2$ may be substituted 2 to 20 membered heteroalkyl. $R^2$ may be substituted or unsubstituted $C_1$-$C_8$ alkyl. $R^2$ may be unsubstituted $C_1$-$C_8$ alkyl. $R^2$ may be substituted $C_1$-$C_8$ alkyl. $R^2$ may be substituted or unsubstituted 2 to 8 membered heteroalkyl. $R^2$ may be unsubstituted 2 to 8 membered heteroalkyl. $R^2$ may be substituted 2 to 8 membered heteroalkyl. $R^2$ may be substituted or unsubstituted $C_1$-$C_4$ alkyl. $R^2$ may be unsubstituted $C_1$-$C_4$ alkyl. $R^2$ may be substituted $C_1$-$C_4$ alkyl. $R^2$ may be substituted or unsubstituted 2 to 4 membered heteroalkyl. $R^2$ may be unsubstituted 2 to 4 membered heteroalkyl. $R^2$ may be substituted 2 to 4 membered heteroalkyl.

$R^2$ may be substituted or unsubstituted 2 to 20 membered cycloalkyl. $R^2$ may be unsubstituted 2 to 20 membered cycloalkyl. $R^2$ may be substituted 2 to 20 membered cycloalkyl. $R^2$ may be substituted or unsubstituted 2 to 20 membered heterocycloalkyl. $R^2$ may be unsubstituted 2 to 20 membered heterocycloalkyl. $R^2$ may be substituted 2 to 20 membered heterocycloalkyl. $R^2$ may be substituted or unsubstituted 2 to 8 membered cycloalkyl. $R^2$ may be unsubstituted 2 to 8 membered cycloalkyl. $R^2$ may be substituted 2 to 8 membered cycloalkyl. $R^2$ may be substituted or unsubstituted 2 to 8 membered heterocycloalkyl. $R^2$ may be unsubstituted 2 to 8 membered heterocycloalkyl. $R^2$ may be substituted 2 to 8 membered heterocycloalkyl.

$R^2$ may be substituted or unsubstituted 5 to 20 membered aryl. $R^2$ may be unsubstituted 5 to 20 membered aryl. $R^2$ may be substituted 5 to 20 membered aryl. $R^2$ may be substituted or unsubstituted 5 to 20 membered heteroaryl. $R^2$ may be unsubstituted 5 to 20 membered heteroaryl. $R^2$ may be substituted 5 to 20 membered heteroaryl. $R^2$ may be substituted or unsubstituted 5 to 8 membered aryl. $R^2$ may be unsubstituted 5 to 8 membered aryl. $R^2$ may be substituted 5 to 8 membered aryl. $R^2$ may be substituted or unsubstituted 5 to 8 membered heteroaryl. $R^2$ may be unsubstituted 5 to 8 membered heteroaryl. $R^2$ may be substituted 5 to 8 membered heteroaryl.

$R^2$ may be —$NR^{2A}R^{2B}$. $R^{2A}$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, $R^{2Ai}$-substituted or unsubstituted alkyl (e.g. $C_1$ to $C_8$ alkyl), $R^{2Ai}$-substituted or unsubstituted heteroalkyl (e.g. 2 to 8 membered heteroalkyl), $R^{2Ai}$-substituted or unsubstituted cycloalkyl (e.g. $C_3$-$C_8$ cycloalkyl), $R^{2Ai}$-substituted or unsubstituted heterocycloalkyl (e.g. 3 to 6 membered heterocycloalkyl), $R^{2Ai}$-substituted or unsubstituted aryl (e.g. phenyl), or $R^{2Ai}$-substituted or unsubstituted heteroaryl (e.g. 5 or 6 membered heteroaryl).

$R^{2Ai}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, $R^{2Aii}$-substituted or unsubstituted alkyl (e.g. $C_1$ to $C_8$ alkyl), $R^{2Aii}$-substituted or unsubstituted heteroalkyl (e.g. 2 to 8 membered heteroalkyl), $R^{2Aii}$-substituted or unsubstituted cycloalkyl (e.g. $C_3$-$C_8$ cycloalkyl), $R^{2Aii}$-substituted or unsubstituted heterocycloalkyl (e.g. 3 to 6 membered heterocycloalkyl), $R^{2Aii}$-substituted or unsubstituted aryl (e.g. phenyl), or $R^{2Aii}$-substituted or unsubstituted heteroaryl (e.g. 5 or 6 membered heteroaryl).

$R^{2Aii}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

$R^{2B}$ may be hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2B}$ may independently be hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, $R^{2Bi}$-substituted or unsubstituted alkyl (e.g. $C_1$ to $C_8$ alkyl), $R^{2Bi}$-substituted or unsubstituted heteroalkyl (e.g. 2 to 8 membered heteroalkyl), $R^{2Bi}$-substituted or unsubstituted cycloalkyl (e.g. $C_3$-$C_8$ cycloalkyl), $R^{2Bi}$-substituted or unsubstituted heterocycloalkyl (e.g. 3 to 6 membered heterocycloalkyl), $R^{2Bi}$-substituted or unsubstituted aryl (e.g. phenyl), or $R^{2Bi}$-substituted or unsubstituted heteroaryl (e.g. 5 or 6 membered heteroaryl).

$R^{2Bi}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, $R^{2Bii}$-substituted or unsubstituted alkyl (e.g. $C_1$ to $C_8$ alkyl), $R^{2Bii}$-substituted or unsubstituted heteroalkyl (e.g. 2 to 8 membered heteroalkyl), $R^{2Bii}$-substituted or unsubstituted cycloalkyl (e.g. $C_3$-$C_8$ cycloalkyl), $R^{2Bii}$-substituted or unsubstituted heterocycloalkyl (e.g. 3 to 6 membered heterocycloalkyl), $R^{2Bii}$-substituted or unsubstituted aryl (e.g. phenyl), or $R^{2Bii}$-substituted or unsubstituted heteroaryl (e.g. 5 or 6 membered heteroaryl).

$R^{2Bii}$ is independently hydrogen, halogen, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2$, —$SO_2Cl$, —$SO_3H$, —$SO_4H$, —$SO_2NH_2$, —$NHNH_2$, —$ONH_2$, —NHC(O)$NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

In embodiments, $R^{2A}$ may be substituted or unsubstituted heteroalkyl or substituted or unsubstituted alkyl. $R^{2A}$ may be substituted or unsubstituted 2 to 6 membered heteroalkyl. $R^{2A}$ may be substituted 2 to 6 membered heteroalkyl. $R^{2A}$ may be unsubstituted 2 to 6 membered heteroalkyl. $R^{2A}$ may be —$OCH_3$. $R^{2A}$ may be substituted or unsubstituted $C_1$-$C_{10}$ alkyl. $R^{2A}$ may be substituted or unsubstituted $C_1$-$C_5$ alkyl. $R^{2A}$ may be substituted or unsubstituted $C_1$-$C_3$ alkyl. $R^{2A}$ maybe be substituted $C_1$-$C_5$ alkyl. $R^{2A}$ may be unsubstituted $C_1$-$C_5$ alkyl. $R^{2A}$ may be methyl, ethyl, or propyl.

In embodiments, $R^{2B}$ may be substituted or unsubstituted heteroalkyl or substituted or unsubstituted alkyl. $R^{2B}$ may be substituted or unsubstituted 2 to 6 membered heteroalkyl. $R^{2B}$ may be substituted 2 to 6 membered heteroalkyl. $R^{2B}$ may be unsubstituted 2 to 6 membered heteroalkyl. $R^{2B}$ may be OMe. $R^{2B}$ may be substituted or unsubstituted $C_1$-$C_{10}$ alkyl. $R^{2B}$ may be substituted or unsubstituted $C_1$-$C_5$ alkyl. $R^{2B}$ may be substituted or unsubstituted $C_1$-$C_3$ alkyl. $R^{2B}$ maybe be substituted $C_1$-$C_5$ alkyl. $R^{2B}$ may be unsubstituted $C_1$-$C_5$ alkyl. $R^{2B}$ may be methyl (also referred to herein as "Me"), ethyl, or propyl. When $R^{2B}$ is unsubstituted $C_1$-$C_5$ alkyl, $R^{2A}$ may be substituted or unsubstituted heteroalkyl or substituted or unsubstituted alkyl. When $R^{2B}$ is unsubstituted alkyl, $R^{2A}$ may be substituted or unsubstituted heteroalkyl. $R^{2A}$ may be substituted or unsubstituted 3 to 6 membered heteroalkyl. $R^{2A}$ may be unsubstituted 3 to 6 membered heteroalkyl. When $R^{2B}$ is unsubstituted alkyl, $R^{2A}$ may be substituted or unsubstituted alkyl. $R^{2A}$ may be unsubstituted $C_1$-$C_5$ alkyl.

$R^{2A}$ may be substituted or unsubstituted cycloalkyl. $R^{2A}$ may be substituted or unsubstituted 3 to 8 membered cycloalkyl. $R^{2A}$ may be substituted 3 to 8 membered cycloalkyl. $R^{2A}$ may be substituted 5 or 6 membered cycloalkyl. $R^{2A}$ may be unsubstituted 3 to 8 membered cycloalkyl. $R^{2A}$ may be unsubstituted 5 or 6 membered cycloalkyl. $R^{2A}$ may be substituted or unsubstituted heterocycloalkyl. $R^{2A}$ may be substituted or unsubstituted 3 to 8 membered heterocycloalkyl. $R^{2A}$ may be, for example, substituted or unsubstituted 3, 5, or 6 membered heterocycloalkyl. $R^{2A}$ may be substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, substituted or unsubstituted tetrahydrothiophenyl, or substituted or unsubstituted tetrahydropyranyl.

$R^{2B}$ may be substituted or unsubstituted cycloalkyl. $R^{2B}$ may be substituted or unsubstituted 3 to 8 membered cycloalkyl. $R^{2B}$ may be substituted 3 to 8 membered cycloalkyl. $R^{2B}$ may be substituted 5 or 6 membered cycloalkyl. $R^{2B}$ may be unsubstituted 3 to 8 membered cycloalkyl. $R^{2B}$ may be unsubstituted 5 or 6 membered cycloalkyl. $R^{2B}$ may be substituted or unsubstituted heterocycloalkyl. $R^{2B}$ may be substituted or unsubstituted 3 to 8 membered heterocycloalkyl. $R^{2B}$ may be substituted or unsubstituted 3, 5, or 6 membered heterocycloalkyl. $R^{2B}$ may be, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, substituted or unsubstituted tetrahydrothiophenyl, or substituted or unsubstituted tetrahydropyranyl.

$R^{2A}$ may be substituted or unsubstituted aryl. $R^{2A}$ may be substituted or unsubstituted 5 to 8 membered aryl. $R^{2A}$ may be substituted 5 to 8 membered aryl. $R^{2A}$ may be substituted 5 or 6 membered aryl. $R^{2A}$ may be unsubstituted 5 to 8 membered aryl. $R^{2A}$ may be unsubstituted 5 or 6 membered aryl. $R^{2A}$ may be substituted or unsubstituted heteroaryl. $R^{2A}$ may be substituted or unsubstituted 5 to 8 membered heteroaryl. $R^{2A}$ may be substituted 5 to 8 membered heteroaryl. $R^{2A}$ may be substituted 5 or 6 membered aryl. $R^{2A}$ may be unsubstituted 5 to 8 membered heteroaryl. $R^{2A}$ may be unsubstituted 5 or 6 membered heteroaryl.

$R^{2B}$ may be substituted or unsubstituted aryl. $R^{2B}$ may be substituted or unsubstituted 5 to 8 membered aryl. $R^{2B}$ may be substituted 5 to 8 membered aryl. $R^{2B}$ may be substituted 5 or 6 membered aryl. $R^{2B}$ may be unsubstituted 5 to 8 membered aryl. $R^{2B}$ may be unsubstituted 5 or 6 membered aryl. $R^{2B}$ may be substituted or unsubstituted heteroaryl. $R^{2B}$ may be substituted or unsubstituted 5 to 8 membered heteroaryl. $R^{2B}$ may be substituted 5 to 8 membered heteroaryl. $R^{2B}$ may be substituted 5 or 6 membered aryl. $R^{2B}$ may be unsubstituted 5 to 8 membered heteroaryl. $R^{2B}$ may be unsubstituted 5 or 6 membered heteroaryl.

$R^{2A}$ and $R^{2B}$ may optionally be joined to form substituted or unsubstituted 3 to 8 membered heterocycloalkyl. $R^{2A}$ and $R^{2B}$ may optionally be joined to form substituted or unsubstituted 5 or 6 membered heterocycloalkyl.

The ring formed by joining $R^{2A}$ and $R^{2B}$ may be $R^6$-substituted or unsubstituted cycloalkyl. $R^6$ may independently be hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, $R^{6a}$-substituted or unsubstituted alkyl (e.g. $C_1$ to $C_8$ alkyl), $R^{6a}$-substituted or unsubstituted heteroalkyl (e.g. 2 to 8 membered heteroalkyl), $R^{6a}$-substituted or unsubstituted cycloalkyl (e.g. $C_3$-$C_8$ cycloalkyl), $R^{6a}$-substituted or unsubstituted heterocycloalkyl (e.g. 3 to 6 membered heterocycloalkyl), $R^{6a}$-substituted or unsubstituted aryl (e.g. phenyl), or $R^{6a}$-substituted or unsubstituted heteroaryl (e.g. 5 or 6 membered heteroaryl).

$R^{6a}$ is independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, $R^{6b}$-substituted or unsubstituted alkyl (e.g. $C_1$ to $C_8$ alkyl), $R^{6b}$-substituted or unsubstituted heteroalkyl (e.g. 2 to 8 membered heteroalkyl), $R^{6b}$-substituted or unsubstituted cycloalkyl (e.g. $C_3$-$C_8$ cycloalkyl), $R^{6b}$-substituted or unsubstituted heterocycloalkyl (e.g. 3 to 6 membered heterocycloalkyl), $R^{6b}$-substituted or unsubstituted aryl (e.g. phenyl), or $R^{6b}$-substituted or unsubstituted heteroaryl (e.g. 5 or 6 membered heteroaryl).

$R^{6b}$ is independently hydrogen, halogen, $-N_3$, $-CF_3$, $-CCl_3$, $-CBr_3$, $-CI_3$, $-CN$, $-CHO$, $-OH$, $-NH_2$, $-COOH$, $-CONH_2$, $-NO_2$, $-SH$, $-SO_2$, $-SO_2Cl$, $-SO_3H$, $-SO_4H$, $-SO_2NH_2$, $-NHNH_2$, $-ONH_2$, $-NHC(O)NHNH_2$, unsubstituted alkyl (e.g. $C_1$ to $C_8$ alkyl), unsubstituted heteroalkyl (e.g. 2 to 8 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

$R^{2A}$ and $R^{2B}$ may optionally be joined to form, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, substituted or unsubstituted tetrahydrothiophenyl, or substituted or unsubstituted tetrahydropyranyl.

$R^{2A}$ and $R^{2B}$ may optionally be joined to form, $R^6$-substituted or unsubstituted pyrrolidinyl, $R^6$-substituted or unsubstituted imidazolidinyl, $R^6$-substituted or unsubstituted oxazolidinyl, $R^6$-substituted or unsubstituted thiazolidinyl, $R^6$-substituted or unsubstituted dioxolanyl, $R^6$-substituted or unsubstituted dithiolanyl, $R^6$-substituted or unsubstituted piperidinyl, $R^6$-substituted or unsubstituted morpholinyl, $R^6$-substituted or unsubstituted dioxanyl, $R^6$-substituted or unsubstituted dithianyl, $R^6$-substituted or unsubstituted aziridinyl, $R^6$-substituted or unsubstituted azetidinyl, $R^6$-substituted or unsubstituted azepinyl, $R^6$-substituted or unsubstituted oxiranyl, $R^6$-substituted or unsubstituted oxetanyl, $R^6$-substituted or unsubstituted tetrahydrofuranyl, or $R^6$-substituted or unsubstituted tetrahydropyranyl or $R^6$-substituted or unsubstituted tetrahydrothiophenyl. $R^6$ is as described herein, including embodiments thereof.

In embodiments, $R^1$ is $-NR^{1A}R^{1B}$ and $R^2$ is $-NR^{2A}R^{2B}$. $R^{1A}$ may be substituted or unsubstituted heteroalkyl or substituted or unsubstituted alkyl and $R^{1B}$ may be substituted or unsubstituted alkyl. $R^{2A}$ and $R^{2B}$ may be hydrogen or substituted or unsubstituted alkyl. $R^{2A}$ and $R^{2B}$ may be hydrogen. In embodiments, the compound of formula (I) has formula:

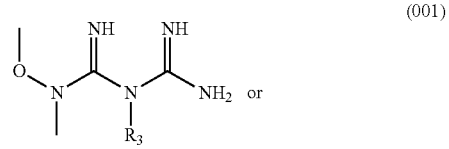

(001)

(008)

[Chemical structure: guanidine compound with NH, NH, N-methyl, N-propyl, R₃, NH₂ groups]

and pharmaceutically acceptable salts thereof.

When R¹ is —NR^{1A}R^{1B}, R² may be substituted or unsubstituted heteroalkyl. R² may be substituted 5 to 8 membered heteroalkyl. R² may be unsubstituted 5 to 8 membered heteroalkyl.

In embodiments, R¹ is —NR^{1A}R^{1B} and R^{1A} and R^{1B} are joined together to form a substituted or unsubstituted 3 to 8 membered heterocycloalkyl and R² is —NR^{2A}R^{2B}. R^{1A} and R^{1B} may be joined together to form a substituted or unsubstituted 5 or 6 membered heterocycloalkyl. R^{1A} and R^{1B} may be joined to form, for example, a substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted tetrahydrofuranyl, or substituted or unsubstituted tetrahydrothiophenyl, substituted or unsubstituted piperidinyl, substituted or unsubstituted morpholinyl, substituted or unsubstituted dioxanyl, substituted or unsubstituted tetrahydropyranyl, or substituted or unsubstituted dithianyl. R^{2A} and R^{2B} may be hydrogen or substituted or unsubstituted alkyl. R^{2A} and R^{2B} may be hydrogen or methyl. The compound of formula (I) may have formula:

(II)

[Chemical structure showing ring A with (R⁵)_{z1} substituents connected to biguanide with R₃, R^{2a}, R^{2b}]

and pharmaceutically acceptable salts thereof.
Ring A is substituted or unsubstituted 3 to 8 membered heterocycloalkyl. The symbol z1 is an integer from 2 to 7. A person having ordinary skill in the art will understand that the value of z1 will depend upon the size of Ring A (e.g. where ring A is a 5 membered heterocycloalkyl, z1 will have a maximum value of 4). R⁵ is hydrogen, halogen, —N₃, —NO₂, —CF₃, —CCl₃, —CBr₃, —CI₃, —CN, —OH, —NH₂, —COOH, CONH₂, —NO₂, —SH, —SO₂Cl, —SO₃H, —SO₄H, —SO₂NH₂, —NHNH₂, —ONH₂, —NHC=(O)NHNH₂; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.

The compound of formula (II) may have formula:

(IIa)

[Chemical structure: piperidine ring with (R⁵)_{z1}, connected to biguanide with R₃, R^{5a}, R^{5b}]

or (IIb)

[Chemical structure: aziridine ring with (R⁵)_{z1}, connected to biguanide with R^{5a}, R^{5b}]

and pharmaceutically acceptable salts thereof.

The compound of formula (IIa) may have formula:

(015)

[Chemical structure: 4-methylpiperidinyl connected to biguanide with R₃ and N(CH₃)₂]

or (018)

[Chemical structure: 4,4-dimethylpiperidinyl connected to biguanide with R₃ and NH₂]

and pharmaceutically acceptable salts thereof.

The compound of formula (IIa) may have formula:

(015a)

[Chemical structure: 4-methylpiperidinyl connected to biguanide with NH and N(CH₃)₂]

or (018a)

[Chemical structure: 4,4-dimethylpiperidinyl connected to biguanide with NH and NH₂]

and pharmaceutically acceptable salts thereof.

The compound of formula (IIb) may have formula:

(019)

[Chemical structure: aziridinyl connected to biguanide with R₃ and NH₂]

or

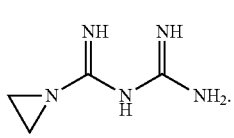

(019a)

In embodiments, $R^1$ is —$NR^{1A}R^{1B}$ and $R^{1A}$ and $R^{1B}$ are joined together to form a substituted or unsubstituted 3 to 8 membered heterocycloalkyl and $R^2$ is —$NR^{2A}R^{2B}$ and $R^{2A}$ and $R^{2B}$ are joined together to form a substituted or unsubstituted 3 to 8 membered heterocycloalkyl. $R^{1A}$ and $R^{1B}$ may be joined together to form a substituted or unsubstituted 5 or 6 membered heterocycloalkyl. $R^{2A}$ and $R^{2B}$ may be joined together to form a substituted or unsubstituted 5 or 6 membered heterocycloalkyl. $R^{1A}$ and $R^{1B}$ may be joined to form, for example, a substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted tetrahydrofuranyl, or substituted or unsubstituted tetrahydrothiophenyl, substituted or unsubstituted piperidinyl, substituted or unsubstituted morpholinyl, substituted or unsubstituted dioxanyl, substituted or unsubstituted tetrahydropyranyl, or substituted or unsubstituted dithianyl. $R^{2A}$ and $R^{2B}$ may be joined to form a joined to form a substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted tetrahydrofuranyl, or substituted or unsubstituted tetrahydrothiophenyl, substituted or unsubstituted piperidinyl, substituted or unsubstituted morpholinyl, substituted or unsubstituted dioxanyl, substituted or unsubstituted tetrahydropyranyl, or substituted or unsubstituted dithianyl. The compound of formula (I) may have formula:

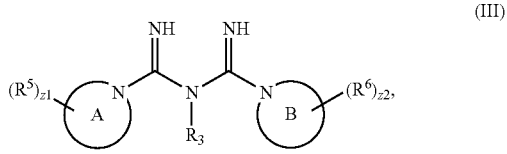

(III)

and pharmaceutically acceptable salts thereof.

Ring A and Ring B are independently substituted or unsubstituted 3 to 8 membered heterocycloalkyl. The symbol z1 is an integer from 2 to 7. The symbol z2 is an integer from 2 to 7. A person having ordinary skill in the art will understand that the value of z1 will depend upon the size of Ring A (e.g. where ring A is a 5 membered heterocycloalkyl, z1 will have a maximum value of 4). Likewise, a person having ordinary skill in the art will understand that the value of z2 will depend upon the size of Ring B (e.g. where ring B is a 5 membered heterocycloalkyl, z2 will have a maximum value of 4). $R^5$ and $R^6$ are independently hydrogen, halogen, —$N_3$, —$NO_2$, —$CF_3$, —$CCl_3$, —$CBr_3$, —$CI_3$, —CN, —OH, —$NH_2$, —COOH, $CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.

Ring A and Ring B may be identical. Ring A may be different than Ring B. Ring A may be a 5 membered heterocycloalkyl and ring B may be a 6 membered heterocycloalkyl. Ring A may, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted tetrahydrofuranyl, or substituted or unsubstituted tetrahydrothiophenyl and ring B may be, for example, substituted or unsubstituted piperidinyl, substituted or unsubstituted morpholinyl, substituted or unsubstituted dioxanyl, substituted or unsubstituted tetrahydropyranyl, or substituted or unsubstituted dithianyl. Ring A may be a 6 membered heterocycloalkyl and ring B may be a 5 membered heterocycloalkyl. Ring A may be, for example, substituted or unsubstituted piperidinyl, substituted or unsubstituted morpholinyl, substituted or unsubstituted dioxanyl, substituted or unsubstituted tetrahydropyranyl, or substituted or unsubstituted dithianyl and Ring B may be, for example, substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted tetrahydrofuranyl, or substituted or unsubstituted tetrahydrothiophenyl. Ring A and Ring B may be substituted as described herein, including embodiments thereof.

The compound of formula (III) may be have formula:

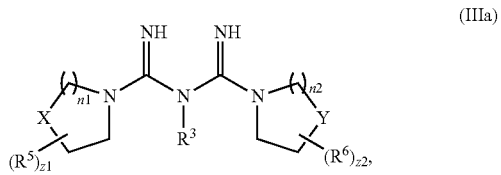

(IIIa)

and pharmaceutically acceptable salts thereof.

X is —$CH_2$—, —O—, or —NH—. Y is —$CH_2$—O—, or —NH—. The symbol n1 is an integer from 1 to 4. The symbol n2 is an integer from 1 to 4. A person having ordinary skill in the art will immediately understand that $R^5$ and $R^6$ may be attached to X and Y (e.g. wherein if X and Y are —NH—, or —$CH_2$—, respectively, the hydrogen for —NH— may be replaced with $R^5$ or $R^6$; or one or both of the hydrogens in —$CH_2$— may be replaced with $R^5$ or $R^6$).

The symbols n1 may be equal to n2. The symbols n1 and n2 may be 1. The symbols n1 and n2 may be 2. The symbols n1 and n2 may be 3. The symbols n1 and n2 may be 4. The symbol n2 may not equal n2. The symbol n1 may be 1 and n2 may be 2. The symbols n1 may be 1 and n2 may be 3. The symbols n1 may be 2 and n2 may be 1. The symbols n1 may be 2 and n2 may be 3.

The compound of formula (IIIa) may have formula:

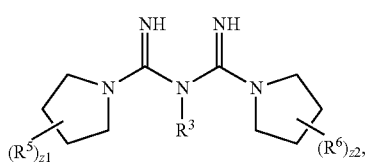
(IIIb)

and pharmaceutically acceptable salts thereof.

The compound of formula (IIIb) may have formula:

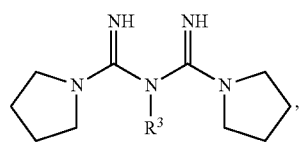
(006)

and pharmaceutically acceptable salts thereof.

The compound of formula (006) may have formula:

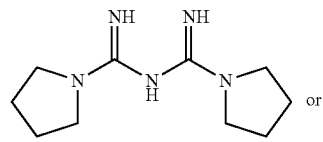
(006a)

or

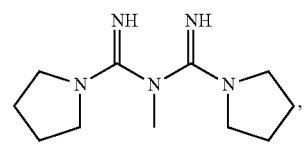
(006b)

and pharmaceutically acceptable salts thereof.

The compound of formula (IIIa) may have formula:

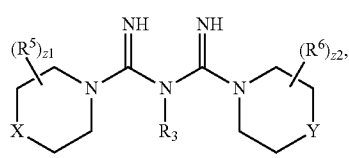
(IIIc)

and pharmaceutically acceptable salts thereof.

In certain embodiments X and Y are independently hydrogen, —O—, —NH—, or —CH$_2$—. In certain embodiments X and Y are both hydrogen, —O—, —NH—, or —CH$_2$—. A person having ordinary skill in the art will immediately understand that R$^5$ and R$^6$ may be attached to X and Y, respectively, where X and Y are —NH—, or —CH$_2$—, respectively (i.e. the hydrogen for —NH— may be replaced with R$^5$ or R$^6$; or one or both of the hydrogens in —CH$_2$— may be replaced with R$^5$ or R$^6$).

The compound of formula (IIIc) may have formula:

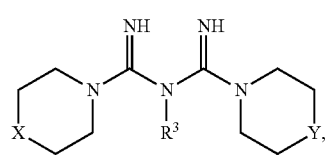
(IIId)

and pharmaceutically acceptable salts thereof.

The compound of formula (IIIc) may have formula:

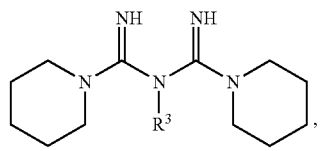
(002)

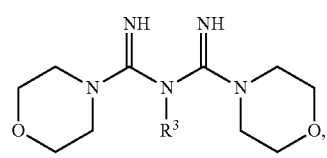
(003)

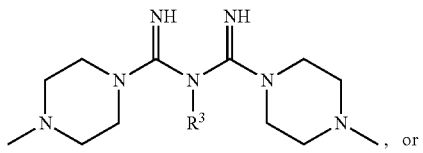
(004)

, or

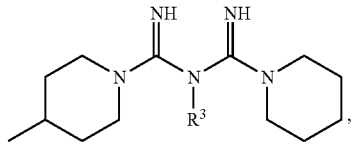
(016)

and pharmaceutically acceptable salts thereof.

The compound of formula (IIIc) may have formula:

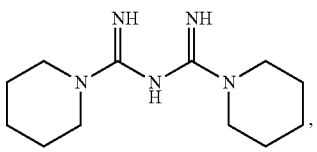
(002a)

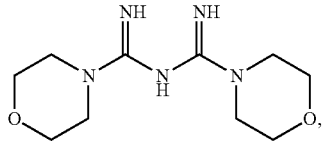
(003a)

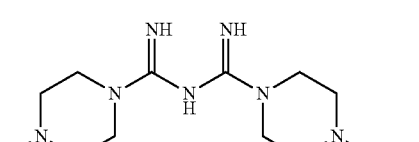
(004a)

, or

-continued (016a)

and pharmaceutically acceptable salts thereof.

The compound of formula (IIIc) may have formula:

(002b)

(003b)

(004b), or (016b)

and pharmaceutically acceptable salts thereof.

The compound of formula (IIIa) may have formula:

(IVa)

(VIb)

and pharmaceutically acceptable salts thereof. A person having ordinary skill in the art will immediately understand that $R^5$ and $R^6$ may be attached to X and Y (e.g wherein if X and Y are —NH—, or —CH$_2$—, respectively, the hydrogen for —NH— may be replaced with $R^5$ or $R^6$; or one or both of the hydrogens in —CH$_2$— may be replaced with $R^5$ or $R^6$).

The compound of formula (IVa) may have formula:

(017)

and pharmaceutically acceptable salts thereof.

The compound of formula (017) may have formula:

(017a)

, or (017b)

and pharmaceutically acceptable salts thereof.

The compound of formula (IVb) may have formula:

(005)

and pharmaceutically acceptable salts thereof.

The compound of formula (005) may have formula:

(005a)

or (005b)

and pharmaceutically acceptable salts thereof.

$R^1$ may be substituted or unsubstituted aryl or substituted or unsubstituted heteroaryl and $R^2$ may be —NR$^{2A}$R$^{2B}$. The compound of formula (I) may have:

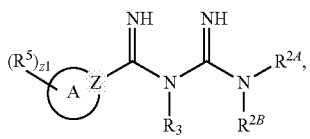

(V)

and pharmaceutically acceptable salts thereof.

Ring C is substituted or unsubstituted 5 to 8 membered aryl or substituted or unsubstituted 5 to 8 membered heteroaryl. Z is —C—, —O—, or —S—. $R^{2A}$, $R^{2B}$, $R^3$, $R^5$, and z1 are as described herein, including embodiments thereof.

$R^{2A}$ and $R^{2B}$ may independently be hydrogen, substituted or unsubstituted alkyl or substituted or unsubstituted alkyl, as described herein, including embodiments thereof. $R^{2A}$ and $R^{2B}$ may optionally be joined together to form a heterocycloalkyl as described herein, including embodiments thereof.

The compound of formula (V) may have formula:

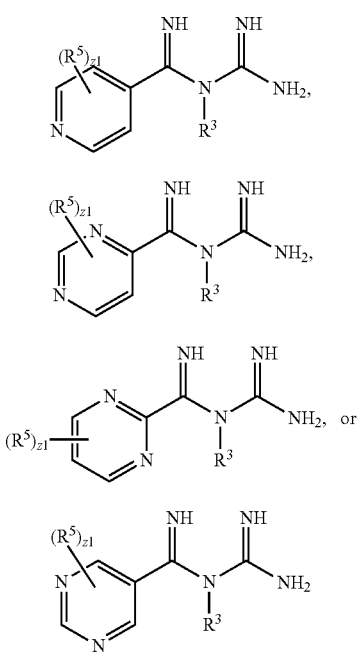

and pharmaceutically acceptable salts thereof.

The compound of formula (V) may have formula:

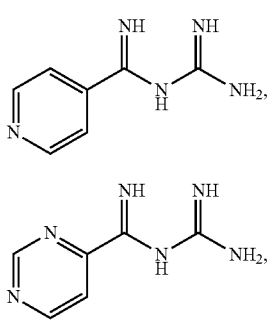

and pharmaceutically acceptable salts thereof.

The compound of formula (V) may have formula:

(020b)

(021b)

(022b)

(023b)

and pharmaceutically acceptable salts thereof.

In embodiments, $L^1$ of the compound of formula (I) is a bond and $L^2$ of the compound of formula (I) is —NH—C(NH)—. $L^1$ and $L^2$ of the compound of formula (I) may both be —NH—C(NH)—. $R^1$, $R^2$, $R^{1A}$, $R^{1B}$, $R^{2A}$ and $R^{2B}$ are as described herein, including embodiments thereof. When $L^1$ is a bond and $L^2$ is —NH—C(NH)—, $R^1$ and $R^2$ may independently be substituted or unsubstituted aryl, substituted or unsubstituted heteroaryl, or substituted or unsubstituted alkyl. When $L^1$ is a bond and $L^2$ is —NH—C(NH)—, $R^1$ and $R^2$ may independently be substituted or unsubstituted aryl. $R^1$ may be substituted or unsubstituted 5 to 8 membered aryl. $R^1$ may be substituted 5 to 8 membered aryl. $R^1$ may be unsubstituted 5 to 8 membered aryl. $R^1$ may be substituted or unsubstituted phenyl. $R^1$ may be substituted phenyl. $R^1$ may be unsubstituted phenyl. $R^2$ may be substituted or unsubstituted 5 to 8 membered aryl. $R^2$ may be substituted 5 to 8 membered aryl. $R^2$ may be unsubstituted 5 to 8 membered aryl. $R^2$ may be substituted or unsubstituted phenyl. $R^2$ may be substituted phenyl. $R^2$ may be unsubstituted phenyl.

When $L^1$ is a bond and $L^2$ is —NH—C(NH)—, $R^1$ and $R^2$ may independently be substituted or unsubstituted heteroaryl. $R^1$ may be substituted or unsubstituted 5 to 8 membered heteroaryl. $R^1$ may be substituted 5 to 8 membered heteroaryl. $R^1$ may be unsubstituted 5 to 8 membered heteroaryl. $R^1$ may be substituted or unsubstituted 4, 5, or 6 membered heteroaryl. $R^1$ may be, for example, substituted or unsubstituted pyridinyl, substituted or unsubstituted pyrrolyl, substituted or unsubstituted furanyl, substituted or unsubstituted thiophenyl, substituted or unsubstituted imidazlyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thirenyl.

$R^2$ may be substituted or unsubstituted 5 to 8 membered heteroaryl. $R^2$ may be substituted 5 to 8 membered heteroaryl. $R^2$ may be unsubstituted 5 to 8 membered heteroaryl. $R^2$ may be substituted or unsubstituted 4, 5, or 6 membered heteroaryl. $R^2$ may be, for example, substituted or unsubstituted pyridinyl, substituted or unsubstituted pyrrolyl, substituted or unsubstituted furanyl, substituted or unsubstituted thiophenyl, substituted or unsubstituted imidazlyl, substituted or unsubstituted pyrazolyl, substituted or unsubstituted oxazolyl, substituted or unsubstituted thiazolyl, substituted or unsubstituted pyranyl, substituted or unsubstituted thiopyranyl, substituted or unsubstituted pyrazinyl, substituted or unsubstituted pyrimindyl, substituted or unsubstituted pyridazinyl, substituted or unsubstituted oxazinyl, substituted or unsubstituted thiazinyl, substituted or unsubstituted doxinyl, substituted or unsubstituted dithiinyl, substituted or unsubstituted azetyl, substituted or unsubstituted oxetyl, substituted or unsubstituted thietyl, substituted or unsubstituted azirinyl, substituted or unsubstituted oxirenyl or substituted or unsubstituted thirenyl.

The compound of formula (I) may have formula:

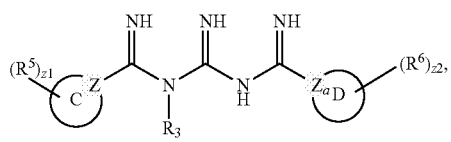

(VI)

and pharmaceutically acceptable salts thereof.

Ring D is substituted or unsubstituted 5 to 8 membered aryl or substituted or unsubstituted 5 to 8 membered heteroaryl. Za is —C—, —O—, or —S—. $R^3$, $R^5$, $R^6$, z1 and z2 are as described herein, including embodiments thereof.

The compound of formula (VI) may have formula:

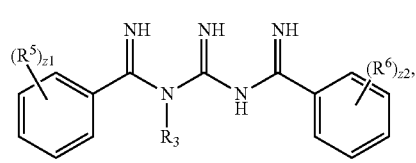

(010)

and pharmaceutically acceptable salts thereof.

The compound of formula (010) may have formula:

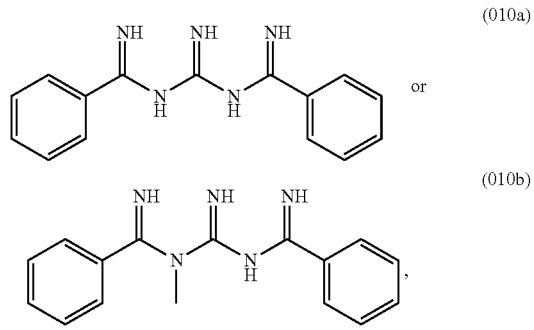

(010a)

or (010b)

and pharmaceutically acceptable salts thereof.

When $L^1$ is a bond and $L^2$ is —NH—C(NH)—, $R^1$ may be —NR$^{1A}$R$^{1B}$, substituted or unsubstituted alkyl or substituted or unsubstituted aryl or unsubstituted heteroaryl and $R^2$ may be substituted or unsubstituted alkyl or —NR$^{2A}$R$^{2B}$. $R^1$ may be a substituted or unsubstituted aryl or substituted or unsubstituted heteroaryl as described herein, including embodiments thereof. $R^2$ may be substituted or unsubstituted $C_1$-$C_5$ alkyl. $R^2$ may be methyl, ethyl, or propyl. $R^2$ may be methyl. When $R^2$ is —NR$^{2A}$R$^{2B}$, $R^{2A}$ and $R^{2B}$ may be hydrogen. The compound of formula (I) may have formula:

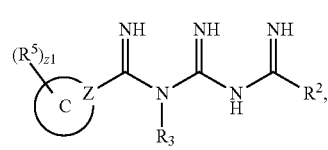

(VII)

and pharmaceutically acceptable salts thereof. Ring C, Z, z1, $R^2$, $R^3$, and $R^5$ are as described herein including embodiments thereof.

The compound of formula (VII) may have formula:

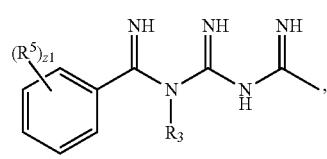

(011)

and pharmaceutically acceptable salts thereof.

The compound of formula (O11) may have formula:

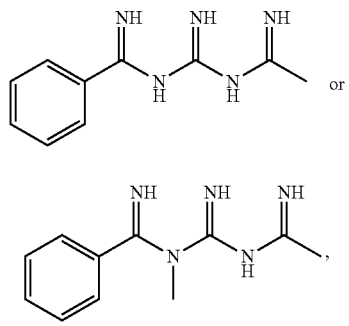

(O11a)

or (O11b)

and pharmaceutically acceptable salts thereof.

When $L^1$ is a bond and $L^2$ is —NH—C(NH)—, $R^1$ and $R^2$ may independently be substituted or unsubstituted alkyl. $R^1$ may be $C_1$-$C_{10}$ substituted or unsubstituted alkyl. $R^1$ may be substituted or unsubstituted $C_1$-$C_5$ alkyl. $R^1$ may be methyl. $R^1$ may be substituted or unsubstituted alkyl as described herein, including embodiments thereof. $R^2$ may be $C_1$-$C_{10}$ substituted or unsubstituted alkyl. $R^2$ may be substituted or unsubstituted $C_1$-$C_5$ alkyl. $R^2$ may be methyl. $R^2$ may be substituted or unsubstituted alkyl as described herein, including embodiments thereof. $R^1$ may be —$NR^{1A}R^{1B}$ and $R^2$ may be substituted or unsubstituted alkyl as described herein, including embodiments thereof. $R^1$ may be —$NR^{1A}R^{1B}$ and $R^2$ may be —$NR^{2A}R^{2B}$. $R^{1A}$, $R^{1B}$, $R^{2A}$, and $R^{2B}$ may be hydrogen.

The compound of formula (I) may have formula:

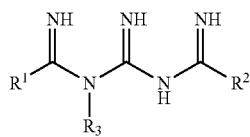

(VIII)

and pharmaceutically acceptable salts thereof. $R^1$, $R^2$, and $R^3$ are as described herein, including embodiments thereof.

The compound of formula (VIII) may have formula:

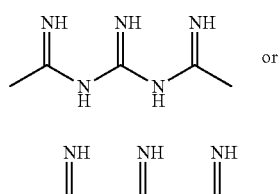

(O12a)

or (O12b)

and pharmaceutically acceptable salts thereof.

In embodiments, the compound of Formula (I) is metformin.

In embodiments, the compound of Formula (I) is

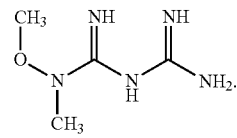

In embodiments, the compound of Formula (I) is

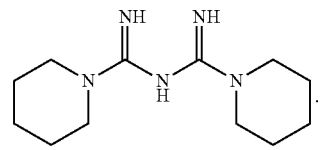 [SMILES: N=C(NC(=N)N1CCCCC1)N1CCCCC1]

In embodiments, the compound of Formula (I) is

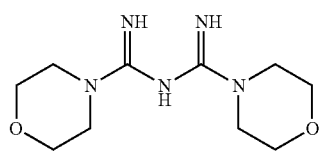

In embodiments, the compound of Formula (I) is

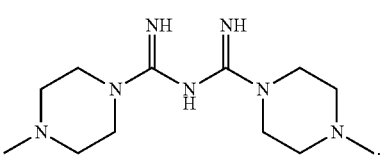

In embodiments, the compound of Formula (I) is

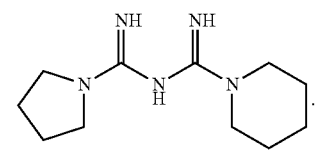 [SMILES: N=C(NC(=N)N1CCCC1)N1CCCCC1]

In embodiments, the compound of Formula (I) is

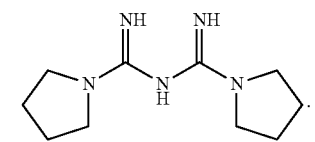 [SMILES: N=C(NC(=N)N1CCCC1)N1CCCC1]

In embodiments, the compound of Formula (I) is

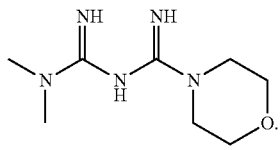

In embodiments, the compound of Formula (I) is

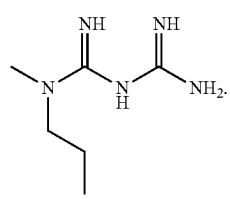

In embodiments, the compound of Formula (I) is

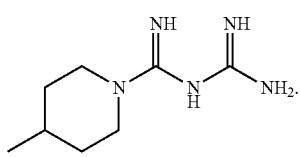

In embodiments, the compound of Formula (I) is

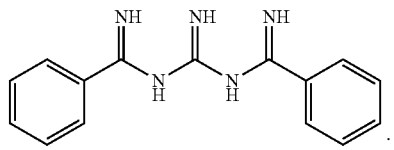 [SMILES: N=C(NC(=N)c1ccccc1)NC(=N)c1ccccc1]

In embodiments, the compound of Formula (I) is

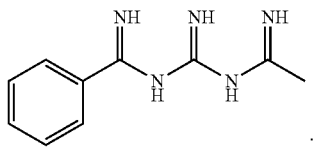

In embodiments, the compound of Formula (I) is

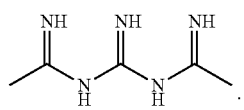

In embodiments, the compound of Formula (I) is

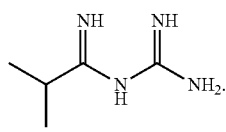

In embodiments, the compound of Formula (I) is

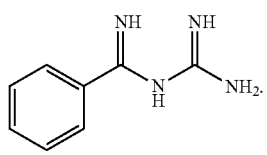 [SMILES: N=C(N)NC(=N)c1ccccc1]

In embodiments, the compound of Formula (I) is

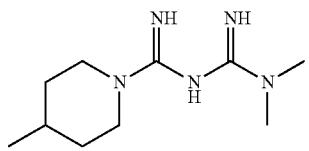

In embodiments, the compound of Formula (I) is

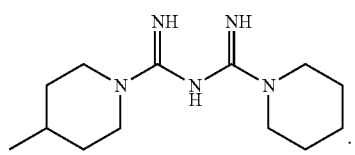 [SMILES: CC1CCN(C(=N)NC(=N)N2CCCCC2)CC1]

In embodiments, the compound of Formula (I) is. In embodiments, the compound of Formula (I) is

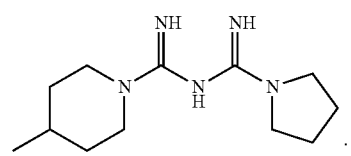 [SMILES: CC1CCN(C(=N)NC(=N)N2CCCC2)CC1]

In embodiments, the compound of Formula (I) is

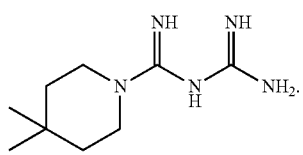

In embodiments, the compound of Formula (I) is

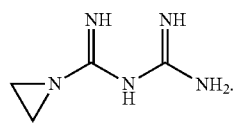

In embodiments, the compound of Formula (I) is

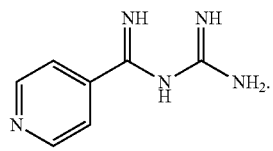 [SMILES: N=C(N)NC(=N)c1ccncc1]

In embodiments, the compound of Formula (I) is

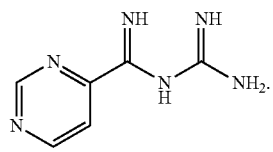 [SMILES: N=C(N)NC(=N)c1ccncn1]

In embodiments, the compound of Formula (I) is

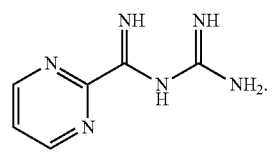 [SMILES: N=C(N)NC(=N)c1ncccn1]

In embodiments, the compound of Formula (I) is

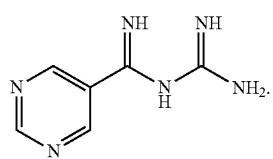 [SMILES: N=C(N)NC(=N)c1cncnc1]

In embodiments, the compound of Formula (I) is

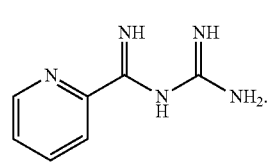 [SMILES: N=C(N)NC(=N)c1ccccn1]

In embodiments, the compound of Formula (I) is

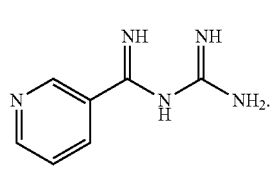 [SMILES: N=C(N)NC(=N)c1cccnc1]

In embodiments, the compound of Formula (I) is not metformin.

In embodiments, the compound of Formula (I) is not

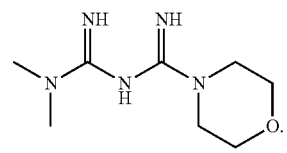

In embodiments, the compound of Formula (I) is not

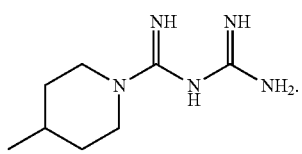

In embodiments the compound of Formula (I) is not

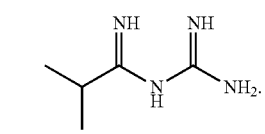

In embodiments the compound of formula (I) is not

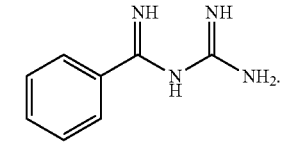 [SMILES: N=C(N)NC(=N)c1ccccc1]

In embodiments the compound of formula (I) is not

In embodiments the compound of formula (I) is not

In embodiments, the compound of Formula (I), or a pharmaceutically acceptable salt thereof, is not a compound, or a pharmaceutically acceptable salt thereof, described in James, J. W., Baker, J. A., and Wiggins L. F. The Synthesis of Some Heterocyclic Derivatives of Biguanide with Antibacterial Activity. J. Med. Chem. 1968 September; 11(5): 942-5.

III. Pharmaceutical Compositions

In another aspect, a pharmaceutical composition is provided. The composition includes a pharmaceutically acceptable excipient and a compound having formula:

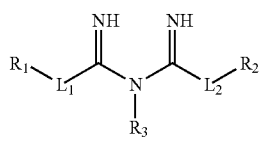
(I)

$L^1$ and $L^2$ are independently a bond or —NH—C(NH)—. $R^1$ is —$NR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{1A}$ and $R^{1B}$ are optionally joined together to form a substituted or unsubstituted heterocycloalkyl. $R^2$ is —$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{2A}$ and $R^{2B}$ are optionally joined together to form a substituted or unsubstituted heterocycloalkyl. $R^{1A}$, $R^{1B}$, $R^{2A}$, and $R^{2B}$ are independently hydrogen, —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or unsubstituted $C_1$-$C_5$ alkyl. $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$, L2, $R^1$, $R^2$, $R^{1A}$, $R^{1B}$, $R^{2A}$, $R^{2B}$, and $R^3$ are as described herein, including embodiments thereof. The pharmaceutical composition may include a pharmaceutically acceptable excipient and a compound of formula (I), (II), (III), (IV), (V), (VI), (VII), or (VIII), including embodiments thereof. The composition may include one or more of the compounds described herein, including embodiments thereof.

The pharmaceutical composition may include a compound having formula:

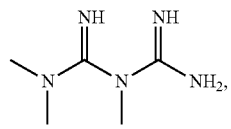
(000b)

-continued

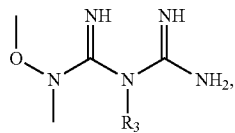
(001)

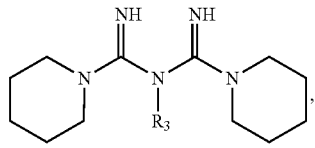
(002)

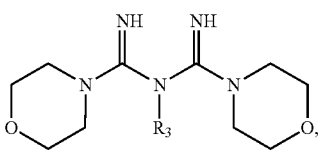
(003)

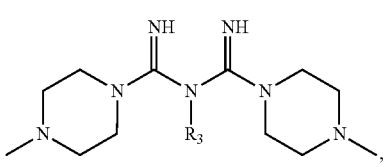
(004)

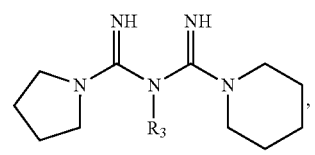
(005)

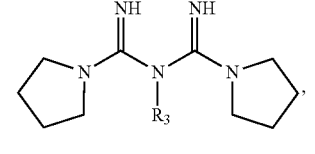
(006)

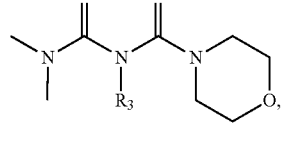
(007)

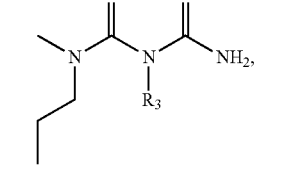
(008)

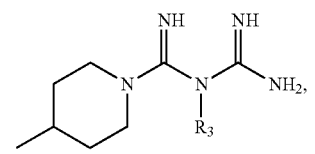
(009)

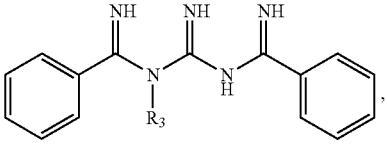
(010)

-continued
(011) 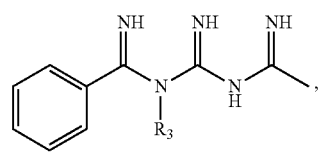
(012) 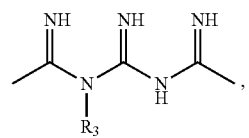
(013) 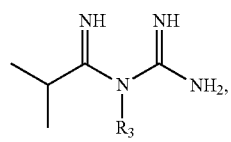
(014) 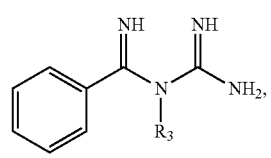
(015) 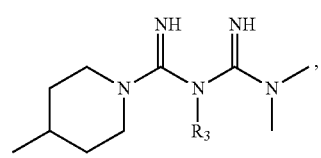
(016) 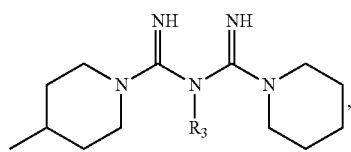
(017) 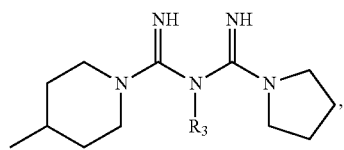
(018) 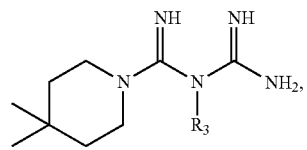
(019) 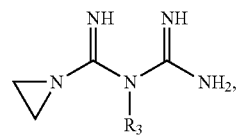
(020) 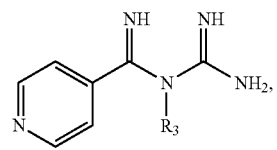
-continued
(021) 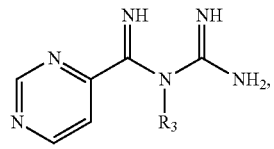
(022) 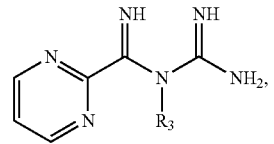
(023) 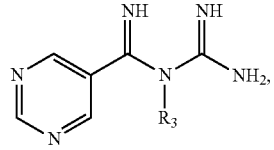
(024) 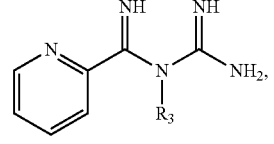
(025) 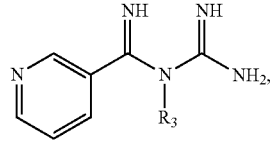
wherein, $R^3$ is hydrogen or methyl. $R^3$ may be hydrogen. $R^3$ may be methyl.
The pharmaceutical composition may include a compound having formula:
(005a) 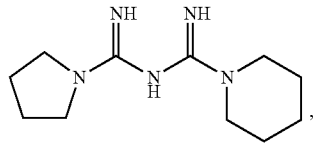
(002a) 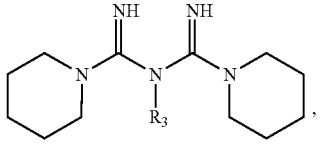
(009a) 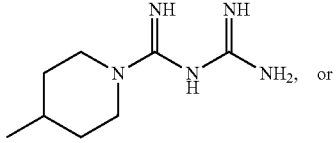
(011a) 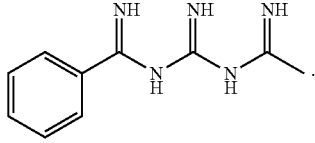

The pharmaceutical composition may include a pharmaceutically acceptable salt of a compound, as described herein (including embodiments). The pharmaceutical composition may include an anti-cancer agent. In embodiments, the pharmaceutical composition includes a compound as described herein and an anti-cancer agent. The pharmaceutical composition may be useful in the treatment of cancer (e.g. colon cancer, colorectal cancer, ovarian cancer, prostate cancer, lung cancer, breast cancer, pancreatic cancer, melanoma, triple negative breast cancer subtype, or non-small cell lung cancer). In embodiments, the anti-cancer agent is one that is approved (e.g. by a governmental regulatory agency such as the FDA) for use in a treatment of the cancer for which the pharmaceutical composition is useful.

The pharmaceutical compositions include optical isomers, diastereomers, or pharmaceutically acceptable salts of the compounds described herein (including embodiments) (e.g. agents, modulators, inhibitors, antagonists). The compound included in the pharmaceutical composition may be covalently attached to a carrier moiety, as described above. Alternatively, the compound included in the pharmaceutical composition is not covalently linked to a carrier moiety.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). In embodiments, the compounds may be coadministered with an anti-cancer agent.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g. a compound provided herein. In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule and/or reducing, eliminating, or slowing the progression of disease symptoms (e.g. growth, proliferation, or spread of cancer, breast cancer, triple negative breast cancer subtype, lung cancer, non-small cell lung cancer, pancreatic cancer, melanoma, metastasis, colon cancer, prostate cancer, or ovarian cancer). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. cancer, metastatic cancer, breast cancer, triple negative breast cancer subtype, lung cancer, non-small cell lung cancer, pancreatic cancer, melanoma, colon cancer, prostate cancer, or ovarian cancer), kind of concurrent treatment, complications from the disease being treated or other health-related problems. Other therapeutic regimens or agents can be used in conjunction with the methods and compounds described herein (including embodiments). Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch.1, p. 1, 1975. The exact formulation, route of administration and dosage can be chosen by the individual physician in view of the patient's condition and the particular method in which the compound is used.

1. Administration

The compositions described herein (including embodiments) can be delivered transdermally, by a topical route, formulated as applicator sticks, solutions, suspensions, emulsions, gels, creams, ointments, pastes, jellies, paints, powders, and aerosols.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds described herein can be used in combination with one another, with other active agents known to be useful in treating cancer (e.g. breast cancer, triple negative breast cancer subtype, lung cancer, non-small cell lung cancer, pancreatic cancer, melanoma, metastatic cancer, colon cancer, prostate cancer, or ovarian cancer), or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

In embodiments, a pharmaceutical composition as described herein includes a compound selected from the compounds described in Table 1.

IV. Methods of Treating

In another aspect, a method of treating cancer in a patient (e.g. subject) in need of such treatment is provided. The method includes administering a therapeutically effective amount of a compound described herein. The compound has the formula:

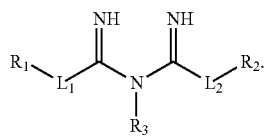

(I)

$L^1$ and $L^2$ are independently a bond or —NH—C(NH)—; $R^1$ is —$NR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{1A}$ and $R^{1B}$ are optionally joined together to form a substituted or unsubstituted heterocycloalkyl. $R^2$ is —$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{2A}$ and $R^{2B}$ are optionally joined together to form a substituted or unsubstituted heterocycloalkyl. $R^{1A}$, $R^{1B}$, $R^{2A}$, and $R^{2B}$ are independently hydrogen, —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen or unsubstituted $C_1$-$C_5$ alkyl. $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$, $L^2$, $R^1$, $R^2$, $R^{1A}$, $R^{1B}$, $R^{2A}$, $R^{2B}$, and $R^3$ are as described herein, including embodiments thereof. The administered compounds may include compounds of formula (I), (II), (III), (IV), (V), (VI), (VII), or (VIII), including embodiments thereof. The administration may include one or more of the compounds described herein, including embodiments thereof. The administered compounds may include pharmaceutical compositions prepared according to the methods described herein, including embodiments thereof.

The method may include a compound having formula:

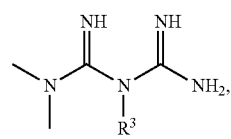
(000b)

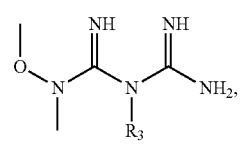
(001)

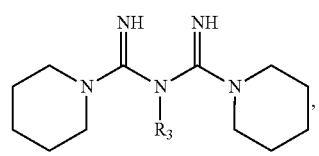
(002)

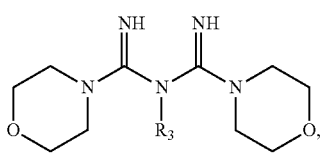
(003)

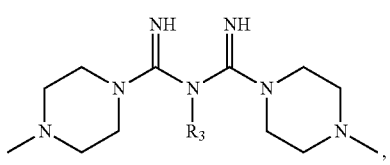
(004)

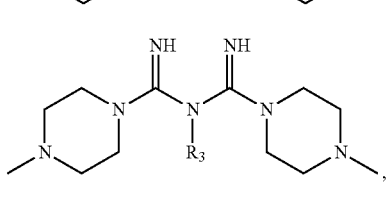
(005)

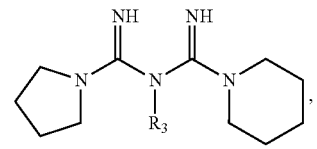
(006)

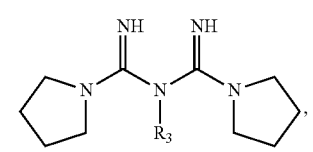
(007)

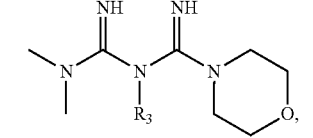
(008)

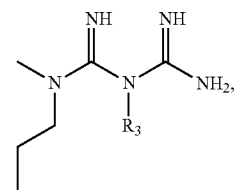

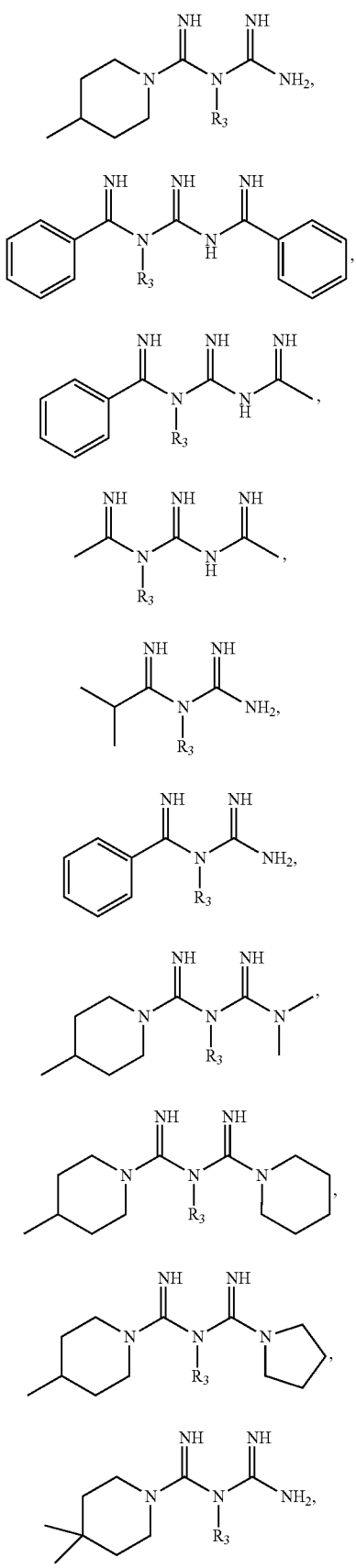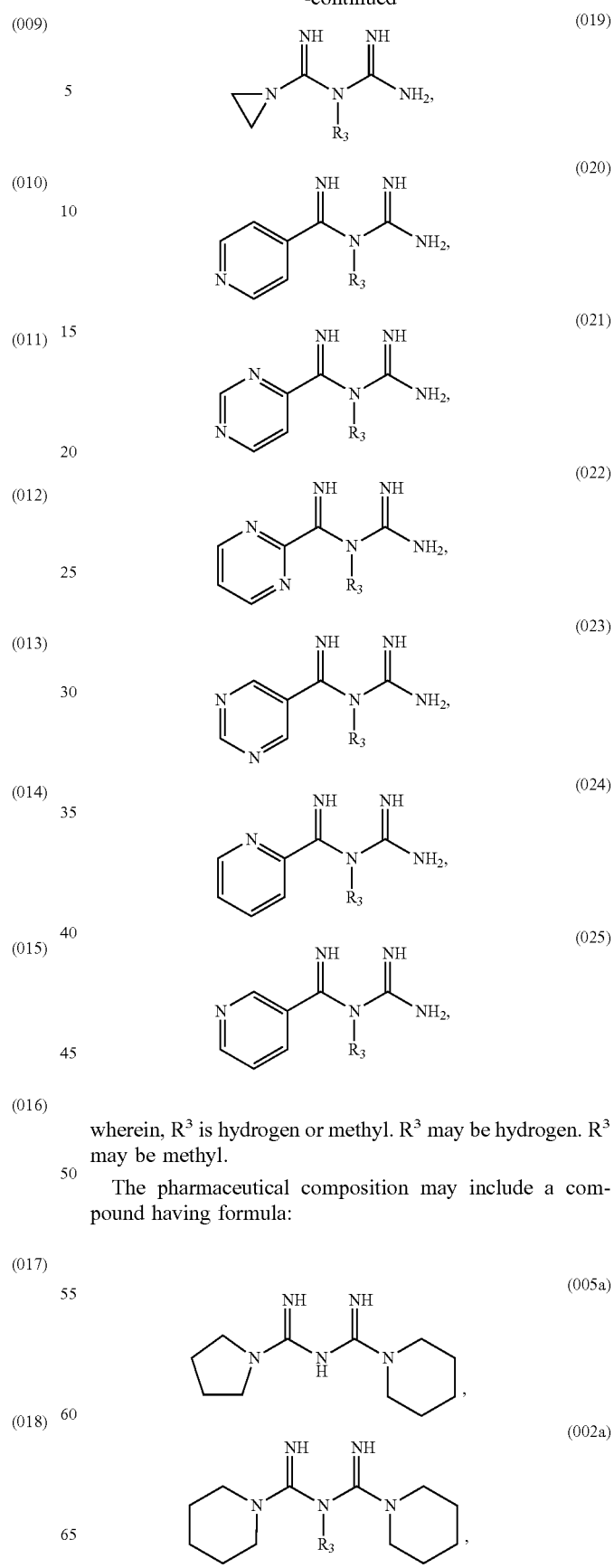
wherein, $R^3$ is hydrogen or methyl. $R^3$ may be hydrogen. $R^3$ may be methyl.
The pharmaceutical composition may include a compound having formula:

-continued

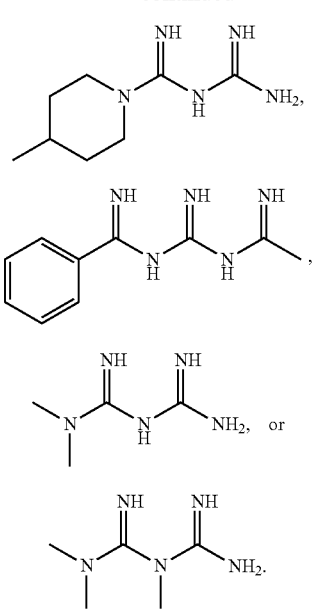

In embodiments of the method of treating cancer, the cancer is selected from colon cancer, colorectal cancer, ovarian cancer, prostate cancer, lung cancer, breast cancer, pancreatic cancer, and melanoma. In embodiments of the method of treating cancer, the cancer is selected from lung cancer, breast cancer, pancreatic cancer, and melanoma. In embodiments, the cancer is triple negative breast cancer subtype. In embodiments, the breast cancer cells do not express estrogen receptor alpha. In embodiments, the breast cancer cells do not express progesterone receptor. In embodiments, the breast cancer cells do not express human epidermal growth factor receptor 2 (HER2). In embodiments, the breast cancer cells do not overexpress estrogen receptor alpha relative to control cells (e.g. non-cancerous breast cells, non-cancerous breast cells of the same cell original, non-cancerous breast cells from the same subject as the breast cancer cells, cells having expression levels of protein or having transcription levels of mRNA not associated with cancer). In embodiments, the breast cancer cells do not overexpress progesterone receptor relative to control cells. In embodiments, the breast cancer cells do not overexpress human epidermal growth factor receptor 2 (HER2) relative to control cells.

In embodiments, triple negative breast cancer subtype cells do not express estrogen receptor alpha, progesterone receptor, and HER2. In embodiments, triple negative breast cancer subtype cells do not overexpress estrogen receptor alpha, progesterone receptor, and HER2. In embodiments, triple negative breast cancer subtype cells do not express estrogen receptor alpha and progesterone receptor and do not overexpress HER2. In embodiments, triple negative breast cancer subtype cells do not clinically express estrogen receptor alpha, progesterone receptor, and HER2. In embodiments, triple negative breast cancer subtype cells do not clinically express estrogen receptor alpha and progesterone receptor, and do not overexpress HER2. In embodiments, triple negative breast cancer subtype cells do not clinically express estrogen receptor alpha and do not overexpress progesterone receptor and HER2. In embodiments, triple-negative breast cancers lack clinical expression of estrogen receptor-alpha and progesterone receptor and HER-2 overexpression. In embodiments, triple-negative breast cancer cells lack clinical expression of estrogen receptor-alpha, progesterone receptor and HER-2 overexpression.

The cancer may be lung, pancreatic, melanoma, colon, colorectal, ovarian, or prostate cancer. The cancer may be lung cancer or pancreatic cancer. In embodiments, the cancer is lung cancer. In embodiments, the cancer is non-small cell lung cancer. In embodiments, the cancer is pancreatic cancer. In embodiments, the cancer is melanoma. In embodiments, the cancer is colon cancer. In embodiments, the cancer is colorectal cancer. In embodiments, the cancer is ovarian cancer. In embodiments, the cancer is prostate cancer. In embodiments of the method of treating cancer, the method includes administering an anti-cancer agent. In embodiments of the method of treating cancer, the method includes co-administering a compound as described herein (including embodiments) and an anti-cancer agent.

V. Embodiments

1. A compound having the formula:

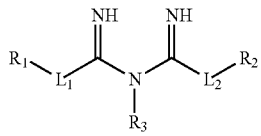

wherein;

$L^1$ and $L^2$ are independently a bond or —NH—C(NH)—;

$R^1$ is —NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{1A}$ and R$^{1B}$ are optionally joined together to form a substituted or unsubstituted heterocycloalkyl;

$R^2$ is —NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{2A}$ and R$^{2B}$ are optionally joined together to form a substituted or unsubstituted heterocycloalkyl;

R$^{1A}$, R$^{1B}$, R$^{2A}$, and R$^{2B}$ are independently hydrogen, —OR$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen or unsubstituted C$_1$-C$_5$ alkyl; and $R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein if L$^1$ and L$^2$ are a bond and R$^1$ is 4'-Me piperidine, R$^2$ is not —NH$_2$;

wherein if L$^1$ and L$^2$ are a bond and R$^1$ is —C(CH$_3$)(CH$_3$), R$^2$ is not —NH$_2$;

wherein if L¹ and L² are a bond and R¹ is phenyl, R² is not —NH₂;

wherein if L¹ and L² are a bond and R¹ᴬ and R¹ᴮ are both hydrogen, then R²ᴬ and R²ᴮ are not both methyl;

wherein if L¹ and L² are a bond and R¹ is 2'- or 3'-pyridinyl, R² is not NH₂; and wherein L¹ and L² are a bond and R¹ᴬ and R¹ᴮ are both methyl, R² is not morpholino.

2. The compound of embodiment 1 having formula (I), wherein L¹ is a bond.
3. The compound of embodiments 1 or 2, wherein L² is a bond.
4. The compound of any one of embodiments 1 to 3, wherein
   R¹ is —NR¹ᵃR¹ᵇ; and
   R² is —NR²ᵃR²ᵇ or substituted or unsubstituted heterocycloalkyl
5. The compound of embodiment 4, wherein R¹ᵃ is substituted or unsubstituted heteroalkyl or substituted or unsubstituted alkyl.
6. The compound of any one of embodiments 4 to 5, wherein R¹ᴮ is substituted or unsubstituted alkyl.
7. The compound of any one of embodiments 4 to 6, wherein R² is —NR²ᴬR²ᴮ.
8. The compound of claim 7, wherein R²ᴬ and R²ᴮ are independently hydrogen or substituted or unsubstituted alkyl.
9. The compound of embodiment 7, wherein R²ᴬ and R²ᴮ are hydrogen.
10. The compound of any one of embodiments 4 to 9, having formula:

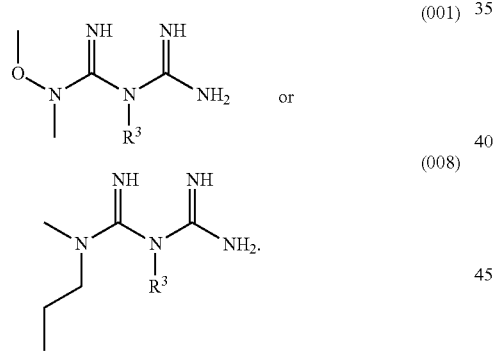

11. The compound of any one of embodiments 4 to 6, wherein R² is substituted or unsubstituted heterocycloalkyl.
12. The compound of any one of embodiments 1 to 3, wherein R¹ is —NR¹ᴬR¹ᴮ or substituted or unsubstituted heterocycloalkyl and R² is —NR²ᴬR²ᴮ or substituted or unsubstituted heterocycloalkyl.
13. The compound of embodiment 12, wherein R¹ is —NR¹ᴬR¹ᴮ, and wherein R¹ᴬ and R¹ᴮ are joined together to form a substituted or unsubstituted 3 to 8 membered heterocycloalkyl.
14. The compound of embodiment 13, wherein R¹ᴬ and R¹ᴮ are joined to form a substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, substituted or unsubstituted dithiolanyl, substituted or unsubstituted piperidinyl, substituted or unsubstituted morpholinyl, substituted or unsubstituted dioxanyl, or substituted or unsubstituted dithianyl, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, or substituted or unsubstituted tetrahydropyranyl.
15. The compound of any one of embodiments 12 to 14, wherein R² is —NR²ᴬR²ᴮ, and wherein R²ᴬ and R²ᴮ are joined to form a substituted or unsubstituted 5 to 8 membered heterocycloalkyl.
16. The compound of embodiment 15, wherein R²ᴬ and R²ᴮ are joined to form a substituted or unsubstituted pyrrolidine, substituted or unsubstituted imidazolidine, substituted or unsubstituted oxazolidine, substituted or unsubstituted thiazolidine, substituted or unsubstituted dioxolane, or substituted or unsubstituted dithiolane, substituted or unsubstituted piperidine, substituted or unsubstituted morpholine, substituted or unsubstituted dioxane, or substituted or unsubstituted dithiane, substituted or unsubstituted aziridinyl, substituted or unsubstituted azetidinyl, substituted or unsubstituted azepinyl, substituted or unsubstituted oxiranyl, substituted or unsubstituted oxetanyl, substituted or unsubstituted tetrahydrofuranyl, or substituted or unsubstituted tetrahydropyranyl.
17. The compound of any one of embodiments 1 to 3, or 11 to 16, said compound having formula:

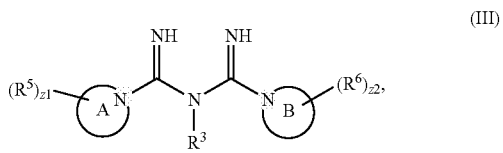

wherein,
Ring A and Ring B are independently substituted or unsubstituted 3 to 8 membered heterocycloalkyl;
z1 is an integer from 2 to 7;
z2 is an integer from 2 to 7;
R⁵ and R⁶ are independently hydrogen, halogen, —N₃, —NO₂, —CF₃, —CCl₃, —CBr₃, —CI₃, —CN, —OH, —NH₂, —COOH, CONH₂, —NO₂, —SH, —SO₂Cl, —SO₃H, —SO₄H, —SO₂NH₂, —NHNH₂, —ONH₂, —NHC═(O)NHNH₂; substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or are optionally bonded together to form a substituted or unsubstituted cycloalkyl, a substituted or unsubstituted heterocycloalkyl, a substituted or unsubstituted aryl, or a substituted or unsubstituted heteroaryl.
18. The compound of embodiment 17, wherein ring A is different from ring B.
19. The compound of embodiment 18, wherein ring A is a 5 membered heterocycloalkyl and ring B is a 6 membered heterocycloalkyl.
20. The compound of embodiment 19, wherein ring A is substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, or substituted or unsubstituted dithiolanyl and ring B is substituted or unsubstituted piperidinyl, substituted or unsubstituted morpholinyl, substituted or unsubstituted dioxanyl, or substituted or unsubstituted dithianyl.

21. The compound of embodiment 18, wherein ring A is a 6 membered substituted or unsubstituted heterocycloalkyl, and ring B is a 5 membered substituted or unsubstituted heterocycloalkyl.

22. The compound of embodiment 21, wherein ring A is substituted or unsubstituted piperidinyl, substituted or unsubstituted morpholinyl, substituted or unsubstituted dioxanyl, or substituted or unsubstituted dithianyl and ring B is substituted or unsubstituted pyrrolidinyl, substituted or unsubstituted imidazolidinyl, substituted or unsubstituted oxazolidinyl, substituted or unsubstituted thiazolidinyl, substituted or unsubstituted dioxolanyl, or substituted or unsubstituted dithiolanyl.

23. The compound of any one of embodiments 1 to 3, or 17 to 22 having formula;

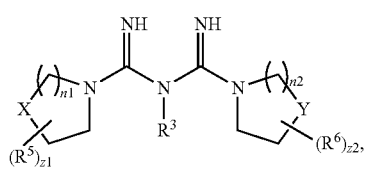

(IIIa)

wherein,
X is —CH$_2$—, —O—, or —NH—;
Y is —CH$_2$—O—, or —NH—;
n1 is an integer from 1 to 4; and
n2 is an integer from 1 to 4

24. The compound of embodiment 23, wherein n1 is not equal to n2.

25. The compound of embodiment 23, having formula:

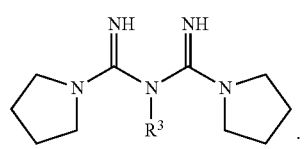

(006)

26. The compound of embodiment 23 having formula:

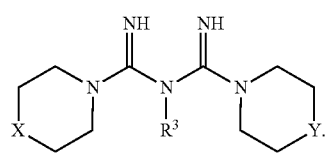

(IIId)

27. The compound of embodiment 26, wherein X and Y are —O—.

28. The compound of embodiment 26, wherein X and Y are —NMe.

29. The compound of embodiment 26, wherein X and Y are CH$_2$.

30. The compound of embodiment 23 having formula:

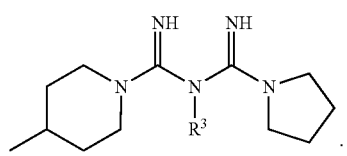

(017)

31. The compound of embodiment 23 having formula:

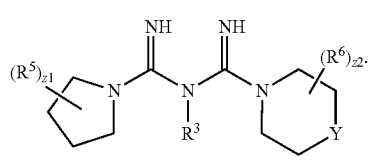

(IVb)

32. The compound of embodiment 31 having formula:

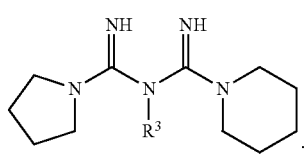

(005)

33. The compound of embodiment 12, wherein R$^{1A}$ and R$^{1B}$ are joined together to form a substituted or unsubstituted heterocycloalkyl and R$^{2A}$ and R$^{2B}$ are hydrogen or substituted or unsubstituted alkyl.

34. The compound of claim 33 having formula:

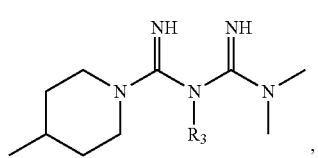

(015)

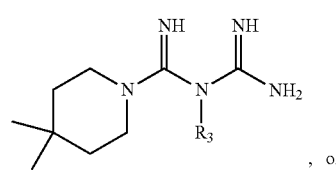

(018)

, or

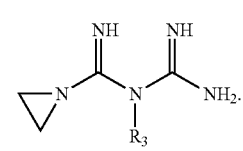

(019)

35. The compound of any one of embodiments 1 to 3, wherein R$^1$ is substituted or unsubstituted aryl or substituted or unsubstituted heteroaryl and R$^2$ is —NR$^{2A}$R$^{2B}$.

36. The compound of embodiment 35 having formula:

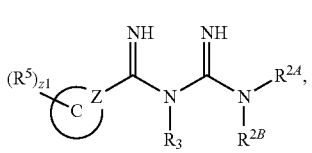

wherein,
Ring C is substituted or unsubstituted 5 to 8 membered aryl or substituted or unsubstituted 5 to 8 membered heteroaryl; and
Z is —C—, —O—, or —S—.

37. The compound of embodiment 36, wherein $R^{2A}$ and $R^{2B}$ are hydrogen.

38. The compound of embodiment 36, wherein $R^{2A}$ and $R^{2B}$ are joined together to form a 3 to 8 membered heterocycloalkyl.

39. The compound of embodiment 36 having formula:

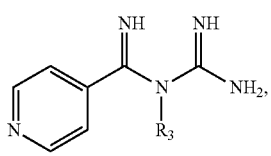

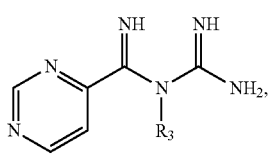

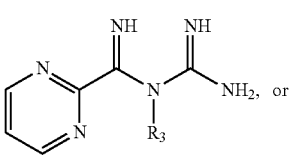

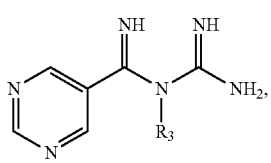

wherein $R^3$ is hydrogen or methyl.

40. The compound of any one of claims 1 to 3, wherein $R^1$ is substituted or unsubstituted alkyl and $R^2$ is —$NR^{2A}R^{2B}$.

41. The compound of embodiments 1 or 2, wherein $L^2$ is —NH—C(NH)—.

42. The compound of embodiment 41, wherein $R^1$ and $R^2$ are independently substituted or unsubstituted aryl or substituted or unsubstituted alkyl.

43. The compound of embodiment 42, wherein $R^1$ and $R^2$ are independently substituted or unsubstituted aryl.

44. The compound of embodiment 43, wherein $R^1$ and $R^2$ are independently substituted or unsubstituted phenyl.

45. The compound of embodiment 44, wherein $R^1$ and $R^2$ are unsubstituted phenyl.

46. The compound of embodiment 42, wherein $R^1$ and $R^2$ are independently substituted or unsubstituted alkyl.

47. The compound of embodiment 46, wherein $R^1$ and $R^2$ are independently substituted or unsubstituted $C_1$-$C_5$ alkyl.

48. The compound of embodiment 47, wherein $R^1$ and $R^2$ are methyl.

49. The compound of embodiment 42, wherein $R^1$ is substituted or unsubstituted aryl and $R^2$ is substituted or unsubstituted alkyl.

50. The compound of embodiment 49, wherein $R^1$ is substituted or unsubstituted phenyl.

51. The compound of embodiment 50, wherein $R^1$ is unsubstituted phenyl.

52. The compound of embodiment 49, wherein $R^2$ is $C_1$-$C_5$ substituted or unsubstituted alkyl.

53. The compound of embodiment 52, wherein $R^2$ is methyl.

54. The compound of any one of embodiments 1 to 53, wherein $R^3$ is hydrogen.

55. The compound of any one of embodiments 1 to 53, wherein $R^3$ is methyl.

56. A pharmaceutical composition comprising a pharmaceutically acceptable excipient and a compound having formula:

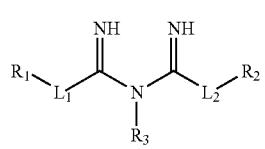

wherein;
$L^1$ and $L^2$ are independently a bond or —NH—C(NH)—;
$R^1$ is —$NR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{1A}$ and $R^{1B}$ are optionally joined together to form a substituted or unsubstituted heterocycloalkyl;
$R^2$ is —$NR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^{2A}$ and $R^{2B}$ are optionally joined together to form a substituted or unsubstituted heterocycloalkyl;
$R^{1A}$, $R^{1B}$, $R^{2A}$, and $R^{2B}$ are independently hydrogen, —$OR^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen or unsubstituted $C_1$-$C_5$ alkyl; and
$R^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

57. The pharmaceutical composition of embodiment 56, wherein said compound has the formula:
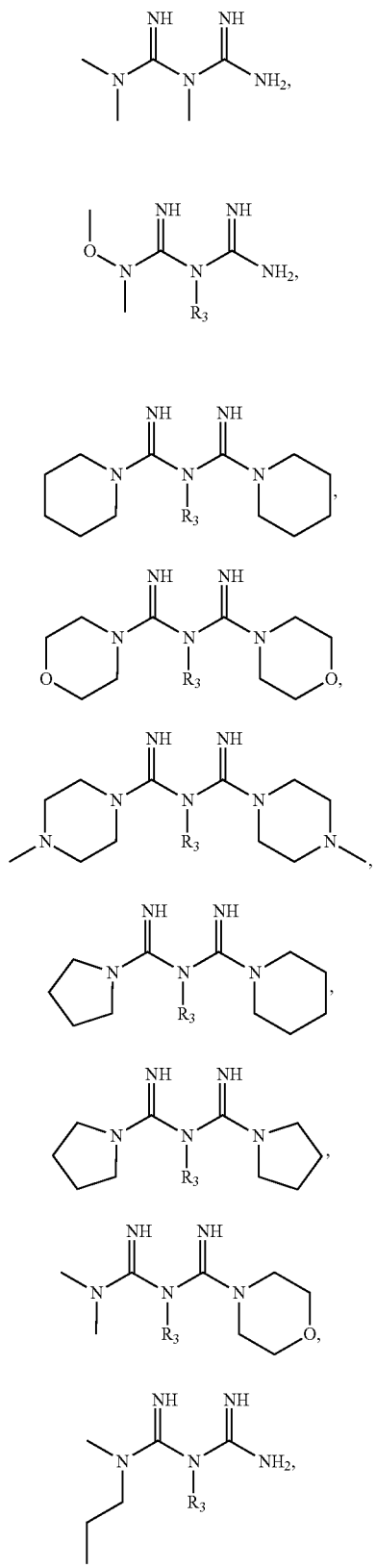
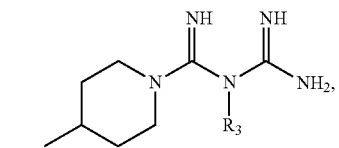
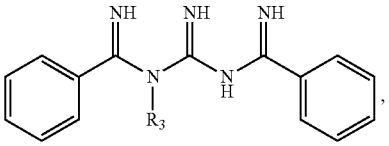
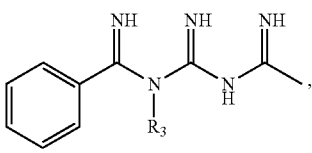
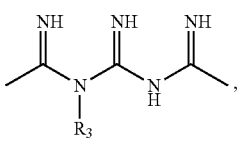
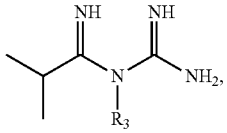
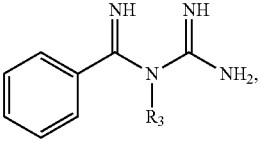
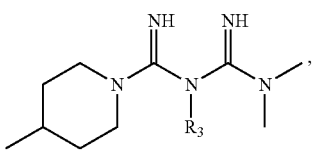
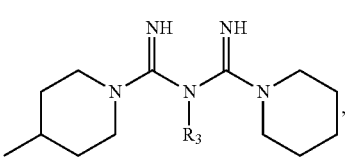
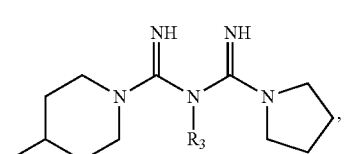
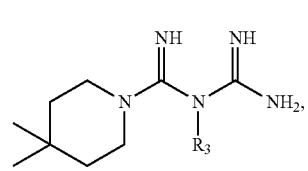

-continued

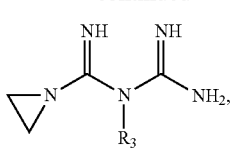 (019)

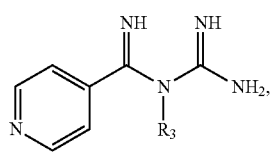 (020)

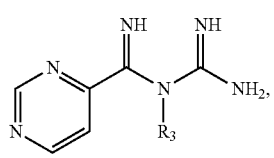 (021)

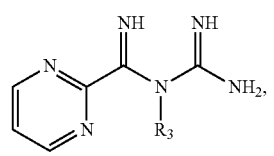 (022)

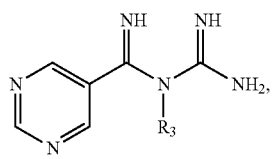 (023)

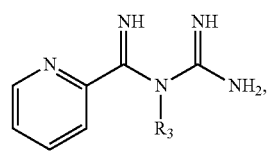 (024)

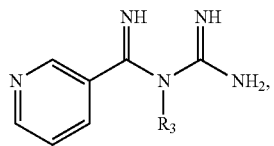 (025)

wherein $R^3$ is hydrogen or methyl

58. The pharmaceutical composition of embodiment 57, wherein $R^3$ is hydrogen.
59. The pharmaceutical composition of embodiment 57, wherein $R^3$ is methyl.
60. A method of treating cancer in a subject in need thereof, said method comprising administering a therapeutically effective amount a compound having formula:

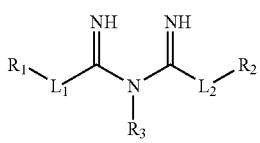 (I)

wherein;
L$^1$ and L$^2$ are independently a bond or —NH—C(NH)—;
R$^1$ is —NR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{1A}$ and R$^{1B}$ are optionally joined together to form a substituted or unsubstituted heterocycloalkyl;
R$^2$ is —NR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^{2A}$ and R$^{2B}$ are optionally joined together to form a substituted or unsubstituted heterocycloalkyl,
R$^{1A}$, R$^{1B}$, R$^{2A}$, and R$^{2B}$ are independently hydrogen, —OR$^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is hydrogen or unsubstituted C$_1$-C$_5$ alkyl; and
R$^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

61. The method of embodiment 60, wherein said compound has formula:

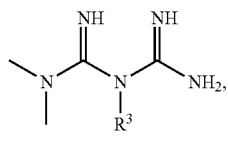 (000)

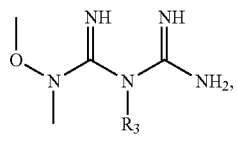 (001)

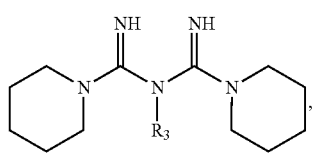 (002)

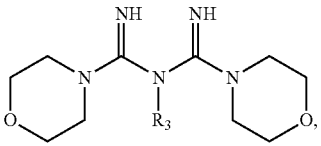 (003)

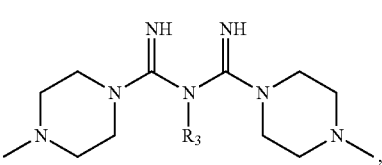 (004)

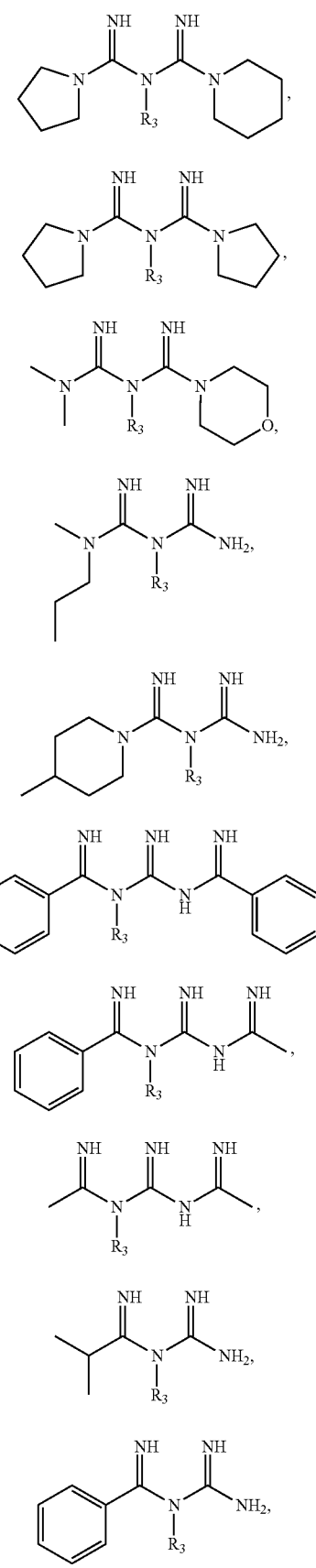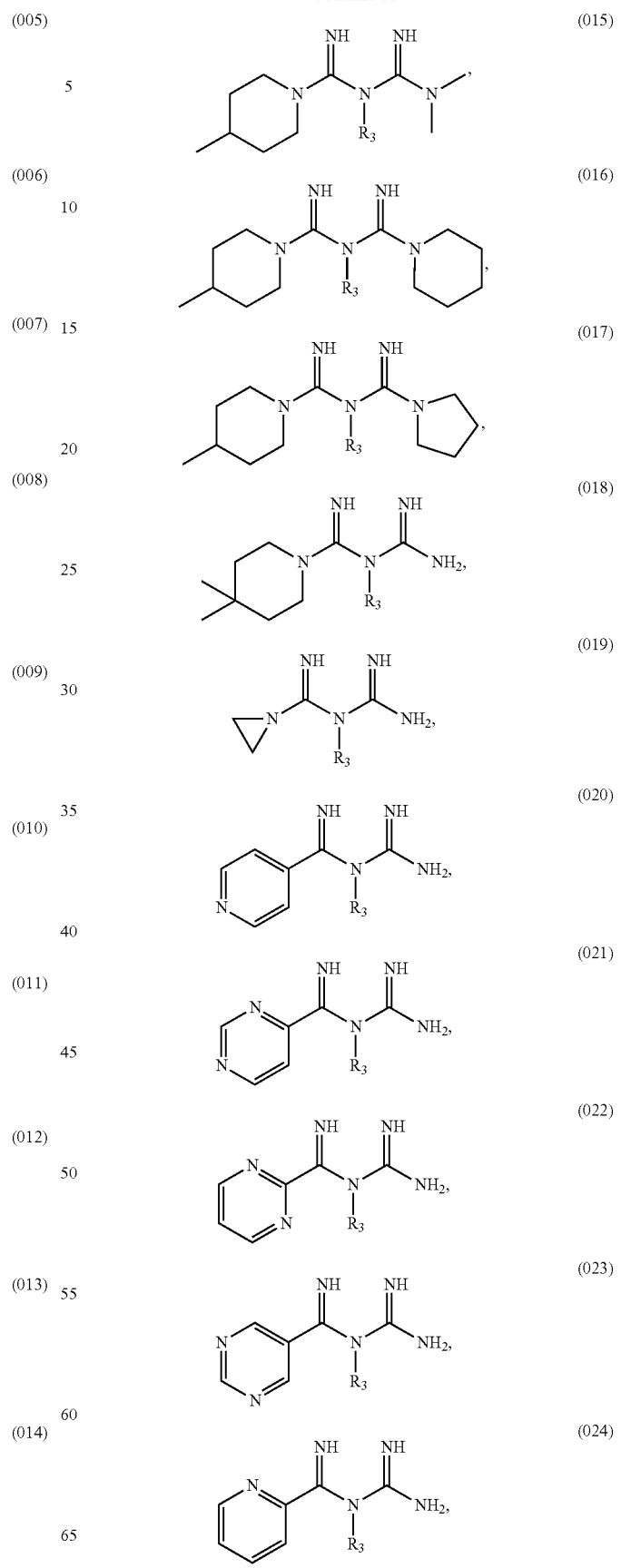

-continued

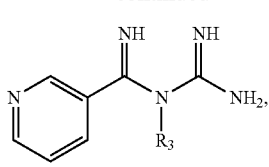

(025)

wherein R³ is hydrogen or methyl.
62. The method of embodiment 61, wherein R³ is hydrogen.
63. The method of embodiment 61, wherein R³ is methyl.
64. The method of embodiment 60, wherein said cancer is breast cancer, lung cancer, or pancreatic cancer.
65. The method of embodiment 64, wherein said cancer is breast cancer.
66. The method of embodiment 65, wherein said breast cancer is triple negative breast cancer.
67. The method of embodiment 64, wherein said cancer is lung cancer.
68. The method of embodiment 67, wherein said lung cancer is non-small cell lung cancer.
69. The method of embodiment 64, wherein said cancer is pancreatic cancer.
70. A compound, or a pharmaceutically acceptable salt thereof, having the formula:

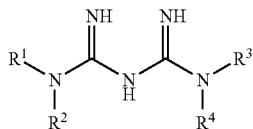

wherein, $R^1$, $R^2$, $R^3$, and $R^4$ are each independently hydrogen, substituted or unsubstituted alkyl, or substituted or unsubstituted heteroalkyl;
$R^1$ and $R^2$ may optionally be joined to form a substituted or unsubstituted heterocycloalkyl or substituted or unsubstituted heteroaryl;
and $R^3$ and $R^4$ may optionally be joined to form a substituted or unsubstituted heterocycloalkyl or substituted or unsubstituted heteroaryl.
71. The compound of embodiment 70, wherein,
$R^1$, $R^2$, $R^3$, and $R^4$ are independently hydrogen, substituted or unsubstituted alkyl, or substituted or unsubstituted heteroalkyl, or
$R^1$ and $R^2$ may optionally be joined to form a substituted or unsubstituted heterocycloalkyl; and
$R^3$ and $R^4$ may optionally be joined to form a substituted or unsubstituted heterocycloalkyl.
72. The compound of one of embodiments 70 or 71, wherein,
if $R^1$ and $R^2$ are joined to form an unsubstituted morpholinyl;
then $R^3$ and $R^4$ are not both unsubstituted methyl; and
if $R^3$ and $R^4$ are both hydrogen;
then $R^1$ and $R^2$ are not joined to form a 4-methyl piperidinyl.
73. The compound of any one of embodiments 70 to 72, wherein,
$R^1$ and $R^2$ are joined to form a substituted or unsubstituted heterocycloalkyl; and
$R^3$ and $R^4$ are joined to form a substituted or unsubstituted heterocycloalkyl.
74. The compound of any one of embodiments 70 to 73, wherein,
$R^1$, $R^2$, $R^3$, and $R^4$ are independently hydrogen, unsubstituted alkyl, or unsubstituted heteroalkyl;
75. A method of treating cancer in a patient in need of such treatment, said method comprising administering a therapeutically effective amount of a compound of any one of embodiment 70 to 73.
76. The method of embodiment 75, wherein the cancer is lung cancer, pancreatic cancer, or breast cancer.
77. The method of embodiment 75, wherein the cancer is breast cancer.
78. The method of embodiment 77, wherein the breast cancer is triple negative breast cancer subtype.
79. The method of embodiment 76, wherein the cancer is lung cancer.
80. The method of embodiment 79, wherein the lung cancer is non-small cell lung cancer.
81. A method of treating pulmonary lymphangioleiomyomatosis (LAM) or renal angiomyolipoma (AML) in a patient in need of such treatment, said method comprising administering a therapeutically effective amount of a compound of any one of embodiments 70 to 74.
82. A pharmaceutical composition comprising a pharmaceutically acceptable excipient and a compound of any one of embodiments 70 to 74.

VI. Examples

Overview

Metformin, the most commonly prescribed drug to treat type 2 diabetes mellitus in the clinic, has recently emerged as a potential anticancer agent. Evidence from epidemiologic and preclinical studies suggest that metformin exerts previously unsuspected anti-cancer and chemopreventive activity in breast and other type of malignancies (1-5). Diabetic patients treated with metformin, but not with other antidiabetic drugs, have a reduced incidence and better survival from breast cancer. Moreover, triple-negative breast cancer cells (a deadly subtype of breast cancer) are reported to be uniquely sensitive to metformin with profound molecular effects likely to have translational relevance (1,6, 7). In the clinic, metformin has modest anticancer activity but higher doses of the drug appear to exhibit better antitumor potency. Described herein is the design and synthesis of a group of derivatives of metformin that show significantly more potent anticancer activity than metformin and induce cancer cell death.

Biguanides, including metformin, phenformin and buformin, are derived from the herb Galega officinalis and were originally developed for treatment of hyperglicemia (high blood glucose levels) and type 2 diabetes. While phenformin and buformin were withdrawn from the market due to undesirable side-effects, metformin has remained one of the most commonly prescribed and safe drugs, with nearly 120 million prescriptions filled annually worldwide (8). Use of metformin in patients with diabetes has been associated with reduced cancer incidence and mortality, with speculation that insulin- and insulin like growth factor-lowering effects of metformin may be at least in part related to its anti-cancer activity (1,8).

The new compounds synthesized are analogues of the parent metformin drug but designed to exhibit more potent anticancer activity (e.g. anti-breast cancer, anti-TNBC, anti-lung cancer, anti-non-small cell lung cancer (anti-NSCLC), anti-pancreatic cancer, anti-melanoma, anti-prostate cancer, anti-colon cancer, anti-colorectal cancer, or anti-ovarian cancer) and safety as compared to metformin.

Chemical Syntheses

All the solvents or reagents were purified according to literature procedures. High Resolution Mass Spectrometry was obtained on a Waters LCT Premier XE Time of Flight LC-MS. $^1$H NMR, $^{13}$C NMR spectra were obtained on AV-300, ARX-400, ARX-500 or Avance-500 spectrometers. The chemical shifts are reported in parts per million (ppm, δ). The coupling constants are reported in Hertz (Hz) and the resonance patterns are reported with the following notations: br (broad), s (singlet), d (double), t (triplet), q (quartet) and m (multiplet). Thin-layer chromatography (TLC) was carried out using precoated silica gel sheets (Merck 60 $F_{254}$). Visual detection was performed with ultraviolet light (short wave and long wave), p-anisaldehyde stain, and potassium permanganate stain.

General Procedure A: For Compounds JD001, JD008, JD009. Dicyandiamide (cyanoguanidine) 1.26 g, 0.015 mol) and various secondary amine hydrochloride (0.015 mol) were dissolved in xylenes (40 mL), and the mixture was stirred under argon at 150° C. for 24 hours. After cooling to room temperature, the reaction mixture was evaporated to dryness under reduced pressure. The residue was dissolved in methanol and filtered. The filtrate was concentrated followed by crystallization two or three times to obtain the desired product.

General Procedure B: For representative symmetrical metformin analogues (e.g. JD002, JD003, JD004, JD006). A mixture of sodium dicyanamide (1.335 g, 0.015 mol) and the appropriate secondary amine hydrochloride (0.030 mol) in xylenes (40 mL) was refluxed for 48 hours. After cooling to room temperature, the reaction mixture was evaporated to dryness under reduced pressure. The residue was dissolved in hot methanol and filtered. The filtrate was concentrated followed by crystallization two or three times to obtain the desired product.

General Procedure C: For representative unsymmetrical analogues (e.g. JD005, JD007): A mixture of sodium dicyanamide (1.335 g, 0.015 mol) and pyrrolidine hydrochloride or dimethylamine hydrochloride (0.015 mol) in xylenes (40 mL) was refluxed for 12 h. After it was cooled to room temperature, the reaction mixture was evaporated to dryness under reduced pressure. The residue was crystallized from methanol to obtain the pure N-cyanopyrrolidine-1-carboximidamide and 3-cyano-1,1-dimethylguanidine products. Then these cyanoguanidines (0.015 mol) were dissolved separately in xylenes (40 mL) and piperidine hydrochloride or morpholine hydrochloride (0.015 mol) was added. The mixture was refluxed for 48 h, the solvent was removed under vacuum and the residue was recrystallized twice from methanol to obtain the two unsymmetrical analogues, JD005 and JD007, respectively.

N-Methoxy-N-methylbiguanide hydrochloride, JD001. The title compound, JD001, was obtained by following general procedure A using N,O-dimethylhydroxylamine hydrochloride in 78% yield after crystallization from methanol. $^1$H NMR (300 MHz, DMSO-$d_6$): δ 7.59 (2H, s), 3.63 (3H, s), 3.10 (3H, s). $^{13}$C NMR (75 MHz, DMSO-$d_6$): δ 160.3, 158.6, 61.1, 35.2.

N-(Imino(piperidin-1-yl)methyl)piperidine-1-carboximidamide hydrochloride, JD002. The title compound, JD002, was obtained by following general procedure B using piperidine hydrochloride in 38% yield after crystallization from methanol. $^1$H NMR (300 MHz, DMSO-$d_6$): δ 7.10 (1H, s), 3.38 (8H, t, J=15 Hz), 1.48 (12H, m). $^{13}$C NMR (75 MHz, DMSO-$d_6$): δ 157.1, 45.6, 25.0, 23.7.

N-(Imino(morpholino)methyl)morpholine-4-carboximidamide hydrochloride, JD003. The title compound, JD003, was obtained by following general procedure B using morpholine hydrochloride in 72% yield after crystallization from methanol. $^1$H NMR (300 MHz, DMSO-$d_6$): δ 7.06 (1H, s), 3.57 (8H, t, J=4.5 Hz), 3.36 (8H, t, J=4.5 Hz). $^{13}$C NMR (75 MHz, DMSO-$d_6$): δ 157.9, 65.5, 45.0.

N-(Imino(4-methylpiperazin-1-yl)methyl)-4-methylpiperazine-1-carboximidamide hydro-chloride, JD004. The title compound, JD004, was obtained by following general procedure B using 1-methyl-piperazine hydrochloride in 63% yield after crystallization from methanol. $^1$H NMR (300 MHz, DMSO-$d_6$): δ 7.01 (1H, s), 3.36 (8H, t, J=3.9 Hz), 2.34 (8H, t, J=3.9 Hz), 2.15 (6H, s). $^{13}$C NMR (75 MHz, DMSO-$d_6$): δ 158.4, 54.2, 45.8, 44.9.

N-(Imino(pyrrolidin-1-yl)methyl)piperidine-1-carboximidamide hydrochloride, JD005. The title compound, JD005, was obtained by following general procedure C using first pyrrolidine hydrochloride and then piperidine hydrochloride in 35% yield after crystallization from methanol. $^1$H NMR (300 MHz, DMSO-$d_6$): δ 6.88 (1H, s), 3.40 (4H, br s), 3.29 (4H, br s), 1.83 (4H, br s), 1.54 (2H, br s), 1.48 (4H, br s). $^{13}$C NMR (75 MHz, DMSO-$d_6$): δ 156.4, 156.1, 46.9, 45.6, 25.1, 24.8, 23.7.

N-(Imino(pyrrolidin-1-yl)methyl)pyrrolidine-1-carboximidamide hydrochloride, JD006. The title compound, JD006, was obtained by following general procedure B using pyrrolidine hydrochloride in 42% yield after crystallization from methanol. $^1$H NMR (300 MHz, DMSO-$d_6$): δ 6.97 (1H, s), 3.30 (8H, br s), 1.83 (8H, br s). $^{13}$C NMR (75 MHz, DMSO-$d_6$): δ 155.5, 46.9, 24.8.

N—(N,N-Dimethylcarbamimidoyl)morpholine-4-carboximidamide hydrochloride, JD007. The title compound, JD007, was obtained by following general procedure C using first dimethylamine hydrochloride and then morpholine hydrochloride in 47% yield after crystallization from methanol. 1H NMR (300 MHz, DMSO-d6): δ 7.15 (1H, s), 3.59 (4H, br s), 3.42 (4H, br s), 2.91 (6H, s). 13C NMR (75 MHz, DMSO-d6): δ 157.9, 65.5, 45.0, 37.5.

N-Methyl-N-propylbiguanide hydrochloride, JD008. The title compound, JD008, was obtained by following general procedure A using N-methylpropylamine hydrochloride in 83% yield after crystallization from methanol. 1H NMR (300 MHz, D2O): δ 3.23 (2H, t, J=7.2 Hz), 2.90 (3H, s), 1.48 (2H, m), 0.75 (3H, t, J=7.2 Hz). 13C NMR (75 MHz, D2O): δ 159.6, 158.1, 51.8, 35.4, 20.0, 10.1.

N-Carbamimidoyl-4-methylpiperidine-1-carboximidamide, hydrochloride, JD009. The title compound, JD009, was obtained by following general procedure A using 4-methylpiperidine hydrochloride in 34% yield after crystallization from methanol. 1H NMR (500 MHz, DMSO-d6): δ 6.04 (2H, s), 4.13 (4H, m), 2.61 (2H, m), 1.54 (3H, m), 0.85 (3H, d, J=6.0 Hz). 13C NMR (125 MHz, DMSO-d6): δ 167.3, 165.2, 42.9, 34.0, 31.1, 22.1.

In Vitro and In Vivo Characterization of Compounds

The new compounds described herein (including embodiments) (e.g. metformin analogues) have been tested using preclinical in vitro models where they are shown to be active at inducing cell death in different types of malignant cell types, including triple-negative breast cancer, ER-positive breast cancer, non-small cell lung cancer, pancreatic cancer and melanoma cells. The compounds (e.g. metformin analogues) are particularly active in inducing the death of triple-negative breast cancer cells (TNBC).

The effects of compounds described herein (including embodiments) (e.g. metformin analogues) were determined on two types of normal nonmalignant human cells, human umbilical vein endothelial cells (HUVEC) and human mammary epithelial cells (HMEC). There were no significant biologic effects noted on exposure to the metformin analogues.

Compounds described herein (including embodiments) (e.g. metformin analogues) are being tested in human tumor xenografts grown in immunosuppressed mice.

Figure 3A:
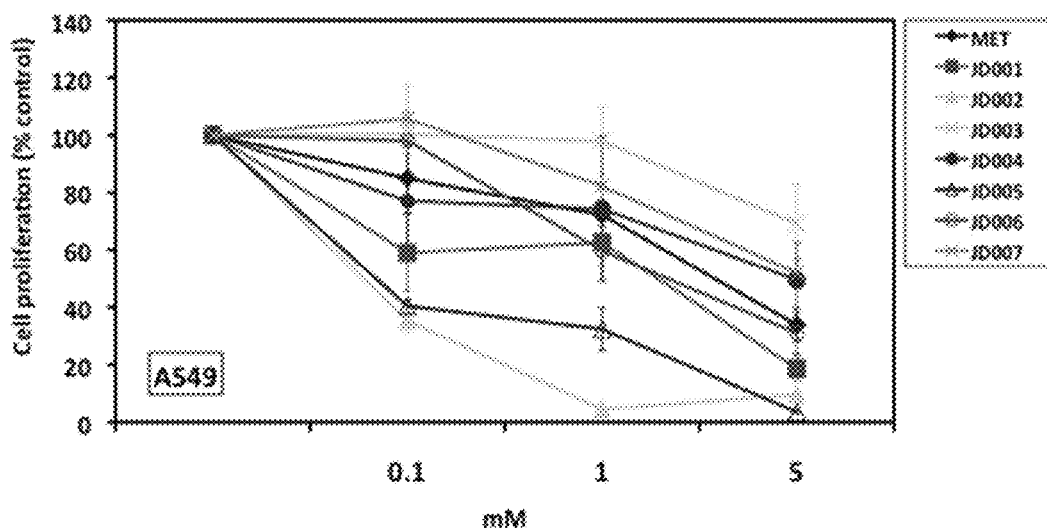
FIGS. 3A-3B. Metformin analogues inhibit survival of non-small cell lung cancer (NSCLC) (FIG. 3A) and melanoma cell lines (FIG. 3B). A549 (NSCLC) and MDA-MB-435 (melanoma) cells were cultured in medium containing 1% fetal bovine serum and increasing concentrations of metformin (MET) and analogues JD001-JD007 (0.1, 1 and 5 mM). After 3 days, MTS assay was performed. Survival is expressed as percentage of control defined at 100%.
Figure 3B:
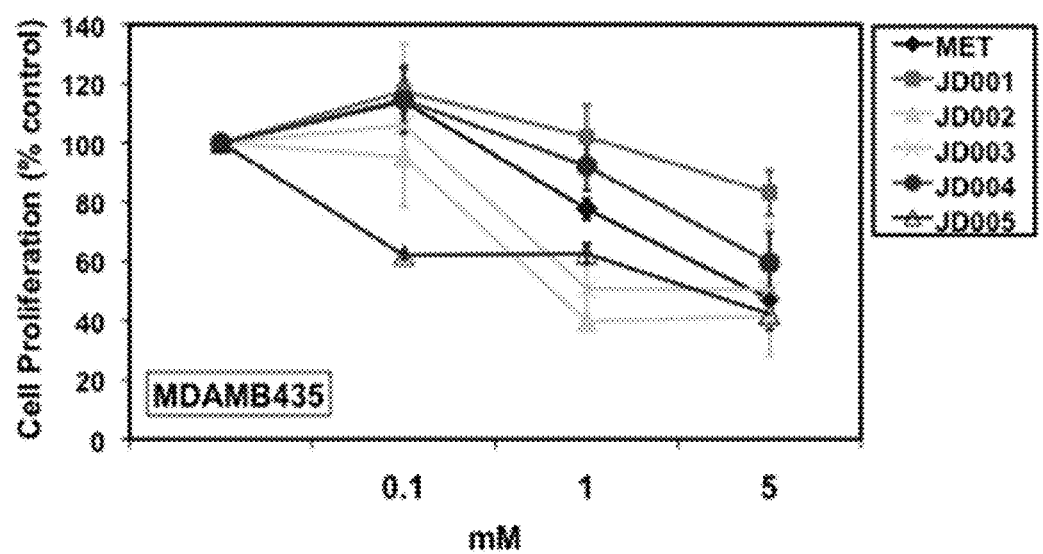
Figure 4A:
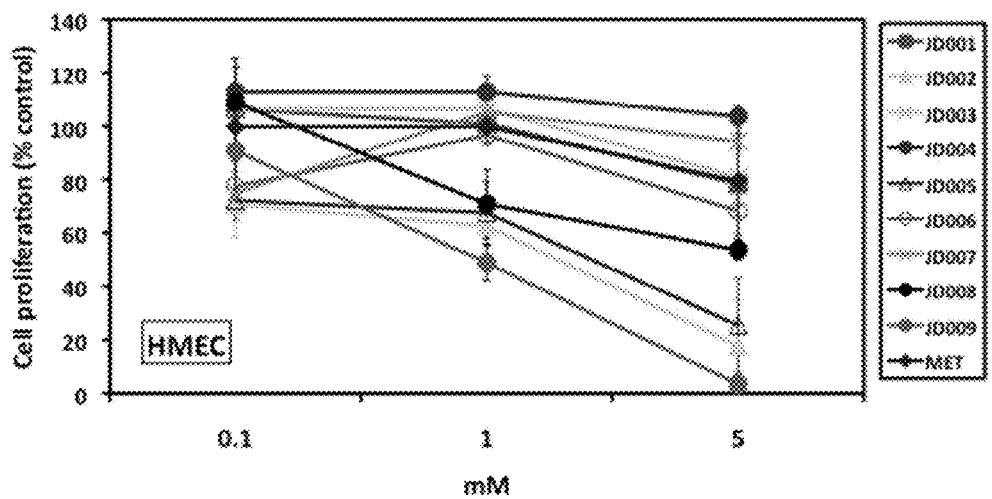
FIGS. 4A-4B. Effects of metformin and metformin analogues on normal cells. HMEC (FIG. 4A) and HUVEC (FIG. 4B) cells were plated in special media. After 24 hours, cells were treated with increasing concentrations of metformin and analogues JD001-JD009 (0.1, 1 and 5 mM). After 3 days, MTS assay was performed. Survival is expressed as percentage of vehicle treated control. Data represents at least two experiments.
Figure 4B:
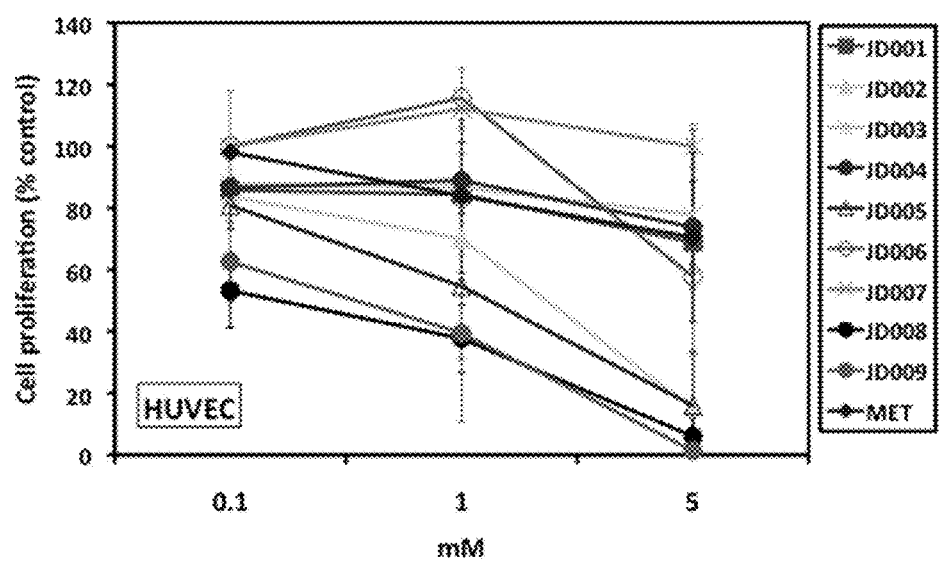
Figure 5:
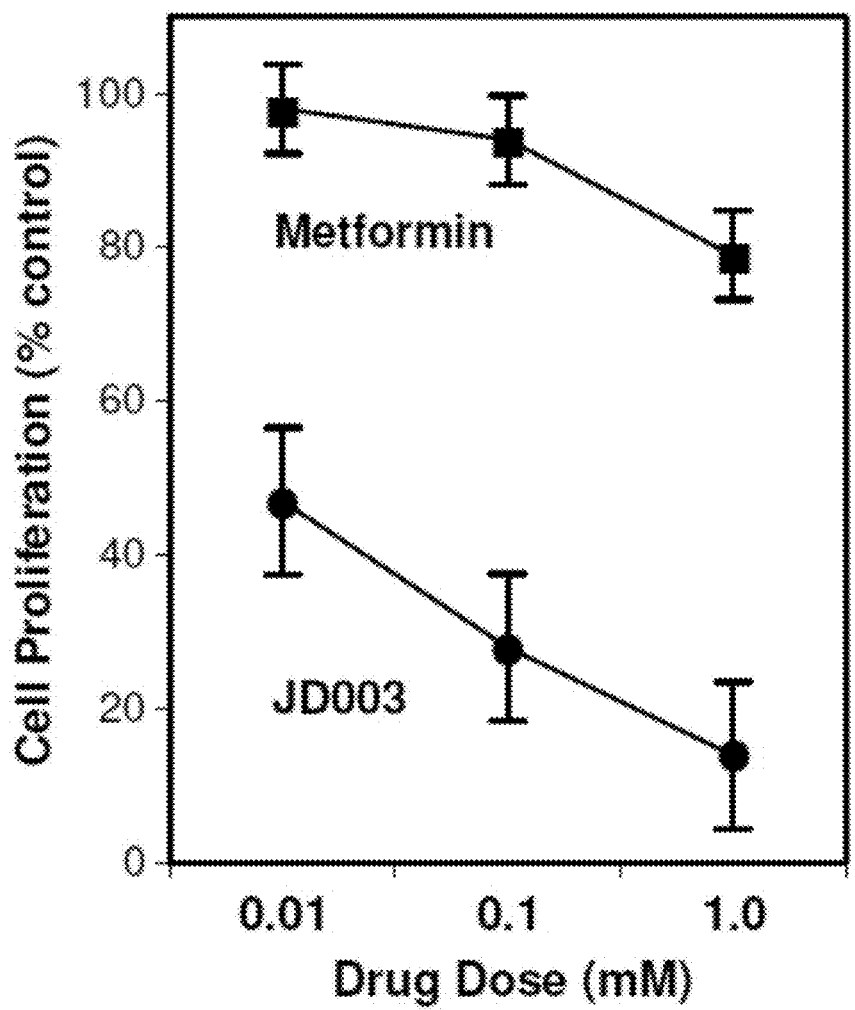
FIG. 5. Metformin analogue JD003 elicits significantly greater inhibition of pancreatic cancer cell proliferation in vitro than parent compound metformin at equivalent doses (P<0.01). Cells were counted and plated. At 24 hrs after plating, cells were treated with metformin and JD003 at 0.01 mM, 0.1 mM, and 1 mM concentrations using medium with 1% FBS. After 72 hrs, cell proliferation was quantitated based on cell counts. Experiments were done 3-times, with results expressed as percent control (mean±SE).
Figure 6A:
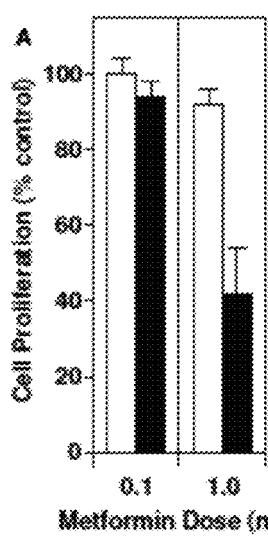
FIGS. 6A-6C. As compared to metformin (FIG. 6A), analogs JD003 (FIG. 6B) and JD004 (FIG. 6C) (Aim 1) are more effective in blocking proliferation of MCF-7 cells but not HMEC. Proliferation was assessed using cell proliferation ELISA, BrdU colorimetric kit (Roche). Cells were counted using a hemocytometer and plated. After 24 hrs, cells were treated with metformin and analogs JD003 and JD004 at 0.1 mM and 1 mM doses using phenol-red free medium with 1% FBS. After 48 hr, BrDU labeling solution was added and incubated for 24 h. Proliferation was assessed using BrDU incorporation by ELISA during DNA synthesis in proliferating cells. Data shown as % control (mean±SE) (n=3 experiments).
Figure 6B:
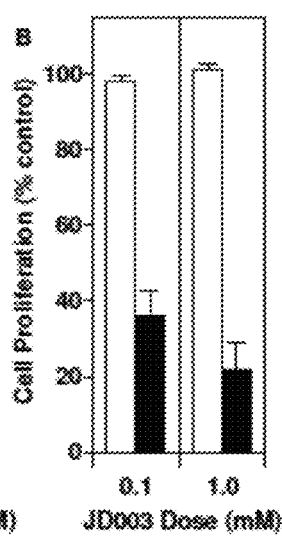
Figure 6C:
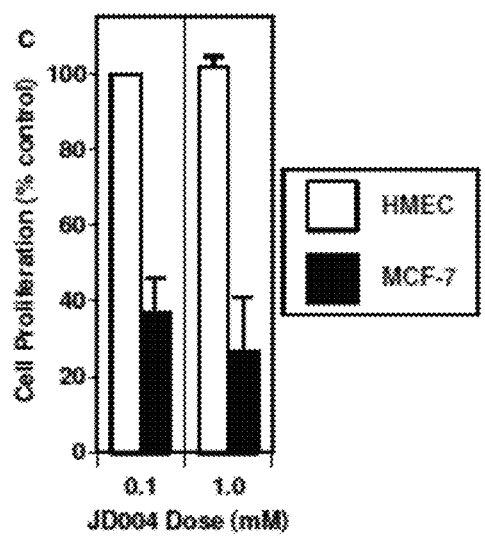
Figure 7:
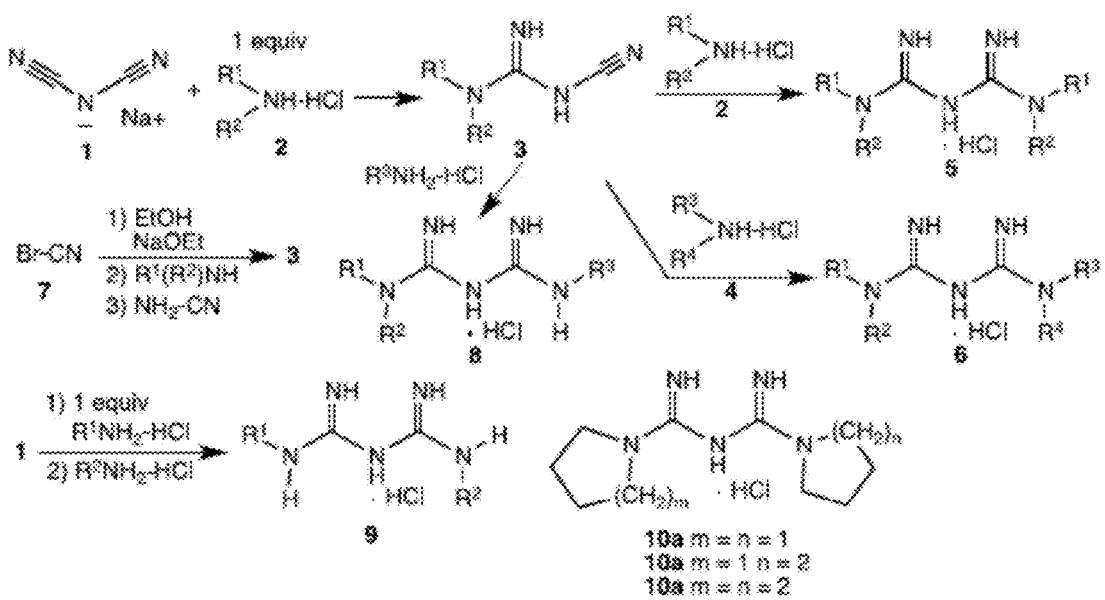
FIG. 7. Chemical structures and synthesis of metformin analogues.
Figure 8:
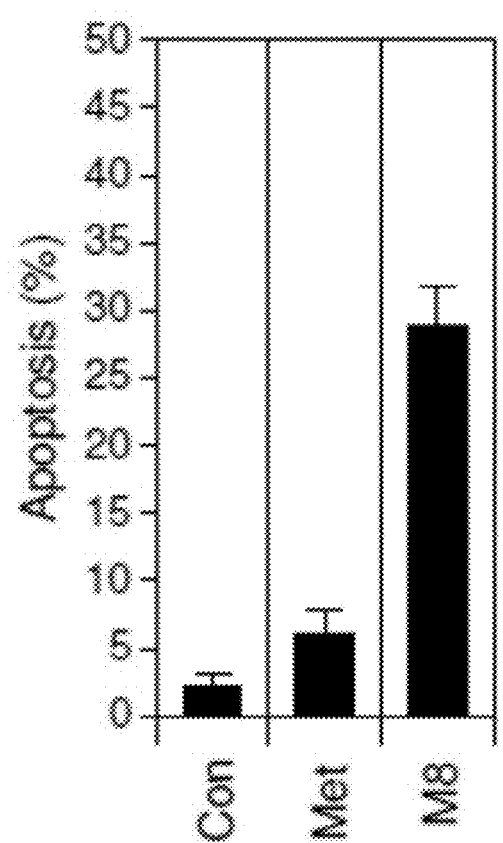
FIG. 8. Metformin analog 8 (M8) stimulates increased apoptosis of PANC-1 cells as compared to controls and parent compound metformin (P<0.001; n=3). Test compounds were administered at 0.1 mM doses, with apoptosis assessed after 48 hr by TUNEL assay (19). M8. (0.01 mM) also markedly inhibited tumor cell proliferation as compared to metformin.

Compounds described herein (e.g. metformin derivatives and/or analogues) were tested in human MCF-7 breast cancer cells, a standard ERalpha-positive model of breast malignancy (FIG. 1), and in four different cell lines classified as TNBC, including MDA-MB-231, HCC1937, HCC38 and HCC1806 (FIGS. 2A-2D). All of the compounds (e.g. metformin analogues and/or derivatives) tested were more effective than metformin at inhibiting cell growth. Experiments were also performed in: 1) a non-small cell lung cancer cell line that is known to be resistant to standard chemotherapy (A549); and 2) a melanoma-like cell model (MDA-MB-435). See FIGS. 3A-3B. To find if analogues have effects on normal cells compounds were tested in two different types of cells, human umbilical vein endothelial cells (HUVEC) and human mammary epithelial cells (HMEC). The effects of metformin (MET) were compared with compounds JD001-JD009. See FIGS. 4A-4B.

Anti-Cancer Activity of Compounds

Described herein is the synthesis of metformin derivatives (e.g. analogues). These novel compounds are shown to be more effective than metformin in killing selected cancer cells. Further, several of these novel metformin derivatives (e.g. analogues) do not display significant side-effects in normal, nonmalignant cells.

Development of novel therapies for the treatment of triple-negative breast cancer (TNBC) are urgently needed as there are currently no targeted therapies for this deadly subtype of breast cancer. Identification of a new targeted and safe therapeutic for TNBC, as well as for other types of cancer (e.g. lung, pancreas, prostate, colon, melanoma, ovary), would be very significant (1).

Preclinical investigations on the anticancer activity of these novel compounds show high potency in both triple-negative breast cancers (about 15-20% of all breast cancers but accounting for almost half of all breast cancer deaths) as well as in estrogen receptor-alpha-positive breast cancers (about 70% of all breast cancers). The compounds described herein (including embodiments) (e.g. metformin analogues) have anticancer effects in melanoma, lung and pancreatic cancer cells. In contrast, several of the new compounds described herein (including embodiments) (e.g. metformin analogues) do not exhibit significant toxicity toward normal nonmalignant human cells used as controls.

Metformin has antitumor activity against triple-negative breast cancer cell lines only at high millimolar concentrations (2,3), while several of the compounds described herein have significantly better specific anticancer activity at lower concentrations (e.g. micromolar) than metformin. Some of the compounds described herein, including embodiments, exhibit anticancer activity when used to treat non-small cell lung cancer. Of note, the antitumor activity of several analogues of metformin appear to differ among different cancers, such as triple-negative breast cancer as compared to non-small cell lung cancer.

The compounds described herein (including embodiments) demonstrate potent anticancer activity toward triple-negative breast cancer (TNBC) and non-small cell lung cancer (NSCLC). The compounds described herein (including embodiments) (e.g. metformin analogues) were shown to be especially active in suppressing TNBC cells, the most deadly subtype of breast cancer, and anticancer activity was also shown for NSCLC and pancreatic cancer cells.

The anticancer activity of some different metformin analogues differs in TNBC as compared to NSCLC, suggesting that specific compounds described herein (including embodiments) may be more potent against different cancer types or subtypes of major groups of cancers and different compounds may be useful for treating different cancer subtypes.

Study of the activity of these metformin analogues in suppressing melanoma and pancreatic cancer are ongoing.

Compounds (e.g. novel metformin derivatives or analogues) are being tested for their ability to treat triple-negative breast cancer (TNBC) using a panel of different cell line models. Experiments on anticancer activity in other breast, lung and pancreatic cancer cells and melanoma are ongoing. Experiments are continuing to determine effects of compounds described herein (including embodiments) on normal cells, including blood vessel cells (e.g. human umbilical vein endothelial cells), nonmalignant breast epithelial cells and normal lung cells (e.g. human bronchial epithelial cells).

Ongoing experiments are determining mechanisms of action of selected compounds, with investigation of cellular and molecular pathways in the induction of tumor cell death. Activation of AMP kinase or inhibition of mTOR (and/or mTORC1), MAPK and AKT kinases and nuclear factor-kappa B pathways are being investigated. Reduction of insulin and insulin-like growth factors (that play a role in tumor progression) and inhibition of the activation of insulin-like growth factor and insulin receptors and their downstream signaling are being characterized. In embodiments, the compounds described herein (including embodiments) modulate (e.g. inhibit, decrease, or increase) the activity or expression levels or function of mTOR, mTORC1, MAPK, and/or AKT kinases. In embodiments, the compounds described herein (including embodiments) modulate (e.g. inhibit, decrease, or increase) the activity or expression level or function of AMP kinase. In embodiments, the compounds described herein (including embodiments) modulate (e.g inhibit, decrease, or increase) the activity or expression levels or function of insulin, insulin-like growth factor 1 (IGF1), insulin-like growth factor 2 (IGF2), IGF1 receptor, or IGF2 receptor.

Experiments are ongoing to characterize compound described herein (including embodiments) in human tumor xenograft models and in orthotopic models for prevention and treatment of lung and breast cancers, particularly TNBC. Compounds are being tested alone or in combination with standard chemotherapy treatments currently used in the clinic (e.g. taxanes, docetaxel).

At a cellular level, metformin stimulates AMP-activated protein kinase (AMPK) activation. Metformin-induced activation of AMPK inhibits downstream mTORC1 which integrates signals from a diverse array of signaling pathways to regulate pancreatic cancer cell survival, growth and metastasis. It is postulated that metformin inhibits pancreatic cancer growth in part via AMPK-mediated inhibition of mTORC1 activation. Independent data show that metformin also disrupts critical cross-talk between insulin/IGF-1 and GPCR signaling pathways and possibly ERK and Rag GTPase signaling. Further laboratory studies show that metformin markedly inhibits growth of human pancreatic cancer cells xenografted in nude mice. This preclinical work is supported by clinical cohort studies showing that metformin users have a reduced risk of pancreatic cancer; and that metformin use correlates with a survival benefit in patients with diabetes and pancreatic cancer. In the latter study, the median survival is only prolonged by 4 months in cancer patients who are metformin users compared to non-users. It is notable that anticancer effects of metformin increase with increasing doses and/or with IV as compared to oral administration. Thus, discovery of more potent anticancer analogs of metformin may be required to boost clinical benefit and patient survival. We design, synthesize and test antitumor activity of new metformin analogs using pancreatic cancer models.

We hypothesize that metformin analogs can be prepared with enhanced anticancer activity and minimal non-target toxicity. Since metformin shows good—although modest activity—in pancreatic cancer, we designed two new analogues of metformin and tested them in early studies for potentially more potent antitumor activity in vitro. Human pancreatic cancer cells PANC-1, were grown in DMEM with 2 mM glutamine, 1 mM sodium pyruvate, 100 units/mL penicillin, 100 µg/mL streptomycin and 10% FBS at 37 C in a humidified atmosphere with 10% $CO_2$. Then, effects of treatment with metformin or analog JD003 on cell proliferation in vitro were tested. These initial findings suggest that analog JD003 shows promise as a congener with more potent antitumor activity. To find if analogs may have deleterious effects on normal human cells, we compared the cellular activity of metformin with that of analogs JD003 and JD004 using a pair of human breast epithelial cells. These included human mammary epithelial cells (HMEC) and MCF-7 tumor cells (MCF-7). Results of this work indicate metformin analogs JD003 and JD004 have enhanced antiproliferative activity in breast cancer cells as compared to metformin at equivalent doses (P<0.01). In contrast, minimal antiproliferative effects are detected in nonmalignant human epithelial cells.

Compounds described herein (including embodiments) may be active in suppressing noncancerous pulmonary lymphangioleiomyomatosis (LAM) and angiomyolipoma (AML) cells that afflict an estimated 300,000 patients worldwide. Use of the compound described herein, including embodiments, (e.g. metformin analogues, metformin derivatives) for noncancerous diseases with dysregulated signaling pathways, such as lymphangioleiomyomatosis (LAM) or angiomyolipoma (AML), is a novel indication (e.g. method of treatment, use). The frequency of these relatively rare diseases is elevated among patients with tuberous sclerosis complex (TSC), an inherited disorder resulting from mutations in either the TSC1 or TSC2 genes, but the diseases may also occur in sporadic cases.

Since metformin has shown good but modest activity against pancreatic cancer in earlier reports, we prepared novel analogs of metformin and test them for potentially more potent antitumor activity. In particular, we prepared some alkylated analogues (e.g., compounds with secondary amines on both ends) since those are largely unknown and therefore could be developed as improved anticancer agents. Compounds in which there is still a free amino group (e.g., phenformin and buformin) are known anticancer agents, but no fully alkylated analogues have been made and tested to date.

A number of metformin analogs have been be prepared. These compounds will be tested and screened using pancreatic tumor cell proliferation, apoptosis and migration/invasion as indices for anticancer activity. Nonmalignant human cells will be tested in parallel to assess effects on normal cells. Modifications in the chemical structure of metformin analogs will be introduced as dictated by the in vitro screening assays for anticancer activity. Lead drug candidates will then be selected and used to probe potential signal transduction pathways that may underlie antitumor effects in pancreatic cancer cells.

Cell Lines and Culture.

Human pancreatic cancer cells PANC-1, MIAPaCa-2, BxPC-3, and AsPC-1 were from ATCC (Manassas, Va.). PANC-1 and MIAPaCa-2 cells were grown in DMEM with 2 mM glutamine, 1 mM sodium pyruvate, 100 units/mL penicillin, 100 µg/mL streptomycin and 10% FBS at 37 C in a humidified atmosphere with 10% CO2 (5). BxPC-3 cells and AsPC-1 cells were grown in RPMI 1640 containing 100 units/mL penicillin, 100 µg/mL streptomycin and 10% FBS at 37 C in a humidified atmosphere with 5% CO2 (5). As controls, human breast cancer MCF-7 cells were obtained from the ATCC and nonmalignant Human Mammary Epithelial Cells (HMEC) obtained from Invitrogen. MCF-7 cells were routinely maintained in D-MEM/F12 (MCF-7) with 10% FBS (Invitrogen/Life Technologies) and 1% antibiotic-antimycotic solution 100×, (Mediatech). HMEC were maintained in medium 171 supplemented with Mammary Epithelial Growth Supplement (Invitrogen). Breast cells were cultured in 37° C. humidified atmosphere/5% CO2.

Cell Proliferation Assays.

Cell proliferation screening assays were done using cell proliferation ELISA, BrdU colorimetric kit (Roche). Cells were counted using a hemocytometer and plated in 96-well plates. At 24 hr after plating, cells were treated with metformin and analogs (see Aim 1) at 0.01 mM, 0.1 mM, 1 mM and 5 mM concentrations using medium with 1% FBS. After 48 hr, BrDU labeling solution was added and incubated for 24 hr. Cell proliferation were quantitated based on measures of BrDU incorporation (by ELISA) during DNA synthesis in proliferating cells. Experiments were performed at least 3-times (n>4/experiment). Results were expressed as mean±SE. Effects of media with or without 10 ng/ml insulin and with or without GPCR agonists such as neurotensin were included in these studies. As an alternate measure of proliferation, independent experiments were done to confirm changes in actual cell numbers.

Anchorage-Independent Cell Proliferation.

Metformin analogs showing significant antitumor activity in screening assays above were tested further using anchorage-independent assays. Pancreatic cancer cells were plated on 12-well plates coated with polyhydroxyethylmethacrylate [poly-(HEMA)]. Under these conditions, cells do not attach to the substratum. Cultures of PANC-1 cells, for example, at 3-5 days after passage, were washed and suspended in DMEM. Cells were then disaggregated by two passes through a 19-gauge needle into single-cell suspension. Cell numbers were determined by Coulter counter, and 2×10$^4$ cells were seeded in DMEM containing 1% FBS on poly-(HEMA)-coated dishes. After 24 hr incubation at 37 C, cells were treated in the absence or presence of metformin and selected analogs at 0.1 and 1.0 mM in media with or without 10 ng/ml insulin and with or without GPCR agonists such as neurotensin (5). Cultures were then incubated at 37 C for 7-9 days, and total cell counts determined from a minimum of 4 wells/condition using a Coulter counter, after cell clumps were disaggregated by passing cell suspensions 10 times through a 19-gauge, and then a 21-gauge needle.

Cell Migration/Invasion Assays.

Since metformin modulates tumor cell invasion (20), migration/invasion of pancreatic tumor cells in Transwell cell culture chambers was assess. For invasion assay, the lower surface of filters were coated with 1 µg of fibronectin, with the upper surface coated with 5 µg of Matrigel. Cells (1×10$^5$) were seeded in the upper compartment and incubated with selected agents or combinations in serum-free medium containing 0.1% BSA at 37° C. for 4 h for migration and 8 h for invasion. Filters were stained with crystal violet, and cells in five 200×-fields will be counted. Such actions allow metastasis in vivo, and blockade of this process is critical to stop tumor spread.

Signal Transduction Assays.

Signal transduction pathways altered by metformin in malignant cells are complex. Crosstalk between insulin and GPCR signaling pathways has been identified in pancreatic cancer cells (2,4,5). Insulin enhances GPCR signaling through a rapamycin-sensitive mTOR-dependent pathway. Metformin is noted to activate AMP kinase (AMPK) which negatively regulates mTORC1. In liver tissue, metformin similarly activates AMPK and inhibits mTOR. In lung tissue, metformin appears to exert greater inhibition on phosphorylation of insulin-like growth factor-I receptor/insulin receptor (IGF-1R/IR), with downstream effects on ERK and mTORC1. This suggests that metformin inhibits mTORC1 in lung tissue in part by decreasing activation of IGF-1R/IR upstream of mTORC1 (9). Here, presented are studies to find if metformin and its analogs elicit activation of AMPK and inhibition of mTORC1. Confluent cultures of pancreatic cancer cells were grown on 6-cm dishes, washed twice with PBS and then incubated with serumfree medium for 3 h. Metformin or analogs were added at 0.01, 0.1, 1 mM, and cultures were incubated at 37 C for selected times (0-24 h). To detect AMPK activation, cultures were washed in cold PBS and directly lysed in 2×SDS-PAGE sample buffer [200 mM Tris-HCl (pH 6.8), 2 mM EDTA, 0.1 mM Na3VO4, 6% SDS, 10% glycerol, 4% 2-mercaptoethanol]. Lysates were subjected to SDS-PAGE on 10% gels and separated proteins were transferred to Immobilon-P membranes (Millipore). Western blots were then done on membranes incubated overnight with phosphorylated AMPKa (Thr172) or phosphorylated ERK1/2 (Thr202 and Tyr204) monoclonal antibodies at a dilution of 1:1,000 in PBS containing 5% nonfat dried milk and 0.1% Tween 20. Immunoreactive bands were detected with enhanced chemiluminescence reagents. Membranes were subsequently stripped and probed similarly with anti-AMPKa polyclonal antibody or anti-ERK at a dilution of 1:2,000 in PBS containing 5% nonfat dried milk and 0.1% Tween 20. Study of the phosphorylation of IGF-1R/IR using specific antibodies (Cell Signaling) were done.

A decrease in translation caused by metformin in some tumors is associated with mTORC1 inhibition, and a decrease in phosphorylation of S6 kinase and ribosomal protein S6. Such effects of metformin on translation appear to be mediated in part by AMPK, as treatment of cells with the AMPK inhibitor compound C prevents inhibition of translation. To test if antitumor effects of metformin analogs are mediated by limiting mTORC1 signaling, we assessed the relative efficacy of metformin congeners and rapamycin (control) to block phosphorylation of downstream mTORC1 mediators, S6K and S6, and mTORC1.

Statistical Analysis.

Triplicates of experiments were done to verify results. Data are presented as mean+SE and analyzed with student's t-test or other appropriate nonparametric tests. ANOVA, or the Kruskal Wallis test if outcomes are non-normally distributed, are used as appropriate to compare multiple intervention groups. Analyses were evaluated using bar/scatter graphs with means, SD and SE.

Administration of metformin is reported to significantly decrease growth of MIAPaCa-2 and PANC-1 cells xenografted in nude mice. Thus, a potent metformin analogue for in vivo studies was selected on the basis of in vitro experiments to assess optimal antitumor efficacy and target specificity. For a tumor xenograft model, nude mice (Harlan-Sprague-Dawley) were injected subcutaneously with, for example, 5×106 PANC-1 cells using established methods. After implanted tumor cells achieve an average size of 50-100 cm3, mice were randomized into the following groups (n=10 mice/group): (a) vehicle control, (b) metformin control, c) analog 1, d) analog 2 and e) analog 3, with all agents given by oral gavage once daily.

Tumors were measured in two dimensions every 2-3 days, with area calculated by multiplying length by width. Therapy was given until tumors reach limiting sizes or until day 28 in the analog-treated group. At the end of studies, mice were anesthetized using isoflurane, and blood was collected by cardiac puncture using BD vacutainer vials containing EDTA. Animals were then euthanized with CO2 by established guidelines. Tumors and liver tissues were harvested to assess weights and processed for study of potential biomarkers. Final tumor weights and sizes were compared among the several treatment groups.

Immunohistochemistry (IHC).

For biomarker analyses, formalin-fixed pancreatic tumor tissue were paraffin-embedded, sectioned and placed on slides. We have experience in IHC studies and assessed all antibodies for specificity and use appropriate controls. IHC analysis of phosphorylation of AMPK, S6, IGF-1R/IR, AKT and ERK 1/2; and for Ki-67 was performed. Antigen retrieval was done using target retrieval solution (pH 6.0) and a decloaking chamber (Dako). Tissues were incubated, for example, in phospho-AMPK (1:50), phospho-S6 (1:100) (22-24), Ki-67 (1:2,000) antibodies per manufacturer's recommendations. Assessment of phosphorylation of IGF-1R/IR, AKT and ERK 1/2 (dilutions to be determined) was also performed. To verify staining specificity, tissues were incubated in the absence of primary antibody (24). Detection was done using VECTASTAIN Elite ABC kits (Vector Laboratories). IHC analysis for biomarkers was quantified and scored using methods as before. Ki-67 staining was quantified by counting the number of Ki-67+ cells per tumor, and these values were averaged for tumors in mice from each treatment group. The investigator performing these analyses was blinded to identities of the samples. As an alternative approach, samples of pancreatic cancer xenograft and liver tissues at harvest were flash-frozen in liquid nitrogen. Frozen tissues were then be pulverized on dry ice and lysates prepared using RIPA buffer supplemented with protease and phosphatase inhibitors. Immunoblotting analysis of tissue lysates was done as described previously. Densitometry was done using NIH Image software at our institution.

Exploratory Pharmacokinetic Analysis of Drug Plasma Levels.

Sample preparation and analysis were done. In brief, plasma was isolated by centrifugation of blood samples collected from mice at the end of xenograft studies and sent to a UCLA or commercial analytical laboratory (Laboratory of Proteomics & Analytical Technologies, Frederick, Md.) for pharmacokinetic analysis of metformin and analogs.

Plasma IGF-I and Insulin Analysis.

Plasma levels of IGF-I and insulin were measured using the Mouse/Rat IGF-I ELISA (Diagnostic Systems Laboratories) and the Rat/Mouse Insulin ELISA kit (Millipore), respectively. Analyses were done on plasma obtained from mice at the end of the xenograft studies.

Disease Prevention Using Compounds Described Herein (e.g. Metformin Analogues)

There is a potential for use of the compounds described herein (including embodiments) in cancer prevention among individuals at high risk for cancer (for example, those with a significant history of diabetes, obesity, metabolic syndrome, tobacco smoking or evidence of premalignant lung or other tissue lesions). In embodiments, the compounds described herein (including embodiments) are administered by oral administration.

Treatment of Non-Cancer Diseases

TABLE 1

Metformin analogues/derivatives[1]

| Code | Structure | Biodata TNBC | | | | ER + | Biodata Normal | | Biodata extra | |
|---|---|---|---|---|---|---|---|---|---|---|
| | | MDA-MB-231 | HCC1937 | HCC38 | HCC1806 | BC MCF7 | HUVEC | HMEC | A549 | MDA-MB-435 |
| Metformin (000) | | 110.3 | 92.9 | 92.5 | 90.2 | 104.8 | 83.9 | 99.8 | 72.2 | 77.7 |
| JD001 | | 92 | 68.9 | 102.5 | 80.1 | 82.3 | 84.4 | 101 | 62.6 | 102.1 |
| JD002 | | 48.5 | 17.1 | 44.7 | 36.4 | 46.2 | 70 | 62.6 | 4.6 | 39.8 |
| JD003 | | 93.2 | 37.8 | — | — | 61.3 | 86.7 | 106.6 | 98 | 50.4 |
| JD004 | | 89.2 | 64 | — | — | 84.4 | 89.1 | 112.8 | 74.3 | 59.6 |
| JD005 | | 46.6 | 15.7 | 43.4 | 55.8 | 58.2 | 54.6 | 67.6 | 32.4 | 42.2 |
| JD006 | | — | — | — | — | 59.7 | 112.8 | 96.6 | 59.7 | — |

TABLE 1-continued

Metformin analogues/derivatives[1]

| | | Biodata TNBC | | | | ER + BC | Biodata Normal | | Biodata extra | |
| | | MDA- | | | | | | | MDA- | |
| Code | Structure | MB-231 | HCC1937 | HCC38 | HCC1806 | MCF7 | HUVEC | HMEC | A549 | MB-435 |
|---|---|---|---|---|---|---|---|---|---|---|
| JD007 | | 64.3 | — | 83.6 | 65.7 | 65.8 | 112.1 | 105.3 | 82.3 | — |
| JD008 | | 38.6 | — | 55.6 | 52.7 | 52.2 | 37.7 | 70.9 | — | — |
| JD009 | | 0.3 | — | 0 | 7.3 | 52.7 | 39.5 | 48.8 | — | — |

Figure 9:
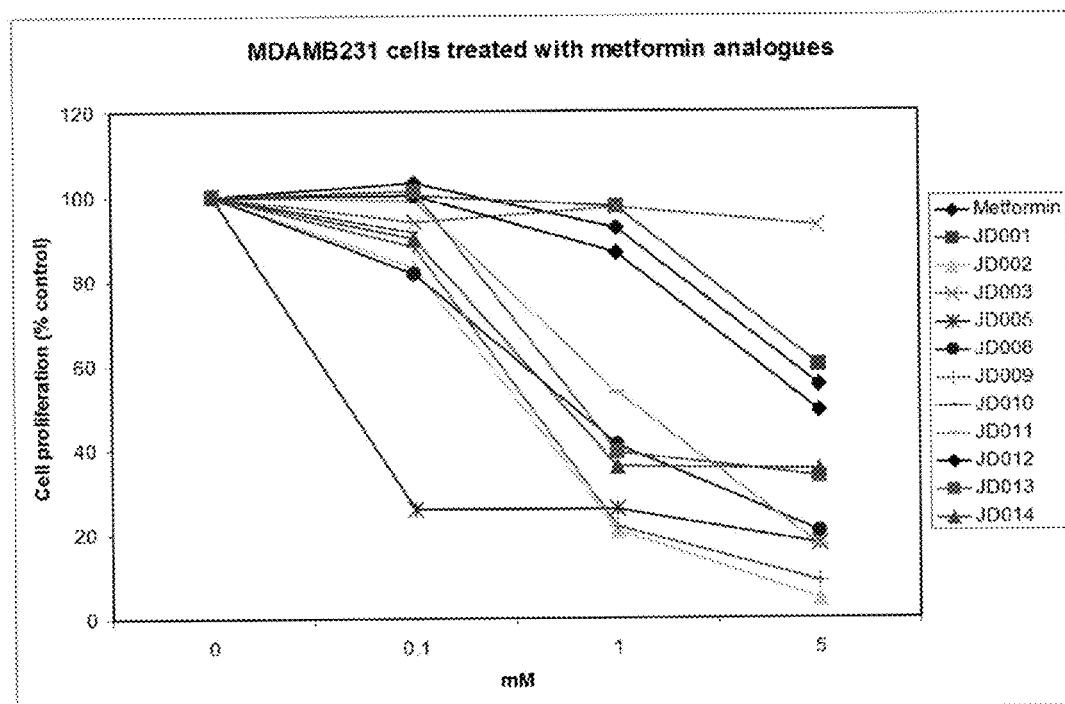
FIG. 9. Triple-negative MDA-MB-231 breast cancer cells treated with compounds described herein.

[1]Additional data noted in FIG. 9.

Cells were incubated in the presence of vehicle, metformin or metformin analogues for 72 hours in their respective media. After treatment cell numbers were determined with the MTS method using the CellTiter 96 Aqueous Non-Radioactive Cell Proliferation Assay (Promega). Numbers express percentage of vehicle treated controls at 1 mM concentration metformin or metformin analogues (JD001-JD009). TNBC: Triple Negative Breast Cancer Cells, ER+BC: Estrogen receptor positive breast cancer.

Since metformin has shown good but modest activity against pancreatic cancer in earlier reports, we prepared novel analogs of metformin and test them for potentially more potent antitumor activity. In particular, we prepared alkylated analogues (e.g., compounds with secondary amines on both ends) since those are largely unknown and therefore could be developed as improved anticancer agents. Compounds in which there is still a free amino group (e.g., phenformin and buformin) are known anticancer agents, but no fully alkylated analogues have been made and tested to date.

VII. References

1. Evans J M, Donnelly L A, Emslie-Smith A M, Alessi D R, Morris A D. Metformin and reduced risk of cancer in diabetic patients. BMJ. 2005, 4; 330(7503):1304-5.
2. Jiralerspong S, Palla S L, Giordano S H, Meric-Bernstam F, Liedtke C, Barnett C M, Hsu L, Hung M C, Hortobagyi G N, Gonzalez-Angulo A M. Metformin and pathologic complete responses to neoadjuvant chemotherapy in diabetic patients with breast cancer. J Clin Oncol. 2009, 27(20):3297-302.
3. Dowling R J, Goodwin P J, Stambolic V. Understanding the benefit of metformin use in cancer treatment. 2011, BMC Med, 9:33.
4. Taubes G. Cancer research. Unraveling the obesity-cancer connection. Science. 2012 Jan. 6; 335(6064):28, 30-2.
5. Currie C J, Poole C D, Jenkins-Jones S, Gale E A, Johnson J A, Morgan C L. Mortality after incident cancer in people with and without type 2 diabetes: impact of metformin on survival. Diabetes Care. 2012; 35(2):299-304.
6. Jiralerspong S, Gonzalez-Angulo A M, Hung M C. Expanding the arsenal: metformin for the treatment of triple-negative breast cancer? Cell Cycle. 2009 Sep. 1; 8(17):2681.
7. Jiralerspong S, Palla S L, Giordano S H, Meric-Bernstam F, Liedtke C, Barnett C M, Hsu L, Hung M C, Hortobagyi G N, Gonzalez-Angulo A M. Metformin and pathologic complete responses to neoadjuvant chemotherapy in diabetic patients with breast cancer. J Clin Oncol. 2009 Jul. 10; 27(20):3297-302. Epub 2009 Jun. 1.
8. Ben Sahra I, Le Marchand-Brustel Y, Tanti J F, Bost F. Metformin in cancer therapy: a new perspective for an old antidiabetic drug? Mol Cancer Ther. 2010 May; 9(5): 1092-9. Review.
9. Dilman V M, Berstein L M, Ostroumova M N, Fedorov S N, Poroshina T E, Tsyrlina E V, Buslaeva V P, Semiglazov V F, Seleznev I K, Bobrov Yu F, Vasilyeva I A, Kondratjev V B, Nemirovsky V S, Nikiforov Y F. Metabolic immunodepression and metabolic immunotherapy: an attempt of improvement in immunologic response in breast cancer patients by correction of metabolic disturbances. Oncology. 1982; 39(1):13-9.
10. Berstein L M. Modern approach to metabolic rehabilitation of cancer patients: biguanides (phenformin and metformin) and beyond. Future Oncol. 2010 August; 6(8):1313-23. Review.
11. Foulkes W D, Smith I E, Reis-Filho J S. Triple-negative breast cancer. N Engl J Med. 2010, 363(20):1938-48.

12. Carey L A, Perou C M, Livasy C A, Dressler L G, Cowan D, Conway K, Karaca G, Troester M A, Tse C K, Edmiston S, Deming S L, Geradts J, Cheang M C, Nielsen T O, Moorman P G, Earp H S, Millikan R C. Race, breast cancer subtypes, and survival in the Carolina Breast Cancer Study. JAMA. 2006 Jun. 7; 295(21):2492-502.
13. Liu B, Fan Z, Edgerton S M, Deng X S, Alimova I N, Lind S E, Thor A D. Metformin induces unique biological and molecular responses in triple negative breast cancer cells. Cell Cycle. 2009 Jul. 1; 8(13):2031-40.
14. Alimova I N, Liu B, Fan Z, Edgerton S M, Dillon T, Lind S E, Thor A D. Metformin inhibits breast cancer cell growth, colony formation and induces cell cycle arrest in vitro. Cell Cycle. 2009 Mar. 15; 8(6):909-15.
15. James, John W.; Baker, James A.; Wiggins, Leslie F. Journal of Medicinal Chemistry (1968), 11(5), 942-5.
16. Kihara, Yoshito; Kabashima, Shigeru; Yamasaki, Tetsuo; Ohkawara, Tadashi; Furukawa, Mitsuru Journal of Heterocyclic Chemistry (1990), 27(5), 1913-16.
17. Kelarev, V. I.; Karakhanov, R. A.; Polivin, Yu. N.; Kuatbekov, A. M.; Remizov, A. S.; Mikaya, A. I., Khimiya Geterotsiklicheskikh Soedinenii (1993), (9), 1271-6.
18. Kelarev, V. I.; Karakhanov, R. A.; Kokosova, A. S.; Gankin, G. D. Khimiya Geterotsiklicheskikh Soedinenii (1992), (9), 1250-6.
19. Kelarev, V. I.; Karakhanov, R. A.; Bellul, M.; Ushakova, R. L.; Mikaya, A. I. Khimiya Geterotsiklicheskikh Soedinenii (1988), (5), 674-80.
20. Nagasaka, Hideki; Ichikawa, Eiichi; Odo, Keijiro Yuki Gosei Kagaku Kyokaishi (1967), 25(9), 802-7.

What is claimed is:

1. A compound having the formula:

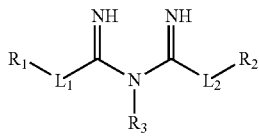

wherein;

$L^1$ and $L^2$ are independently a bond or —NH—C(NH)—;
$R^1$ is —$NR^{1A}R^{1B}$, wherein $R^{1A}$ and $R^{1B}$ are independently substituted or unsubstituted alkyl and are joined together to form a substituted or unsubstituted pyrrolidinyl, or an unsubstituted piperidinyl;
$R^2$ is —$NR^{2A}R^{2B}$, wherein $R^{2A}$ and $R^{2B}$ are independently substituted or unsubstituted alkyl and are joined together to form a substituted or unsubstituted pyrrolidinyl; and
$R^3$ is hydrogen or unsubstituted $C_1$-$C_5$ alkyl.

2. The compound of claim 1, wherein $L^1$ and $L^2$ are bonds and $R^3$ is hydrogen.

3. The compound of claim 2, wherein $R^{1A}$ and $R^{1B}$ are joined together to form an unsubstituted piperidinyl.

4. The compound of claim 1, wherein said compound has the formula:

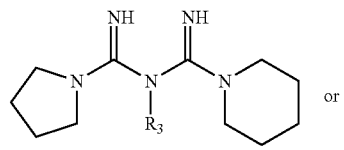

(005)

or

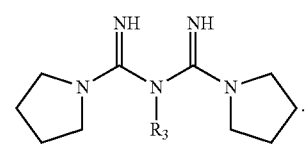

(006)

5. The compound of claim 4, wherein $R^3$ is hydrogen.

6. A pharmaceutical composition comprising a pharmaceutically acceptable excipient and a compound having formula:

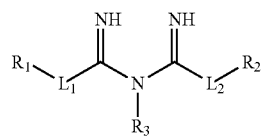

wherein;

$L^1$ and $L^2$ are independently a bond or —NH—C(NH)—;
$R^1$ is —$NR^{1A}R^{1B}$, wherein $R^{1A}$ and $R^{1B}$ are independently substituted or unsubstituted alkyl and are joined together to form a substituted or unsubstituted pyrrolidinyl, or an unsubstituted piperidinyl;
$R^2$ is —$NR^{2A}R^{2B}$, wherein $R^{2A}$ and $R^{2B}$ are independently substituted or unsubstituted alkyl and are joined together to form a substituted or unsubstituted pyrrolidinyl; and
$R^3$ is hydrogen or unsubstituted $C_1$-$C_5$ alkyl.

7. The pharmaceutical composition of claim 4, wherein said compound has the formula:

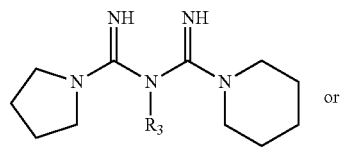

(005)

or

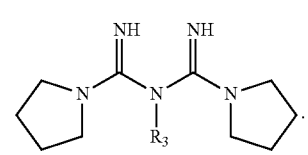

(006)

* * * * *